(12) United States Patent
Pfefferkorn

(10) Patent No.: US 7,446,121 B2
(45) Date of Patent: Nov. 4, 2008

(54) PYRAZOLE-BASED HMG COA REDUCTASE INHIBITORS

(75) Inventor: Jeffrey A. Pfefferkorn, Dexter, MI (US)

(73) Assignee: Pfizer Inc., New York, NY (US)

( * ) Notice: Subject to any disclaimer, the term of this patent is extended or adjusted under 35 U.S.C. 154(b) by 517 days.

(21) Appl. No.: 11/283,264

(22) Filed: Nov. 18, 2005

(65) Prior Publication Data

US 2006/0111422 A1    May 25, 2006

Related U.S. Application Data

(60) Provisional application No. 60/630,481, filed on Nov. 23, 2004.

(51) Int. Cl.
*A61K 31/415* (2006.01)
*C07D 231/10* (2006.01)

(52) U.S. Cl. .................. 514/406; 548/356.1; 548/373.1; 548/374.1; 514/403

(58) Field of Classification Search .............. 548/356.1, 548/373.1, 374.1; 514/403, 406
See application file for complete search history.

(56) References Cited

U.S. PATENT DOCUMENTS

| | | |
|---|---|---|
| 3,261,859 A | 7/1966 | Dengel et al. |
| 3,262,977 A | 7/1966 | Harsanyi et al. |
| 3,683,080 A | 8/1972 | Francis |
| 3,752,814 A | 8/1973 | Fluckiger et al. |
| 3,752,888 A | 8/1973 | Fluckiger et al. |
| 3,822,287 A | 7/1974 | Bolger et al. |
| 3,857,952 A | 12/1974 | Wooldridge et al. |
| 3,932,400 A | 1/1976 | Hibino et al. |
| 3,962,238 A | 6/1976 | Mauvernay et al. |
| 4,062,950 A | 12/1977 | Frommer et al. |
| 4,133,814 A | 1/1979 | Jones et al. |
| 4,174,439 A | 11/1979 | Rauenbusch et al. |
| 4,189,438 A | 2/1980 | Umezawa et al. |
| 4,217,305 A | 8/1980 | Imai et al. |
| 4,217,307 A | 8/1980 | Planker et al. |
| 4,242,453 A | 12/1980 | Umezawa et al. |
| 4,248,883 A | 2/1981 | Sawayama et al. |
| 4,254,256 A | 3/1981 | Otani et al. |
| RE30,577 E | 4/1981 | Busch et al. |
| 4,273,765 A | 6/1981 | Suhara et al. |
| 4,405,644 A | 9/1983 | Kabbe et al. |
| 4,410,520 A | 10/1983 | Watthey |
| 4,418,068 A | 11/1983 | Jones |
| 4,451,455 A | 5/1984 | Vertesy et al. |
| 4,452,813 A | 6/1984 | Fujii et al. |
| 4,536,516 A | 8/1985 | Harper et al. |
| 4,567,175 A | 1/1986 | Takeda et al. |
| 4,572,909 A | 2/1986 | Campbell et al. |
| 4,598,089 A | 7/1986 | Hadvary et al. |
| 4,613,610 A | 9/1986 | Wareing |
| 4,623,660 A | 11/1986 | Richardson |
| 4,623,714 A | 11/1986 | Vertesy et al. |
| 4,631,286 A | 12/1986 | Shutske et al. |
| 4,634,765 A | 1/1987 | Liu |
| 4,639,436 A | 1/1987 | Junge et al. |
| 4,663,318 A | 5/1987 | Davis |
| 4,681,893 A | 7/1987 | Roth |
| 4,701,559 A | 10/1987 | Horii et al. |
| 4,766,121 A | 8/1988 | Ellis et al. |
| 4,816,456 A | 3/1989 | Summers |
| 4,826,876 A | 5/1989 | Ellis et al. |
| 4,839,155 A | 6/1989 | McCague |
| 4,879,303 A | 11/1989 | Davison et al. |
| 4,895,841 A | 1/1990 | Sugimoto et al. |
| 4,910,305 A | 3/1990 | Ellis et al. |
| 4,929,629 A | 5/1990 | Jeffery |
| 4,948,807 A | 8/1990 | Rosini et al. |
| 4,957,971 A | 9/1990 | Picard et al. |
| 4,996,225 A | 2/1991 | Toivola et al. |
| 5,061,798 A | 10/1991 | Emmett et al. |
| 5,091,524 A | 2/1992 | Vertesy et al. |
| 5,155,120 A | 10/1992 | Lazar et al. |
| 5,157,116 A | 10/1992 | Ducep et al. |
| 5,185,351 A | 2/1993 | Finkelstein et al. |
| 5,192,772 A | 3/1993 | Yoshikuni et al. |
| 5,196,444 A | 3/1993 | Naka et al. |

(Continued)

FOREIGN PATENT DOCUMENTS

DE    3918364 A1    12/1990

(Continued)

OTHER PUBLICATIONS

Dutch Search Report No. 1030487 dated Aug. 22, 2006, 6 pages.

(Continued)

*Primary Examiner*—Golam M Shameem
(74) *Attorney, Agent, or Firm*—Gregg C. Benson; Rona A. Nardone

(57) ABSTRACT

Novel compounds and pharmaceutical compositions useful as hypocholesterolemic and hypolipidemic agents are described. More specifically, potent inhibitors of the enzyme 3-hydroxy-3-methylglutaryl-coenzyme A reductase ("HMG CoA reductase") are described. Methods of using such compounds and compositions to treat subjects, including humans, suffering from hyperlipidemia, hypercholesterolemia, hypertriglyceridemia, atherosclerosis, Alzheimer's Disease, benign prostatic hypertrophy (BPH), diabetes and osteoporosis are also described.

12 Claims, No Drawings

U.S. PATENT DOCUMENTS

| | | | |
|---|---|---|---|
| 5,273,995 | A | 12/1993 | Roth |
| 5,274,143 | A | 12/1993 | Ramig et al. |
| 5,284,971 | A | 2/1994 | Walker et al. |
| 5,391,571 | A | 2/1995 | Mewshaw et al. |
| 5,401,772 | A | 3/1995 | Yokoyama et al. |
| 5,420,305 | A | 5/1995 | Ramig et al. |
| 5,484,795 | A | 1/1996 | Bryant et al. |
| 5,488,058 | A | 1/1996 | Palkowitz |
| 5,504,078 | A | 4/1996 | Ducep et al. |
| 5,510,379 | A | 4/1996 | Lee et al. |
| 5,512,565 | A | 4/1996 | Mewshaw et al. |
| 5,540,917 | A | 7/1996 | Isler et al. |
| 5,552,412 | A | 9/1996 | Cameron et al. |
| 5,569,674 | A | 10/1996 | Yokoyama et al. |
| 5,602,151 | A | 2/1997 | Mewshaw et al. |
| 5,643,874 | A | 7/1997 | Bremer et al. |
| 5,654,468 | A | 8/1997 | Yokoyama et al. |
| 5,728,704 | A | 3/1998 | Mylari et al. |
| 5,861,385 | A | 1/1999 | Angerbauer et al. |
| 5,866,578 | A | 2/1999 | Mylari et al. |
| 5,969,156 | A | 10/1999 | Briggs et al. |
| 5,985,864 | A | 11/1999 | Imai et al. |
| 6,099,863 | A | 8/2000 | Gilis et al. |
| 6,132,774 | A | 10/2000 | Ke et al. |
| 6,140,321 | A | 10/2000 | Imai et al. |
| 6,140,343 | A | 10/2000 | DeNinno et al. |
| 6,197,786 | B1 | 3/2001 | DeNinno et al. |
| 6,245,911 | B1 | 6/2001 | Imai et al. |
| 6,372,760 | B1 | 4/2002 | Kato et al. |
| 6,710,063 | B1 | 3/2004 | Chao |
| 6,723,752 | B2 | 4/2004 | Sikorski et al. |
| 6,723,753 | B2 | 4/2004 | Sikorski et al. |
| 2003/0171377 | A1 | 9/2003 | Bigge et al. |
| 2003/0225158 | A1 | 12/2003 | Auerbach et al. |
| 2004/0157885 | A1 | 8/2004 | Bagley et al. |
| 2004/0197398 | A1 | 10/2004 | Friesen et al. |

FOREIGN PATENT DOCUMENTS

| | | |
|---|---|---|
| EP | 0 252 476 | 1/1988 |
| EP | 0 475 627 | 3/1992 |
| JP | 08-143457 | 6/1996 |
| WO | WO 86/00307 | 1/1986 |
| WO | WO 94/00480 | 1/1994 |
| WO | WO 95/10513 | 4/1995 |
| WO | WO 96/10559 | 4/1996 |
| WO | WO 96/26948 | 9/1996 |
| WO | WO 96/39384 | 12/1996 |
| WO | WO 96/39385 | 12/1996 |
| WO | WO 96/40640 | 12/1996 |
| WO | WO 98/23593 | 6/1998 |
| WO | 9932434 A1 | 1/1999 |
| WO | WO 99/12933 | 3/1999 |
| WO | 2005105079 A2 | 11/2005 |

OTHER PUBLICATIONS

Ransac, Stephane, et al, "[10] Covalent Inactivation of Lipases", Methods in Enzymology, vol. 286, pp. 190-231, 1997.

Grier, et al, "The Use of Dual Energy X-ray Absorptiometry in Animals", Investigative Radiology, vol. 31(1), pp. 50-62, 1996.

Colowick, et al, "Methods in Enzymology", Academic Press Inc., Publishers New York, vol. 1, 1955, pp. 149-159.

Peterson, Von Siegfried, "Neidermolekulare Umsetzungsprodkte aliphatischer Diisocyante", Liebig's Annalen, 1949, 562, pp. 205-229.

Kitahara, et al, "Valilactone, an Inhibitor of Esterase, Produced By Actinomycetes", J. of Antibiotics, 40(1), 1987, pp. 1647-1650.

Umezawa, et al, "Ebelactone, an Inhibitor of Esterase, Produced By Actinomycetes", J. of Antibiotics, 33, 1980, pp. 1594-1596.

Wetterau, et al, "Absence of Microsomal Triglyceride Transfer Protein in Individuals with Abetalipoproteinemia", Science, vol. 258, Nov. 6, 1992, pp. 999-1001.

Crook, et al, "Isolation and Characterization of Several Plasma Apolipoproteins of Common Marmoset Monkey", Arteriosclerosis, vol. 10, No. 4, Jul./Aug. 1990, pp. 625-632.

McKenney, James M., "Pharmacologic Characteristics of Statins", Clin. Cardiol., vol. 26 (Suppl. III), III-32-III-38 (2003).

The Lipid Research Clinics Coronary Primary Prevention Trial Results, J American Medical Assoc., 1984, vol. 251, No. 3, pp. 351-374.

Brown, et al, "Lowering Plasma Cholesterol By Raising LDL Receptors", The New England Journal of Medicine, vol. 305, No. 9, pp. 515-517.

Berge, et al, "Pharmaceutical Salts", J of Pharmaceutical Sciences, Jan. 1977, vol. 66, No. 1, pp. 1-19.

Ong, et al, "Assay of 3-Hydroxy-3-methylglutaryl CoA Reductase Activity Using Anionic-Exchange Column Chromatography", Analyt. Biochem., 1991, vol. 196, pp. 211-214.

Stephan, et al, "Demonstration of potent lipid-lowering activity by a thyromimetic agent devoid of cardiovascular and thermogenic effects", Atherosclerosis, vol. 126, 1996, pp. 53-63.

Dahlquist, et al, "Application of Secondary Alpha-Deuterium Kinetic Isotope Effects to Studies of Enzyme Catalysis. Glycoside Hydrolysis by Lysozyme and Beta-Glucosidase", Biochemistry, vol. 8, No. 10, Oct. 1969, pp. 4214-4221.

Siegel, et al, "An Enzymatic Fluorometric Assay for Fructose", Analyt. Biochem., vol. 280, 2000, pp. 329-331.

Blount, et al, "Synthesis of Some 2-Aminofurans from Cyanoacetone Enolate and Their Rearrangement to 3-Cyanopyrroles with Ammonia", J. Org. Chem., vol. 43, No. 20, 1978, pp. 3821-3824.

Konoike, et al, "Practical Synthesis of Chiral Synthons for the Preparation of HMG-CoA Reductase Inhibitors", J. Org. Chem., vol. 59, 1994, pp. 7849-7854. Abstract published Nov. 1, 1994.

Kesseler, et al, "Stereoselective Synthesis of HR 780 A New Highly Potent HMG CoA Reductase Inhibitor", Tetrahedron Letters, vol. 31, No. 18, 1990, pp. 2545-2548.

Broggini, et al, "Asymmetric induction by the (S)-1-phenylethyl group in intramolecular nitrile imine cycloadditions giving enantiopure 3,3a-dihydro-pyrazolo[1,5-a][1,4]benzodiazepine-4(6H)-ones", Tetrahedron: Asymmetry, vol. 10, 1999, pp. 4447-4454.

Ghosh, et al, "8,9-Dihydroxy-2,3,7,11b-tetrahydro-1H-naph[1,2,3-de]isoquinoline: A Potent full Dopamine D1 Agonist Containing a Rigid Beta-Phenyldopamine Pharmacophore", J. Med. Chem., 1996, vol. 39, pp. 549-555. Abstract published, Dec. 15, 1995.

Hoover, et al, "Indole-2-carboxamide Inhibitors of Human Liver Glycogen Phosphorylase", J. Med. Chem., vol. 41, 1998, pp. 2934-2938. Published on web Jul. 30, 1998.

Harwood, et al, "Pharmacologic consequences of cholesterol absorption inhibition: alteration in cholesterol metabolism and reduction in plasma cholesterol concentration induced by the synthetic saponin beta-tigogenin cellobioside (CP-88818; tiqueside)", J. of Lipid Res., vol. 34, 1993, pp. 377-395.

Heider, et al, "Role of acyl CoA:cholesterol acyltransferase in cholesterol absorption and its inhibition by 57-118 in the rabbit", J. of Lipid Res., vol. 24, 1983, pp. 1127-1134.

Willson, et al, "Dissection of the Molecular Mechanism of Action of GW5638, a Novel Estrogen Receptor Ligand, Provides Insights into the Role of Estrogen Receptor in Bone", Endocrinology, vol. 138, No. 9, pp. 3901-3911.

Ness, et al, "Atorvastatin action involves diminished recovery of hepatic HMG-CoA reductase activity", J. of Lipid Res., vol. 39, Jan. 1998, pp. 75-84.

Malone, et al, "Red Cell Sorbitol, An Indicator of Diabetic Control", Diabetes, vol. 29, Nov. 1980, pp. 861-864.

Zarantonello, et al, "Total Synthesis and Semi-Synthetic Approaches to Analogues of Antibacterial Natural Product Althiomycin", Bioorganic & Medicinal Chemistry Letters, vol. 12, No. 4, 2002, pp. 561-565.

PYRAZOLE-BASED HMG COA REDUCTASE INHIBITORS

RELATED APPLICATIONS

This application claims benefit of priority under 35 U.S.C 119(e) to U.S. Provisional Application No. 60/630,481 filed on Nov. 23, 2004, which is hereby incorporated in its entirety by reference.

BACKGROUND OF THE INVENTION

High levels of blood cholesterol and blood lipids are conditions involved in the onset of atherosclerosis. The conversion of HMG-CoA to mevalonate is an early and rate-limiting step in the cholesterol biosynthetic pathway. This step is catalyzed by the enzyme HMG-CoA reductase. It is known that inhibitors of HMG-CoA reductase are effective in lowering the blood plasma level of low density lipoprotein cholesterol (LDL-C), in man. (cf. M. S. Brown and J. L. Goldstein, *New England Journal of Medicine,* 305, No. 9, 515-517 (1981)). It has been established that lowering LDL-C levels affords protection from coronary heart disease (cf. *Journal of the American Medical Association,* 251, No. 3, 351-374 (1984)).

To varying degrees, statins interfere with and/or inhibit HMG-CoA reductase from catalyzing the conversion of HMG-CoA to mevalonate. As such, statins are collectively potent lipid lowering agents. Thus, statins are the drugs of first choice for management of many lipid disorders. One representative statin is atorvastatin.

Atorvastatin and pharmaceutically acceptable salts thereof are selective, competitive inhibitors of HMG-CoA reductase. As such, atorvastatin calcium is a potent lipid lowering compound and is thus useful as a hypolipidemic and/or hypocholesterolemic agent, as well as in the treatment of osteoporosis, BPH, diabetes and Alzheimer's disease. A number of patents have issued disclosing atorvastatin including U.S. Pat. Nos. 4,681,893; 5,273,995 and 5,969,156. Other representative statins include lovastatin, pravastatin, simvastatin and rosuvastatin.

Statin drugs share many features, but also exhibit differences in pharmacologic attributes that may contribute to differences in clinical utility and effectiveness in modifying lipid risk factors for coronary heart disease. (*Clin. Cardiol. Bol.* 26 (Suppl. III), III-32-III-38 (2003)). Accordingly, it would be most beneficial to provide a statin having a combination of desirable properties including (i) potent reversible inhibition of HMG-CoA reductase, (ii) the ability to produce large reductions in LDL-C and non-high-density lipoprotein cholesterol (non-HDL-C), (iii) the ability to increase HDL cholesterol (HDL-C), (iv) relative hydrophilicity, (v) tissue selectivity (e.g., selectivity of effect or uptake in hepatic cells through selective organic ion transport), (vi) optimal pharmacokinetics or systemic bioavailability so as to minimize any potential risk of systemic adverse effects, while at the same time having enough systemic availability so that any pleiotropic effects can be observed in the vasculature with statin treatment, (vii) availability of once a day dosing, (viii) a low potential for drug-drug interactions, (ix) the ability to lower circulating very-low-density-lipoprotein (VLDL) as well as the ability to lower triglyceride levels, (x) prolonged elimination half-life to maximize effectiveness for lowering LDL-C, (xi) absence or minimal metabolism via the cytochrome P450 (CYP) enzyme system (e.g., the CYP3A4 system) so as to minimize any potential risk of drug-drug interactions when statins are given in combination with other drugs, and (xii) reduce levels of C-reactive protein (CRP).

As described below, the present invention relates to compounds and pharmaceutical compositions useful as hypocholesterolemic and hypolipidemic agents. More specifically, the present invention concerns certain potent inhibitors of the enzyme 3-hydroxy-3-methylglutaryl-coenzyme A reductase ("HMG CoA reductase"). The invention further relates to methods of using such compounds and compositions to treat subjects, including humans, suffering from hyperlipidemia, hypercholesterolemia, hypertriglyceridemia, atherosclerosis, Alzheimer's Disease, benign prostatic hypertrophy (BPH), diabetes and osteoporosis.

SUMMARY OF THE INVENTION

The present invention provides a compound of the formula (I):

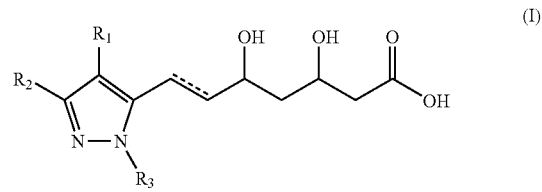

or a pharmaceutically acceptable salt, ester, amide, hydrate, stereoisomer or prodrug thereof, or a pharmaceutically acceptable salt of the prodrug, wherein:

$R_1$ is hydrogen, halogen, $C_1$-$C_7$ alkyl, $C_3$-$C_8$ cycloalkyl, aryl, aralkyl, heteroaryl, or heteroaralkyl; more specifically, $R_1$ is $C_1$-$C_7$ alkyl or $C_3$-$C_8$ cycloalkyl; even more specifically, $R_1$ is isopropyl; where alkyl, cycloalkyl, aryl, aralkyl, heteroaryl, or heteroaralkyl of $R_1$ is optionally substituted as defined for each of these groups below;

$R_2$ is hydrogen, halogen, $C_1$-$C_7$ alkyl, $C_3$-$C_8$ cycloalkyl, aryl, aralkyl, heteroaryl, heteroaralkyl, NC—, $R_{2b}R_{2a}$NCO$(CH_2)_n$—, $R_{2b}R_{2a}$NS(O)$_n$—, $R_{2c}$S(O)$_n$—, $R_{2b}R_{2a}$N$(CH_2)_n$—, $R_{2b}$-J-C(O)NR$_{2a}$(CH$_2$)$_n$—, $R_{2b}$-J-SO$_2$NR$_{2a}$(CH$_2$)$_n$—, $R_{2b}$-J-SONR$_{2a}$(CH$_2$)$_n$, $R^7$OOC(CH$_2$)$_n$—, or $R^7$CO(CH$_2$)$_n$—; more specifically, $R_2$ is $R_{2b}R_{2a}$ NCO(CH$_2$)$_n$—; even more specifically, $R_2$ is $R_{2b}R_{2a}$ NCO—; where alkyl, cycloalkyl, aryl, aralkyl, heteroaryl, or heteroaralkyl of $R_2$ is optionally substituted as defined for each of these groups below;

J is a direct bond, O, or N;

$R_{2a}$ and $R_{2b}$ are each independently hydrogen, $C_1$-$C_{10}$ alkyl, $C_3$-$C_8$ cycloalkyl, aryl, aralkyl, heteroaryl or heteroaralkyl; more specifically, $R_{2a}$ and $R_{2b}$ are each independently hydrogen, $C_1$-$C_7$alkyl, aryl or aralkyl; even more specifically, $R_{2a}$ and $R_{2b}$ are each independently hydrogen, methyl or benzyl; where alkyl, cycloalkyl, aryl, aralkyl, heteroaryl, or heteroaralkyl of $R_{2a}$ and $R_{2b}$ is optionally substituted as defined for each of these groups below;

or $R_{2a}$ and $R_{2b}$ taken together with the nitrogen to which they are attached form a 4-11 member ring optionally containing at least one additional heteroatom selected from O, N and S, said ring being optionally substituted with at least one of aryl, aralkyl, heteroaryl, heteroaralkyl, $C_1$-$C_{10}$ alkyl, $C_3$-$C_8$ cycloalkyl, halogen, $R^7$O—, $R^7$OOC(CH$_2$)$_n$—, $R^7R^8$NCO$(CH_2)_n$—, $R^7O_2$S(CH$_2$)$_n$—, $R^8R^7$NSO$_2$— or NC—;

$R_{2c}$ is aryl, aralkyl, alkyl, heteroaryl, or heteroaralkyl; where aryl, aralkyl, alkyl, heteroaryl, or heteroaralkyl of $R_{2c}$ is optionally substituted as defined for each of these groups below;

$R^7$ and $R^8$ are each independently hydrogen, $C_1$-$C_{12}$ alkyl, aryl or aralkyl; where alkyl, aryl or aralkyl of $R^7$ and $R^8$ is optionally substituted as defined for each of these groups below;

n is 0, 1 or 2; more specifically, n is 0 or 1; even more specifically, n is 0;

$R_3$ is hydrogen, $C_{1-6}$ alkyl, $C_{3-8}$ cycloalkyl, aryl, aralkyl, heteroaryl, or heteroaralkyl; more specifically, $R_3$ is aryl; even more specifically, $R_3$ is phenyl or p-fluorophenyl; where alkyl, cycloalkyl, aryl, aralkyl, heteroaryl, or heteroaralkyl of $R_3$ is optionally substituted as defined for each of these groups below; and — is a bond or is absent.

The present invention provides a compound of the following (3R, 5R) stereospecific formula (Ia):

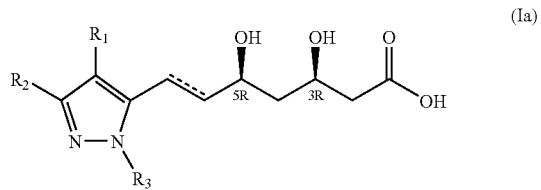

(Ia)

or a pharmaceutically acceptable salt, ester, amide, hydrate, stereoisomer or prodrug thereof, or a pharmaceutically acceptable salt of the prodrug, wherein $R_1$, $R_2$, $R_3$, and — are each as set forth above.

The invention further provides a compound of formula (II):

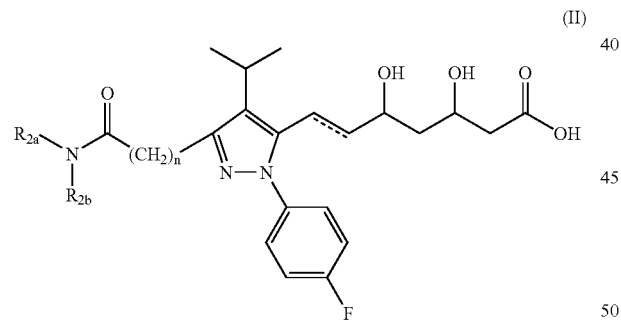

(II)

or a pharmaceutically acceptable salt, ester, amide, hydrate, stereoisomer or prodrug thereof, or a pharmaceutically acceptable salt of the prodrug, wherein $R_{2a}$, $R_{2b}$, n and — are each as set forth above.

The invention further provides a compound of formula (II), as set forth above, wherein $R_{2a}$ is:

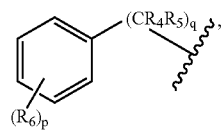

where $R_4$ and $R_5$ are each independently hydrogen or lower alkyl;

q is 0, 1 or 2;

each $R_6$ is independently hydrogen, halogen, alkyl, haloalky, alkoxy, or cyano; and p is 0, 1, 2, 3, 4, or 5;

or a pharmaceutically acceptable salt, ester, amide, hydrate, stereoisomer or prodrug thereof, or a pharmaceutically acceptable salt of the prodrug.

The invention further provides a (3R, 5R) stereospecific compound of formula (IIa):

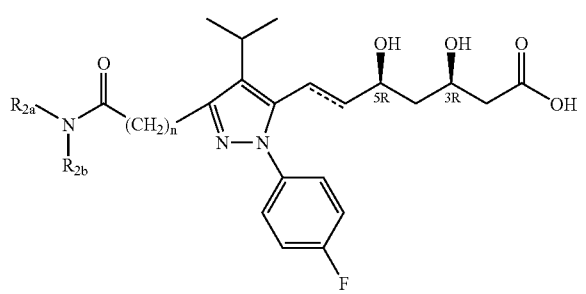

(IIa)

or a pharmaceutically acceptable salt, ester, amide, hydrate, stereoisomer or prodrug thereof, or a 10 pharmaceutically acceptable salt of the prodrug, wherein $R_{2a}$, $R_{2b}$, n and — are each as defined above.

The invention further provides a compound of formula (III):

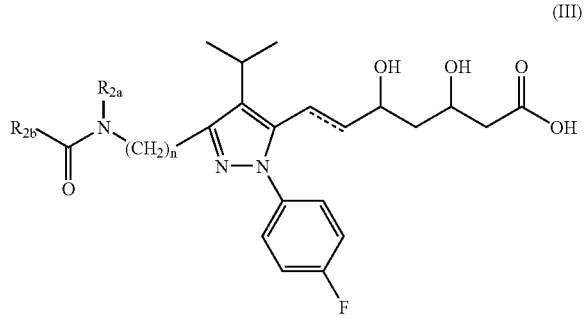

(III)

or a pharmaceutically acceptable salt, ester, amide, hydrate, stereoisomer or prodrug thereof, or a pharmaceutically acceptable salt of the prodrug, wherein $R_{2a}$, $R_{2b}$, n and — are each as defined above.

The invention further provides a (3R, 5R) stereospecific compound of formula (IIIa):

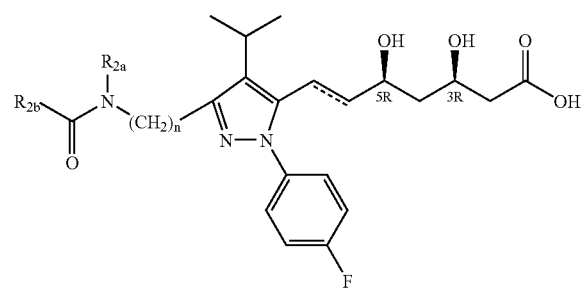

(IIIa)

or a pharmaceutically acceptable salt, ester, amide, hydrate, stereoisomer or prodrug thereof, or a pharmaceutically acceptable salt of the prodrug, wherein $R_{2a}$, $R_{2b}$, n and — are each as defined above.

The invention further provides a compound of formula (IV):

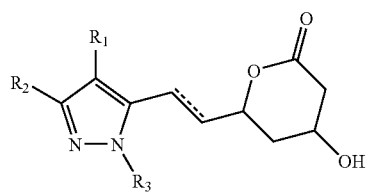

(IV)

or a pharmaceutically acceptable salt, ester, amide, hydrate, stereoisomer or prodrug thereof, or a pharmaceutically acceptable salt of the prodrug, wherein $R_1$, $R_2$, $R_3$ and — are each as defined above.

The invention further provides a stereospecific compound of formula (IVa):

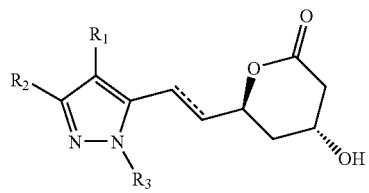

(IVa)

or a pharmaceutically acceptable salt, ester, amide, hydrate, stereoisomer or prodrug thereof, or a pharmaceutically acceptable salt of the prodrug, wherein $R_1$, $R_2$, $R_3$ and — are each as defined above.

The invention further provides a compound of formula (V):

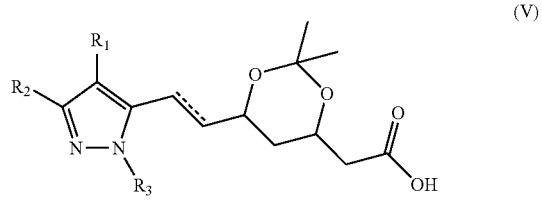

(V)

or a pharmaceutically acceptable salt, ester, amide, hydrate, stereoisomer or prodrug thereof, or a pharmaceutically acceptable salt of the prodrug, wherein $R_1$, $R_2$, $R_3$ and — are each as defined above.

The invention further provides a compound of formula (VI):

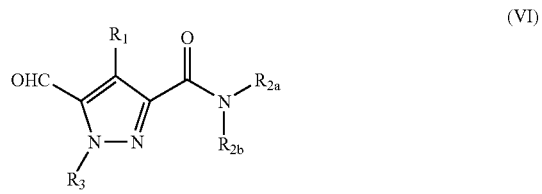

(VI)

wherein $R_1$, $R_{2a}$, $R_{2b}$, and $R_3$ are each as defined above.

The invention further provides a compound of formula (VII):

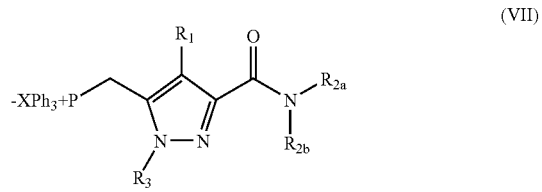

(VII)

wherein $R_1$, $R_{2a}$, $R_{2b}$, $R_3$ are each as defined above, and X is a suitable counteranion; more specifically, X is F, Cl, Br, or I anion; even more specifically, X is Br anion.

The invention further provides a compound selected from the group consisting of:
(3R,5R)-7-[5-benzylcarbamoyl-2-(4-fluoro-phenyl)-4-isopropyl-2H-pyrazol-3-yl]-3,5-dihydroxy-heptanoic acid;
(3R,5R)-7-[2-(4-fluoro-phenyl)-4-isopropyl-5-(2-methyl-benzylcarbamoyl)-2H-pyrazol-3-yl]-3,5-dihydroxy-heptanoic acid;
(3R,5R)-7-[2-(4-fluoro-phenyl)-4-isopropyl-5-(3-methyl-benzylcarbamoyl)-2H-pyrazol-3-yl]-3,5-dihydroxy-heptanoic dihydroxy-heptanoic acid;
(3R,5R)-7-[2-(4-fluoro-phenyl)-4-isopropyl-5-(4-methyl-benzylcarbamoyl)-2H-pyrazol-3-yl]-3,5-dihydroxy-heptanoic acid;
(3R,5R)-7-[2-(4-fluoro-phenyl)-4-isopropyl-5-(2-methyl-benzylcarbamoyl)-2H-pyrazol-3-yl]-3,5-dihydroxy-hept-6-enoic acid;
(3R,5R)-7-[2-(4-fluoro-phenyl)-4-isopropyl-5-(4-methyl-benzylcarbamoyl)-2H-pyrazol-3-yl]-3,5-dihydroxy-hept-6-enoic acid;

(3R,5R)-7-[2-(4-fluoro-phenyl)-4-isopropyl-5-(3-methoxy-benzylcarbamoyl)-2H-pyrazol-3-yl]-3,5-dihydroxy-heptanoic acid;

(3R,5R)-7-[2-(4-fluoro-phenyl)-4-isopropyl-5-(4-methoxy-benzylcarbamoyl)-2H-pyrazol-3-yl]-3,5-dihydroxy-heptanoic acid;

(3R,5R)-7-[2-(4-fluoro-phenyl)-4-isopropyl-5-(3-methoxy-benzylcarbamoyl)-2H-pyrazol-3-yl]-3,5-dihydroxy-hept-6-enoic acid;

(3R,5R)-7-[2-(4-fluoro-phenyl)-4-isopropyl-5-(4-methoxy-benzylcarbamoyl)-2H-pyrazol-3-yl]-3,5-dihydroxy-hept-6-enoic acid;

(3R,5R)-7-[5-(benzyl-methyl-carbamoyl)-2-(4-fluoro-phenyl)-4-isopropyl-2H-pyrazol-3-yl]-3,5-dihydroxy-heptanoic acid;

(3R,5R)-7-[5-[(3-fluoro-benzyl)-methyl-carbamoyl]-2-(4-fluoro-phenyl)-4-isopropyl-2H-pyrazol-3-yl]-3,5-dihydroxy-heptanoic acid;

(3R,5R)-7-[5-[(4-fluoro-benzyl)-methyl-carbamoyl]-2-(4-fluoro-phenyl)-4-isopropyl-2H-pyrazol-3-yl]-3,5-dihydroxy-hept-6-enoic acid;

(3R,5R)-7-{2-(4-fluoro-phenyl)-4-isopropyl-5-[N-methyl-(R)-α-methyl-benzylcarbamoyl]-2H-pyrazol-3-yl}-3,5-dihydroxy-heptanoic acid;

(3R,5R)-7-[2-(4-fluoro-phenyl)-4-isopropyl-5-[(R)-α-methyl-benzylcarbamoyl]-2H-pyrazol-3-yl]-3,5-dihydroxy-heptanoic acid;

(3R,5R)-7-[2-(4-fluoro-phenyl)-4-isopropyl-5-[(S)-α-methyl-benzylcarbamoyl]-2H-pyrazol-3-yl]-3,5-dihydroxy-heptanoic acid;

(3R,5R)-7-[5-(benzyl-methyl-carbamoyl)-2-(4-fluoro-phenyl)-4-isopropyl-2H-pyrazol-3-yl]-3,5-dihydroxy-hept-6-enoic acid;

(3R,5R)-7-[2-(4-fluoro-phenyl)-4-isopropyl-5-[(R)-α-methyl-benzylcarbamoyl]-2H-pyrazol-3-yl]-3,5-dihydroxy-hept-6-enoic acid;

(3R,5R)-7-[2-(4-fluoro-phenyl)-4-isopropyl-5-[(S)-α-methyl-benzylcarbamoyl]-2H-pyrazol-3-yl]-3,5-dihydroxy-hept-6-enoic acid;

(3R,5R)-7-[2-(4-fluoro-phenyl)-4-isopropyl-5-phenethylcarbamoyl-2H-pyrazol-3-yl]-3,5-dihydroxy-heptanoic acid;

(3R,5R)-7-[2-(4-fluoro-phenyl)-4-isopropyl-5-methylcarbamoyl-2H-pyrazol-3-yl]-3,5-dihydroxy-heptanoic acid;

(3R,5R)-7-[5-ethylcarbamoyl-2-(4-fluoro-phenyl)-4-isopropyl-2H-pyrazol-3-yl]-3,5-dihydroxy-heptanoic acid;

(3R,5R)-7-[5-dimethylcarbamoyl-2-(4-fluoro-phenyl)-4-isopropyl-2H-pyrazol-3-yl]-3,5-dihydroxy-heptanoic acid;

7-(5-Benzylcarbamoyl-4-isopropyl-2-(4-fluoro-phenyl)-2H-pyrazol-3-yl)-3R,5R-dihydroxy-heptanoic acid;

7-(5-Benzylcarbamoyl-4-isopropyl-2-(4-fluoro-phenyl)-2H-pyrazol-3-yl)-3R,5R-dihydroxy-heptanoic acid;

3R,5R-Dihydroxy-7-[4-isopropyl-5-(3-methyl-benzylcarbamoyl)-2-(4-fluoro-phenyl)-2H-pyrazol-3-yl]-heptanoic acid;

3R,5R-Dihydroxy-7-[4-isopropyl-5-(4-methyl-benzylcarbamoyl)-2-(4-fluoro-phenyl)-2H-pyrazol-3-yl]-heptanoic acid;

3R,5R-Dihydroxy-7-[4-isopropyl-5-(3-methoxy-benzylcarbamoyl)-2-(4-fluoro-phenyl)-2H-pyrazol-3-yl]-heptanoic acid;

3R,5R-Dihydroxy-7-[4-isopropyl-5-(4-methoxy-benzylcarbamoyl)-2-(4-fluoro-phenyl)-2H-pyrazol-3-yl]-heptanoic acid;

7-[5-(Benzyl-methyl-carbamoyl)-4-isopropyl-2-(4-fluoro-phenyl)-2H-pyrazol-3-yl]-3R,5R-dihydroxy-heptanoic acid;

7-{5-[(3-Fluoro-benzyl)-methyl-carbamoyl]-4-isopropyl-2-(4-fluoro-phenyl)-2H-pyrazol-3-yl}-3R,5R-dihydroxy-heptanoic acid;

7-{5-[(4-Fluoro-benzyl)-methyl-carbamoyl]-4-isopropyl-2-(4-fluoro-phenyl)-2H-pyrazol-3-yl}-3R,5R-dihydroxy-heptanoic acid;

3R,5R-Dihydroxy-7-[4-isopropyl-2-(4-fluoro-phenyl)-5-[(R)-α-methyl-benzylcarbamoyl]-2H-pyrazol-3-yl]-heptanoic acid;

3R,5R-Dihydroxy-7-[4-isopropyl-2-(4-fluoro-phenyl)-5-[(S)-α-methyl-benzylcarbamoyl]-2H-pyrazol-3-yl]-heptanoic acid;

3R,5R-Dihydroxy-7-{4-isopropyl-5-[N-methyl-(R)-α-methyl-benzylcarbamoyl]-2-(4-fluoro-phenyl)-2H-pyrazol-3-yl}-heptanoic acid;

3R,5R-Dihydroxy-7-{4-isopropyl-5-[N-methyl-(R )-α-methyl-benzylcarbamoyl]-2-(4-fluoro-phenyl)-2H-pyrazol-3-yl}-heptanoic acid;

3R,5R-Dihydroxy-7-[4-isopropyl-5-(4-methyl-benzylcarbamoyl)-2-(4-fluoro-phenyl)-2H-pyrazol-3-yl]-hept-6-enoic acid;

3R,5R-Dihydroxy-7-[4-isopropyl-5-(3-methoxy-benzylcarbamoyl)-2-(4-fluoro-phenyl)-2H-pyrazol-3-yl]-hept-6-enoic acid;

3R,5R-Dihydroxy-7-[4-isopropyl-5-(4-methoxy-benzylcarbamoyl)-2-(4-fluoro-phenyl)-2H-pyrazol-3-yl]-hept-6-enoic acid;

3R,5R-Dihydroxy-7-(4-isopropyl-5-methylcarbamoyl-2-(4-fluoro-phenyl)-2H-pyrazol-3-yl)-heptanoic acid;

7-(5-Ethylcarbamoyl-4-isopropyl-2-(4-fluoro-phenyl)-2H-pyrazol-3-yl)-3R,5R-dihydroxy-heptanoic acid;

7-(5-Dimethylcarbamoyl-4-isopropyl-2-(4-fluoro-phenyl)-2H-pyrazol-3-yl)-3R,5R-dihydroxy-heptanoic acid;

7-[5-(Benzyl-methyl-carbamoyl)-4-isopropyl-2-(4-fluoro-phenyl)-2H-pyrazol-3-yl]-3R,5R-dihydroxy-hept-6-enoic acid;

3R,5R-Dihydroxy-7-[4-isopropyl-2-(4-fluoro-phenyl)-5-[(R)-α-methyl-benzylcarbamoyl]-2H-pyrazol-3-yl]-hept-6-enoic acid;

3R,5R-Dihydroxy-7-[4-isopropyl-2-(4-fluoro-phenyl)-5-[(S)-α-methyl-benzylcarbamoyl]-2H-pyrazol-3-yl]-hept-6-enoic acid;

(3R,5R)-7-{2-(4-fluoro-phenyl)-4-isopropyl-5-[methyl-(4-methyl-benzyl)-carbamoyl]-2H-pyrazol-3-yl}-3,5-dihydroxy-heptanoic acid;

(3R,5R)-7-[2-(4-fluoro-phenyl)-4-isopropyl-5-phenylcarbamoyl-2H-pyrazol-3-yl]-3,5-dihydroxy-heptanoic acid;

(3R,5R)-7-[5-(3-fluoro-benzylcarbamoyl)-2-(4-fluoro-phenyl)-4-isopropyl-2H-pyrazol-3-yl]-3,5-dihydroxy-heptanoic acid;

(3R,5R)-7-[5-(4-fluoro-benzylcarbamoyl)-2-(4-fluoro-phenyl)-4-isopropyl-2H-pyrazol-3-yl]-3,5-dihydroxy-heptanoic acid;

(3R,5R)-7-[2-(4-fluoro-phenyl)-4-isopropyl-5-(1-methyl-1-phenyl-ethylcarbamoyl)-2H-pyrazol-3-yl]-3,5-dihydroxy-heptanoic acid;

(3R,5R)-7-[2-(4-fluoro-phenyl)-4-isopropyl-5-(4-methoxymethyl-benzylcarbamoyl)-2H-pyrazol-3-yl]-3,5-dihydroxy-heptanoic acid;

(3R,5R)-7-{2-(4-fluoro-phenyl)-4-isopropyl-5-[(4-methoxy-benzyl)-methyl-carbamoyl]-2H-pyrazol-3-yl}-3,5-dihydroxy-heptanoic acid;

(3R,5R)-7-{2-(4-fluoro-phenyl)-4-isopropyl-5-[methyl-(3-methyl-benzyl)-carbamoyl]-2H-pyrazol-3-yl}-3,5-dihydroxy-heptanoic acid;

(3R,5R)-7-{2-(4-fluoro-phenyl)-4-isopropyl-5-[(3-methoxy-benzyl)-methyl-carbamoyl]-2H-pyrazol-3-yl}-3,5-dihydroxy-heptanoic acid;

(3R,5R)-7-[5-(benzyl-ethyl-carbamoyl)-2-(4-fluoro-phenyl)-4-isopropyl-2H-pyrazol-3-yl]-3,5-dihydroxy-heptanoic acid;

(3R,5R)-7-[5-(benzyl-isopropyl-carbamoyl)-2-(4-fluoro-phenyl)-4-isopropyl-2H-pyrazol-3-yl]-3,5-dihydroxy-heptanoic acid;

(3R,5R)-7-{2-(4-fluoro-phenyl)-4-isopropyl-5-[methyl-(1-phenyl-ethyl)-carbamoyl]-2H-pyrazol-3-yl}-3,5-dihydroxy-heptanoic acid;

(3R,5R)7-[5-(cyclohexylmethyl-carbamoyl)-2-(4-fluoro-phenyl)-4-isopropyl-2H-pyrazol-3-yl]-3,5-dihydroxy-heptanoic acid;

(3R,5R)-7-[2-(4-fluoro-phenyl)-4-isopropyl-5-(1-p-tolyl-ethylcarbamoyl)-2H-pyrazol-3-yl]-3,5-dihydroxy-heptanoic acid;

(3R,5R)-7-[2-(4-fluoro-phenyl)-4-isopropyl-5-(3-methoxymethyl-benzylcarbamoyl)-2H-pyrazol-3-yl]-3,5-dihydroxy-heptanoic acid;

(3R,5R)-7-{2-(4-fluoro-phenyl)-4-isopropyl-5-[1-(3-methoxy-phenyl)-ethylcarbamoyl]-2H-pyrazol-3-yl}-3,5-dihydroxy-heptanoic acid;

(3R,5R)-7-{2-(4-fluoro-phenyl)-4-isopropyl-5-[1-(4-methoxy-phenyl)-ethylcarbamoyl]-2H-pyrazol-3-yl}-3,5-dihydroxy-heptanoic acid;

(3R,5R)-7-{2-(4-fluoro-phenyl)-4-isopropyl-5-[methyl-(3-trifluoromethyl-benzyl)-carbamoyl]-2H-pyrazol-3-yl}-3,5-dihydroxy-heptanoic acid;

(3R,5R)-7-{2-(4-fluoro-phenyl)-4-isopropyl-5-[methyl-(4-trifluoromethyl-benzyl)-carbamoyl]-2H-pyrazol-3-yl}-3,5-dihydroxy-heptanoic acid;

(3R,5R)-7-[2-(4-fluoro-phenyl)-4-isopropyl-5-propylcarbamoyl-2H-pyrazol-3-yl]-3,5-dihydroxy-heptanoic acid;

(3R,5R)-7-[5-(4-dimethylcarbamoyl-benzylcarbamoyl)-2-(4-fluoro-phenyl)-4-isopropyl-2H-pyrazol-3-yl]-3,5-dihydroxy-heptanoic acid;

(3R,5R)-7-{2-(4-fluoro-phenyl)-4-isopropyl-5-[(pyridin-2-ylmethyl)-carbamoyl]-2H-pyrazol-3-yl}-3,5-dihydroxy-heptanoic acid;

(3R,5R)-7-[2-(4-fluoro-phenyl)-5-(2-hydroxy-1-phenyl-ethylcarbamoyl)-4-isopropyl-2H-pyrazol-3-yl]-3,5-dihydroxy-heptanoic acid;

(3R,5R)-7-[2-(4-fluoro-phenyl)-4-isopropyl-5-(morpholine-4-carbonyl)-2H-pyrazol-3-yl]-3,5-dihydroxy-heptanoic acid;

(3R,5R)-7-[2-(4-fluoro-phenyl)-4-isopropyl-5-isopropylcarbamoyl-2H-pyrazol-3-yl]-3,5-dihydroxy-heptanoic acid;

(3R,5R)-7-[5-(cyclohexylmethyl-methyl-carbamoyl)-2-(4-fluoro-phenyl)-4-isopropyl-2H-pyrazol-3-yl]-3,5-dihydroxy-heptanoic acid;

(3R,5R)-7-[5-(cyclopentylmethyl-carbamoyl)-2-(4-fluoro-phenyl)-4-isopropyl-2H-pyrazol-3-yl]-3,5-dihydroxy-heptanoic acid;

(3R,5R)-7-[2-(4-fluoro-phenyl)-5-isobutylcarbamoyl-4-isopropyl-2H-pyrazol-3-yl]-3,5-dihydroxy-heptanoic acid;

(3R,5R)-7-[2-(4-fluoro-phenyl)-4-isopropyl-5-(3-methyl-butylcarbamoyl)-2H-pyrazol-3-yl]-3,5-dihydroxy-heptanoic acid;

(3R,5R)-7-[5-cyclopentylcarbamoyl-2-(4-fluoro-phenyl)-4-isopropyl-2H-pyrazol-3-yl]-3,5-dihydroxy-heptanoic acid;

(3R,5R)-7-[2-(4-fluoro-phenyl)-4-isopropyl-5-(2-phenyl-pyrrolidine-1-carbonyl)-2H-pyrazol-3-yl]-3,5-dihydroxy-heptanoic acid;

(3R,5R)-7-[5-(cyclobutylmethyl-carbamoyl)-2-(4-fluoro-phenyl)-4-isopropyl-2H-pyrazol-3-yl]-3,5-dihydroxy-heptanoic acid;

(3R,5R)-7-[5-[(2,3-difluoro-benzyl)-methyl-carbamoyl]-2-(4-fluoro-phenyl)-4-isopropyl-2H-pyrazol-3-yl]-3,5-dihydroxy-heptanoic acid;

(3R,5R)-7-[5-(cyclopropylmethyl-carbamoyl)-2-(4-fluoro-phenyl)-4-isopropyl-2H-pyrazol-3-yl]-3,5-dihydroxy-heptanoic acid;

(3R,5R)-7-[5-[(2,4-difluoro-benzyl)-methyl-carbamoyl]-2-(4-fluoro-phenyl)-4-isopropyl-2H-pyrazol-3-yl]-3,5-dihydroxy-heptanoic acid;

(3R,5R)-7-{2-(4-fluoro-phenyl)-4-isopropyl-5-[methyl-(4-trifluoromethoxy-benzyl)-carbamoyl]-2H-pyrazol-3-yl}-3,5-dihydroxy-heptanoic acid;

(3R,5R)-7-[5-butylcarbamoyl-2-(4-fluoro-phenyl)-4-isopropyl-2H-pyrazol-3-yl]-3,5-dihydroxy-heptanoic acid;

(3R,5R)-7-[2-(4-fluoro-phenyl)-4-isopropyl-5-(piperidine-1-carbonyl)-2H-pyrazol-3-yl]-3,5-dihydroxy-heptanoic acid;

(3R,5R)-7-{2-(4-fluoro-phenyl)-4-isopropyl-5-[methyl-(3-trifluoromethoxy-benzyl)-carbamoyl]-2H-pyrazol-3-yl}-3,5-dihydroxy-heptanoic acid;

(3R,5R)-7-[5-cyclohexylcarbamoyl-2-(4-fluoro-phenyl)-4-isopropyl-2H-pyrazol-3-yl]-3,5-dihydroxy-heptanoic acid;

(3R,5R)-7-[5-(4-cyano-benzylcarbamoyl)-2-(4-fluoro-phenyl)-4-isopropyl-2H-pyrazol-3-yl]-3,5-dihydroxy-heptanoic acid;

(3R,5R)-7-[5-(3-cyano-benzylcarbamoyl)-2-(4-fluoro-phenyl)-4-isopropyl-2H-pyrazol-3-yl]-3,5-dihydroxy-heptanoic acid;

(3R,5R)-7-[5-(cyclopentylmethyl-methyl-carbamoyl)-2-(4-fluoro-phenyl)-4-isopropyl-2H-pyrazol-3-yl]-3,5-dihydroxy-heptanoic acid;

(3R,5R)-7-{2-(4-fluoro-phenyl)-4-isopropyl-5-[methyl-(2-methyl-benzyl)-carbamoyl]-2H-pyrazol-3-yl}-3,5-dihydroxy-heptanoic acid;

(3R,5R)-7-[5-[(2-fluoro-benzyl)-methyl-carbamoyl]-2-(4-fluoro-phenyl)-4-isopropyl-2H-pyrazol-3-yl]-3,5-dihydroxy-heptanoic acid;

(3R,5R)-7-[5-[(3,4-difluoro-benzyl)-methyl-carbamoyl]-2-(4-fluoro-phenyl)-4-isopropyl-2H-pyrazol-3-yl]-3,5-dihydroxy-heptanoic acid;

(3R,5R)-7-[5-(3-ethoxymethyl-benzylcarbamoyl)-2-(4-fluoro-phenyl)-4-isopropyl-2H-pyrazol-3-yl]-3,5-dihydroxy-heptanoic acid;

(3R,5R)-7-[5-(4-ethyl-benzylcarbamoyl)-2-(4-fluoro-phenyl)-4-isopropyl-2H-pyrazol-3-yl]-3,5-dihydroxy-heptanoic acid;

(3R,5R)-7-{2-(4-fluoro-phenyl)-4-isopropyl-5-[(5-trifluoromethyl-pyridin-2-ylmethyl)-carbamoyl]-2H-pyrazol-3-yl}-3,5-dihydroxy-heptanoic acid;

(3R,5R)-7-{2-(4-fluoro-phenyl)-4-isopropyl-5-[(6-trifluoromethyl-pyridin-3-ylmethyl)-carbamoyl]-2H-pyrazol-3-yl}-3,5-dihydroxy-heptanoic acid;

(3R,5R)-7-{2-(4-fluoro-phenyl)-4-isopropyl-5-[(6-trifluoromethyl-piperidin-3-ylmethyl)-carbamoyl]-2H-pyrazol-3-yl}-3,5-dihydroxy-heptanoic acid;

(3R,5R)-7-[2-(4-fluoro-phenyl)-4-isopropyl-5-(4-isopropyl-benzylcarbamoyl)-2H-pyrazol-3-yl]-3,5-dihydroxy-heptanoic acid;

(3R,5R)-7-[2-(4-fluoro-phenyl)-4-isopropyl-5-(3-phenyl-piperidine-1-carbonyl)-2H-pyrazol-3-yl]-3,5-dihydroxy-heptanoic acid;

(3R,5R)-7-[2-(4-fluoro-phenyl)-4-isopropyl-5-(3-phenyl-piperidine-1-carbonyl)-2H-pyrazol-3-yl]-3,5-dihydroxy-heptanoic acid;

(3R,5R)-7-{2-(4-fluoro-phenyl)-4-isopropyl-5-[(6-methyl-pyridin-3-ylmethyl)-carbamoyl]-2H-pyrazol-3-yl}-3,5-dihydroxy-heptanoic acid;

(3R,5R)-7-[5-ethylcarbamoyl-2-(4-fluoro-phenyl)-4-isopropyl-2H-pyrazol-3-yl]-3,5-dihydroxy-heptanoic acid;

(3R,5R)-7-[2-(4-fluoro-phenyl)-4-isopropyl-5-phenylcarbamoyl-2H-pyrazol-3-yl]-3,5-dihydroxy-hept-6-enoic acid;

(3R,5R)-7-[5-(cyclohexylmethyl-carbamoyl)-2-(4-fluoro-phenyl)-4-isopropyl-2H-pyrazol-3-yl]-3,5-dihydroxy-hept-6-enoic acid;

(3R,5R)-7-[2-(4-fluoro-phenyl)-4-isopropyl-5-propylcarbamoyl-2H-pyrazol-3-yl]-3,5-dihydroxy-hept-6-enoic acid;

(3R,5R)-7-[2-(4-fluoro-phenyl)-4-isopropyl-5-isopropylcarbamoyl-2H-pyrazol-3-yl]-3,5-dihydroxy-hept-6-enoic acid;

(3R,5R)-7-[2-(4-fluoro-phenyl)-5-isobutylcarbamoyl-4-isopropyl-2H-pyrazol-3-yl]-3,5-dihydroxy-hept-6-enoic acid;

(3R,5R)-7-[5-cyclopentylcarbamoyl-2-(4-fluoro-phenyl)-4-isopropyl-2H-pyrazol-3-yl]-3,5-dihydroxy-hept-6-enoic acid;

(3R,5R)-7-[2-(4-fluoro-phenyl)-4-isopropyl-5-(3-methyl-butylcarbamoyl)-2H-pyrazol-3-yl]-3,5-dihydroxy-hept-6-enoic acid;

(3R,5R)-7-[5-(cyclopropylmethyl-carbamoyl)-2-(4-fluoro-phenyl)-4-isopropyl-2H-pyrazol-3-yl]-3,5-dihydroxy-hept-6-enoic acid;

(3R,5R)-7-[5-butylcarbamoyl-2-(4-fluoro-phenyl)-4-isopropyl-2H-pyrazol-3-yl]-3,5-dihydroxy-hept-6-enoic acid;

(3R,5R)-7-{2-(4-fluoro-phenyl)-4-isopropyl-5-[methyl-(3-trifluoromethoxy-benzyl)-carbamoyl]-2H-pyrazol-3-yl}-3,5-dihydroxy-hept-6-enoic acid;

(3R,5R)-7-[5-cyclohexylcarbamoyl-2-(4-fluoro-phenyl)-4-isopropyl-2H-pyrazol-3-yl]-3,5-dihydroxy-hept-6-enoic acid;

(3R,5R)-7-[5-(4-cyano-benzylcarbamoyl)-2-(4-fluoro-phenyl)-4-isopropyl-2H-pyrazol-3-yl]-3,5-dihydroxy-hept-6-enoic acid;

(3R,5R)-7-[5-(3-cyano-benzylcarbamoyl)-2-(4-fluoro-phenyl)-4-isopropyl-2H-pyrazol-3-yl]-3,5-dihydroxy-hept-6-enoic acid;

(3R,5R)-7-[2-(4-fluoro-phenyl)-4-isopropyl-5-methylcarbamoyl-2H-pyrazol-3-yl]-3,5-dihydroxy-hept-6-enoic acid;

(3R,5R)-7-{2-(4-fluoro-phenyl)-4-isopropyl-5-[methyl-(2-methyl-benzyl)-carbamoyl]-2H-pyrazol-3-yl}-3,5-dihydroxy-hept-6-enoic acid;

(3R,5R)-7-{2-(4-fluoro-phenyl)-4-isopropyl-5-[(6-methyl-pyridin-3-ylmethyl)-carbamoyl]-2H-pyrazol-3-yl}-3,5-dihydroxy-hept-6-enoic acid;

7-[5-[(2,6-difluoro-benzyl)-methyl-carbamoyl]-2-(4-fluoro-phenyl)-4-isopropyl-2H-pyrazol-3-yl]-3,5-dihydroxy-heptanoic acid;

7-[5-[(4-fluoro-2-methoxy-benzyl)-methyl-carbamoyl]-2-(4-fluoro-phenyl)-4-isopropyl-2H-pyrazol-3-yl]-3,5-dihydroxy-heptanoic acid;

7-{2-(4-fluoro-phenyl)-4-isopropyl-5-[methyl-(2,3,4-trifluoro-benzyl)-carbamoyl]-2H-pyrazol-3-yl}-3,5-dihydroxy-heptanoic acid;

7-[5-[(3-fluoro-4-methoxy-benzyl)-methyl-carbamoyl]-2-(4-fluoro-phenyl)-4-isopropyl-2H-pyrazol-3-yl]-3,5-dihydroxy-heptanoic acid;

7-{2-(4-fluoro-phenyl)-4-isopropyl-5-[methyl-(2,3,6-trifluoro-benzyl)-carbamoyl]-2H-pyrazol-3-yl}-3,5-dihydroxy-heptanoic acid;

7-[5-[(2,3-difluoro-4-methyl-benzyl)-methyl-carbamoyl]-2-(4-fluoro-phenyl)-4-isopropyl-2H-pyrazol-3-yl]-3,5-dihydroxy-heptanoic acid;

7-[5-[(2,3-difluoro-6-methoxy-benzyl)-methyl-carbamoyl]-2-(4-fluoro-phenyl)-4-isopropyl-2H-pyrazol-3-yl]-3,5-dihydroxy-heptanoic acid;

7-[5-[(3-fluoro-4-methyl-benzyl)-methyl-carbamoyl]-2-(4-fluoro-phenyl)-4-isopropyl-2H-pyrazol-3-yl]-3,5-dihydroxy-heptanoic acid;

7-[5-[(4-fluoro-3-methyl-benzyl)-methyl-carbamoyl]-2-(4-fluoro-phenyl)-4-isopropyl-2H-pyrazol-3-yl]-3,5-dihydroxy-heptanoic acid;

7-[5-[(2,3-difluoro-4-methoxy-benzyl)-methyl-carbamoyl]-2-(4-fluoro-phenyl)-4-isopropyl-2H-pyrazol-3-yl]-3,5-dihydroxy-heptanoic acid;

7-[5-[(2-fluoro-3-methyl-benzyl)-methyl-carbamoyl]-2-(4-fluoro-phenyl)-4-isopropyl-2H-pyrazol-3-yl]-3,5-dihydroxy-heptanoic acid;

7-{2-(4-fluoro-phenyl)-4-isopropyl-5-[methyl-(2,3,5-trifluoro-benzyl)-carbamoyl]-2H-pyrazol-3-yl}-3,5-dihydroxy-heptanoic acid;

7-[5-[(3-fluoro-2-methoxy-benzyl)-methyl-carbamoyl]-2-(4-fluoro-phenyl)-4-isopropyl-2H-pyrazol-3-yl]-3,5-dihydroxy-heptanoic acid;

7-[5-[(2-fluoro-3-methoxy-benzyl)-methyl-carbamoyl]-2-(4-fluoro-phenyl)-4-isopropyl-2H-pyrazol-3-yl]-3,5-dihydroxy-heptanoic acid;

7-[5-[(3-fluoro-2-methyl-benzyl)-methyl-carbamoyl]-2-(4-fluoro-phenyl)-4-isopropyl-2H-pyrazol-3-yl]-3,5-dihydroxy-heptanoic acid; and (3R, 5R)-7-[2-(4-Fluoro-phenyl)-4-isopropyl-5-(2-phenyl-piperidine-1-carbonyl)-2H-pyrazol-3yl]-3,5-dihydroxy-heptanoic acid; or a pharmaceutically acceptable salt, ester, amide or prodrug thereof, or a pharmaceutically acceptable salt of the prodrug.

The invention further provides a compound selected from the group consisting of:

1-(4-Fluoro-phenyl)-5-[2-(4-hydroxy-6-oxo-tetrahydro-pyran-2-yl)-ethyl]-4-isopropyl-1H-pyrazole-3-carboxylic acid (3-fluoro-benzyl)-methyl-amide;

1-(4-Fluoro-phenyl)-5-[2-(4-hydroxy-6-oxo-tetrahydro-pyran-2-yl)-ethyl]-4-isopropyl-1H-pyrazole-3-carboxylic acid benzyl-methyl-amide; and 1-(4-Fluoro-phenyl)-5-[2-(4-hydroxy-6-oxo-tetrahydro-pyran-2-yl)-ethyl]-4-isopropyl-1H-pyrazole-3-carboxylic acid 4-methyl-benzylamide; or a pharmaceutically acceptable salt, ester, amide or prodrug thereof, or a pharmaceutically acceptable salt of the prodrug.

The invention further provides a pharmaceutical composition comprising a compound of the invention and a pharmaceutically acceptable carrier, diluent, solvent or vehicle.

The invention further provides a combination of a compound of the invention and another pharmaceutically active agent, each as described herein. A pharmaceutical composition comprising the aforementioned combination and a pharmaceutically acceptable carrier, diluent, solvent or vehicle, each as described herein, is also provided by the invention.

The invention further provides a method of preparation of a compound, pharmaceutical composition or combination of the invention, each as described herein.

The invention still further provides a method of treating a subject suffering from hyperlipidemia, hypercholesterolemia, hypertriglyceridemia, atherosclerosis, Alzheimer's Disease, benign prostatic hypertrophy (BPH), diabetes and osteoporosis comprising administering a therapeutically effective amount of at least one compound, pharmaceutical composition or combination of the invention, each as described herein, to the subject in need thereof.

The invention still further provides the use of a compound, pharmaceutical composition, or combination of the invention for treating a subject suffering from hyperlipidemia, hypercholesterolemia, hypertriglyceridemia, atherosclerosis, Alzheimer's Disease, benign prostatic hypertrophy (BPH), diabetes and osteoporosis.

The invention still further provides the use of a compound, pharmaceutical composition, or combination of the invention in the preparation of a medicament for the treatment of a subject suffering from hyperlipidemia, hypercholesterolemia, hypertriglyceridemia, atherosclerosis, Alzheimer's Disease, benign prostatic hypertrophy (BPH), diabetes and osteoporosis.

The invention also provides a process comprising the steps of:

(a) reacting a hydroxyl compound VIII:

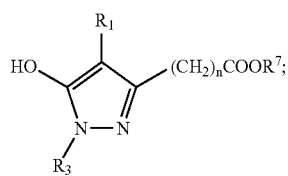

(VIII)

under conditions sufficient to form a compound IX:

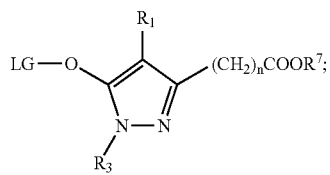

(IX)

(b) reacting a compound IX under conditions sufficient to form a compound X:

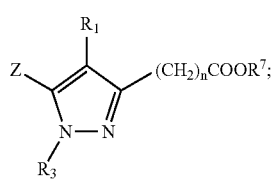

(X)

(c) reacting a compound X under conditions sufficient to form a compound XI:

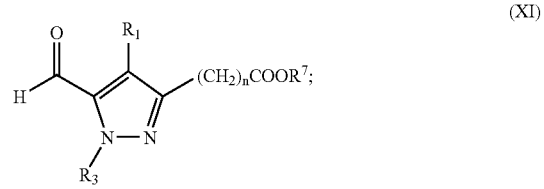

(XI)

(d) reacting a compound XI under conditions sufficient to form a compound XII:

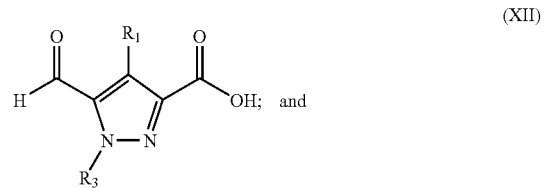

(XII)

(e) reacting a compound XII under conditions sufficient to form a compound XIII:

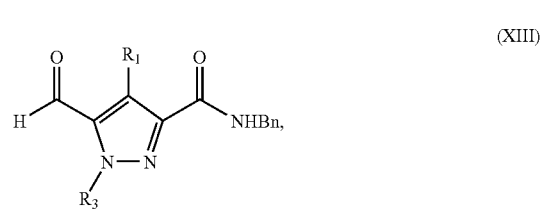

(XIII)

wherein for steps (a)-(e), $R_1$, $R_3$, n, $R^7$ are each as defined herein, and LG-O— together is a leaving group; and Z is R''' or R''''CX'=CX''Y where R''' is alkenyl;

R'''', X' and X'' are each hydrogen, alkyl, alkenyl, aryl, heteroaryl, or alkenyl substituent;

Y is either a direct bond or a linker group; and wherein the non-hydrogen groups of R''', R'''', X', X'', or Y are optionally substituted as defined herein.

The invention further provides a process comprising the steps of:

(a) reacting a compound XIV:

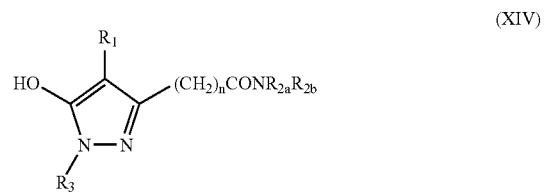

(XIV)

under conditions sufficient to form a compound XV:

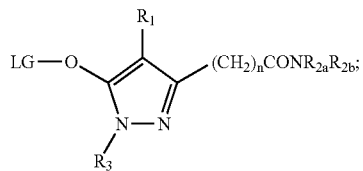

(b) reacting a compound XV under conditions sufficient to form a compound XVI:

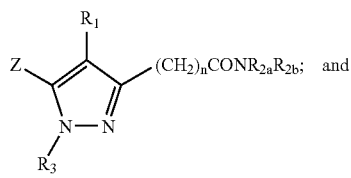

(c) reacting a compound XVI under conditions sufficient to form a compound XVII:

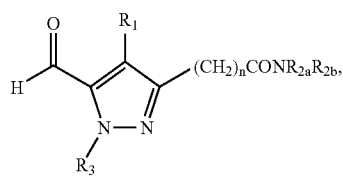

wherein for steps (a)-(c), $R_1$, $R_3$, $R_{2a}$, $R_{2b}$, and n are each as defined herein and LG-O— together is a leaving group; and Z is R''' or R''''CX'=CX''Y where R''' is alkenyl;

R'''', X' and X'' are each hydrogen, alkyl, alkenyl, aryl, heteroaryl, or alkenyl substituent;

Y is either a direct bond or a linker group; and wherein the non-hydrogen groups of R''', R'''', X', X'', or Y are optionally substituted as defined herein.

DETAILED DESCRIPTION OF THE INVENTION
DEFINITIONS

Unless indicated otherwise, the following terms are defined as follows:

The article "a" or "an" as used herein refers to both the singular and plural form of the object to which it refers.

The term "alkyl" as used herein refers to an optionally substituted a straight or branched hydrocarbon of from 1 to 12 carbon atoms and includes, for example, methyl, ethyl, n-propyl, isopropyl, n-butyl, sec-butyl, isobutyl, tert-butyl, n-pentyl, n-hexyl, and the like. The alkyl group may also be optionally substituted with one or more of the substituents selected from cycloalkyl, lower alkoxy, lower thioalkoxy, —O(CH$_2$)O$_2$CF$_3$, —O-aryl, aryl, heteroaryl, halogen, haloalkyl, nitro, cyano, =O, =S, —OH, —SH, —CF$_3$, —CO$_2$H, —CO$_2$C$_1$-C$_6$ alkyl, —NR'R'', —NR'SO$_2$R'', —NR'CONR'R'', or —CONR'R'' where R' and R'' are independently H, alkyl, cycloalkyl, alkenyl, alkynyl, aryl, aralkyl, heteroaryl, heteroaralkyl, or joined together to form a 4-7 member ring optionally containing at least one additional heteroatom selected from N, O and S; or N, R' and R'' taken together form a 4-7 member ring optionally containing at least one additional heteroatom selected from N, O and S.

The term "lower alkyl" as used herein refers to a subset of alkyl which means an optionally substituted straight or branched hydrocarbon radical having from 1 to 7 carbon atoms and includes, for example, methyl, ethyl, n-propyl, isopropyl, n-butyl, sec-butyl, isobutyl, tert-butyl, n-pentyl, n-hexyl, n-heptyl and the like. Alternatively, lower alkyl is referred to as "C$_1$-C$_7$ alkyl." The lower alkyl group may also be optionally substituted with at least one of the substituents recited for the term "alkyl".

The term "alkenyl" as used herein means an optionally substituted straight or branched hydrocarbon radical from 2 to 12 carbon atoms having at least one double bond and includes, for example, ethenyl, 1-propenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like. The alkenyl group may be optionally substituted with at least one of the substituents recited for the term "alkyl".

The term "alkynyl" as used herein means an optionally substituted straight or branched hydrocarbon radical of 2 to 12 carbon atoms having at least one triple bond and includes, for example, 3-propynyl, 1-butynyl, 3-butynyl, 1-pentynyl, 3-pentynyl, 3-methyl-3-butynyl, 1-hexynyl, 3-hexynyl, 3-hexynyl, 3-heptynyl, 1-octynyl, 1-nonynyl, 1-decynyl, 1-undecynyl, 1-dodecynyl, and the like. The alkynyl group may be optionally substituted with at least one of the substituents recited for the term "alkyl".

The term "alkylene" as used herein refers to an optionally substituted divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene group may be optionally substituted with one or more of the substituents selected from lower alkyl, lower alkoxy, lower thioalkoxy, —O(CH$_2$)O$_2$CF$_3$, halogen, haloalkyl, nitro, cyano, =O, =S, —OH, —SH, —CF$_3$, —CO$_2$H, —CO$_2$C$_1$-C$_6$ alkyl, —NR'R'', or —CONR'R'', where R' and R'' are independently H, alkyl, cycloalkyl, alkenyl, alkynyl, aryl, aralkyl, heteroaryl, or heteroaralkyl; or N, R' and R'' taken together form a 4-7 member ring optionally containing at least one additional heteroatom selected from N, O and S. Useful alkylene groups have from 1 to 6 carbon atoms (C$_1$-C$_6$ alkylene). Examples include, but are not limited to, methylene (-CH$_2$-), ethylene (—CH$_2$CH$_2$—), propylene (—(CH$_2$)$_3$—), and the like.

The term "halogen" or "halo" as used herein refers to fluorine or fluoro, chlorine or chloro, bromine or bromo and iodine or iodo.

The term "haloalkyl" as used herein refers to an alkyl group where one or more of the hydrogens has been replaced by a halogen or halo group each as defined herein.

The term "heteroatom" as used herein represents oxygen, nitrogen, or sulfur (O, N, or S) as well as sulfoxyl or sulfonyl (SO or SO$_2$) unless otherwise indicated.

The term "hydrocarbon chain" as used herein refers to an optionally substituted straight hydrocarbon of from 2 to 12 carbon atoms. The hydrocarbon chain is optionally substituted with one or more substituents selected from lower alkyl, lower alkoxy, lower thioalkoxy, —O(CH$_2$)O$_2$CF$_3$, halogen, nitro, cyano, =O, =S, —OH, —SH, —CF$_3$, —CO$_2$H, —CO$_2$C$_1$-C$_6$ alkyl, —NR'R'' or —CONR'R'', where R' and R" are independently H, alkyl, cycloalkyl, alkenyl, alkynyl, aryl, aralkyl, heteroaryl, or heteroaralkyl; or N, R' and R" taken together form a 4-7 member ring optionally containing at least one additional heteroatom selected from N, O and S.

The terms "lower alkoxy" and "lower thioalkoxy" as used herein refers to —O-alkyl or —S-alkyl of from 1 to 7 carbon atoms as defined above for "lower alkyl."

The term "aryl" as used herein refers to a $C_5$-$C_{14}$ mono-, bi- or polycarbocyclic aromatic ring system which is optionally substituted by at least one substituent selected from lower alkyl, lower alkoxy, lower thioalkoxy, halogen, —O($CH_2$)$O_2CF_3$, —Oaryl, —$OSO_2R'$, nitro, cyano —OH, —SH, —$CF_3$, —$CO_2H$, —$CO_2(C_1$-$C_6)$alkyl, —NR'R", —NR'$SO_2$R", —NR'CONR'R", —$SO_{1-2}$alkyl, $SO_{1-2}$aryl, —$SO_2$NR'R", or —CONR'R", where R' and R" are independently H, alkyl, cycloalkyl, alkenyl, alkynyl, aryl, aralkyl, heteroaryl, heteroaralkyl or joined together to form a 4-7 member ring optionally containing at least one additional heteroatom selected from N, O and S; or N, R' and R" taken together form a 4-7 member ring optionally containing at least one additional heteroatom selected from N, O and S. Examples include, but are not limited to, phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, and the like.

The term "aralkyl" as used herein means aryl, as defined above, attached to an alkyl group, as defined above. Linkage to the rest of the molecule may be through either the aryl or alkyl portion of the aralkyl moiety. The aralkyl group may be optionally substituted by at least one of the substituents recited above for "alkyl" and "aryl". Examples of aralkyl include, but are not limited to, benzyl, tolyl, and the like.

The term "heteroaryl" as used herein refers to an aryl group, as defined above, containing one or more heteroatoms, as defined above. The heteroaryl may be optionally substituted with at least one of the substituents recited above for "aryl". Examples of heteroaryl include, but are not limited to thienyl, furanyl, pyrrolyl, pyridyl, pyrimidyl, imidazoyl, pyrazinyl, oxazolyl, thiazolyl, benzothienyl, benzofuranyl, indolyl, quinolinyl, isoquinolinyl, quinazolinyl, 1-imidazolyl, 2-imidazolyl, 4-imidazolyl, 5-imidazolyl, 1-pyrazolyl, 3-pyrazolyl, 4-pyrazolyl, 5-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 1-triazolyl, 3-triazolyl, 5-triazolyl, 1-tetrazolyl, 2-tetrazolyl, 3-tetrazolyl, 2-pyrazinyl, 2-pyrimidinyl, 4-pyrimidinyl, 5-pyrimidinyl, indolizinyl, isoindolyl, benzofuranyl, benzothienyl, benzoxazolyl, benzimidazolyl, quinolinyl, isoquinolinyl, quinazolinyl, 1-indolyl, 2-indolyl, 3-indolyl, 4-indolyl, 5-indolyl, 6-indolyl, 7-indolyl, 1-indolizinyl, 2-indolizinyl, 3-indolizinyl, 5-indolizinyl, 6-indolizinyl, 7-indolizinyl, 8-indolizinyl, 1-isoindolyl, 2-isoindolyl, 3-isoindolyl, 4-isoindolyl, 5-isoindolyl, 6-isoindolyl, 7-isoindolyl, 2-benzothienyl, 3-benzothienyl, 4-benzothienyl, 5-benzothienyl, 6-benzothienyl, 7-benzothienyl, 2-benzoxazolyl, 4-benzoxazolyl, 5-benzoxazolyl, 6-benzoxazolyl, 7-benzoxazolyl, 1-benzimidazolyl, 2-benzimidazolyl, 4-benzimidazolyl, 5-benzimidazolyl, 6-benzimidazolyl, 7-benzimidazolyl, 2-quinolinyl, 3-quinolinyl, 4-quinolinyl, 5-quinolinyl, 6-quinolinyl, 7-quinolinyl, 8-quinolinyl, 1-isoquinolinyl, 3-isoquinolinyl, 4-isoquinolinyl, 5-isoquinolinyl, 6-isoquinolinyl, 7-isoquinolinyl, 8-isoquinolinyl, and the like.

The term heteroaralkyl, as used herein refers to heteroaryl, as defined above, attached to an alkyl group, as defined above. Linkage to the rest of the molecule can be either through the heteroaryl or the alkyl portion of the heteroaralkyl moiety. The heteroaralkyl may be optionally substituted with at least one of those substituents recited above for "alkyl" and "heteroaryl".

The term "heterocycle" as used herein refers to an optionally substituted saturated mono-, bi- or polycyclic ring containing one or more heteroatoms selected from N, O, and S. The heterocycle may be optionally substituted with at least one of those substituents recited above for "alkylene". Examples of suitable heterocycles include, but are not limited to, piperidinyl, pyrrolidinyl, 1-piperazinyl, 2-piperazinyl, 2-morpholinyl, 3-morpholinyl, 4-morpholinyl, piperazinyl, azetidinyl, aziridinyl, , thietanyl, oxetaryl, and the like.

The term "ring" as used herein includes heteroaryl, heterocycle, cycloalkyl or aryl, each as defined above, and further includes fused, monocyclic, bicyclic, and polycyclic permutations thereof.

The term "cycloalkyl" as used herein refers to an optionally substituted saturated cyclic $C_3$-$C_{12}$ alkyl group, where alkyl is as defined above. Examples of suitable cycloalkyl groups include, but are not limited to, cyclopropyl, cyclobutyl, cyclopentyl, cyclohexyl, cycloheptyl, cyclooctyl, decalinyl, norpinanyl, or adamantyl. The cycloalkyl ring may be optionally substituted by with at least one of those substituents recited above for "alkyl" or "alkylene". Examples of substituted cycloalkyl groups include, but are not limited to, fluorocyclopropyl, 2-iodocyclobutyl, 2,3-dimethylcyclopentyl, 2,2-dimethoxycyclohexyl, 3-phenylcyclopentyl, and the like.

The term "treating" or "treatment" refers to curative, palliative and prophylactic treatment, including reversing, ameliorating, alleviating, inhibiting the progress of, or preventing the disorder or condition to which such term applies, or one or more symptoms of such disorder or condition.

The term "stereoisomer" as used herein refers to both geometric (e.g., cis and trans isomers) and/or optical isomers (e.g., R and S enantiomers) of a compound of the invention. Racemic, enantiomeric, diastereomeric and epimeric mixtures of such isomers are contemplated by the present invention.

When a bond to a substituent is shown to cross the bond(s) connecting 2 atoms in a ring, then such substituent may be bonded to any atom in the ring, provided the atom will accept the substituent without violating its valency. When there appears to be several atoms of the substituent that may bond to the ring atom, then it is the first atom of the listed substituent that is attached to the ring, unless indicated otherwise.

When a bond is represented by a line such as "—" this is meant to represent that the bond may be absent or present provided that the resultant compound is stable and of satisfactory valency. If an asymmetric carbon is created by such a bond, a particular stereochemistry is not to be implied.

Unless indicated otherwise, "compound of the invention" or "compounds of the invention" includes the compound itself as well as its pharmaceutically acceptable salt, ester, amide, hydrate, stereoisomer or prodrug thereof, or a pharmaceutically acceptable salt of the prodrug, as well as other embodiments described herein.

As used herein, the following terms have the meanings given: RT or rt means room temperature. MP means melting point. MS means mass spectroscopy. TLC means thin layer chromatography. [S]at. means saturated. [C]onc. means concentrated. TBIA means [(4R,6R)-6-(2-Amino-ethyl)-2,2-dimethyl-[1,3]dioxan-4-yl]-acetic acid tert-butyl ester. DCM means dichloromethane, which is used interchangeably with methylene chloride. NBS means N-Bromosuccinimide. "h" means hour. "v/v" means volume ratio or "volume per volume". "$R_f$" means retention factor. "$Tf_2O$" or "TfO" means triflic anhydride or $C(F)_3S(O)_2OS(O)_2C(F)_3$. $Ac_2O$ means acetic anhydride. "[T]rifluorotol." Or "TFT" means trifluorotoluene "DMF" means dimethylformamide. "DCE" means dichloroethane. "Bu" means butyl. "Me" means methyl. "Et" means ethyl. "DBU" means 1,8-Diazabicyclo-[5.4.0]undec-7-ene. "TBS" means "TBDMS" or tert-Butyldimethylsilyl. "DMSO" means dimethyl sulfoxide. "TBAF" means tetrabutylammonium fluoride. THF means tetrahydrofuran. NBuli or Buli means n-butyl lithium. TFA means trifluoroacetic acid. i-Pr means isopropyl. [M]n means minutes. ml or mL means milliliter. "M" or "m" means molar. "Bn" means benzyl. "PyBOP" means bromo-tris-pyrrolidino-phosphonium hexafluorophosphate. "OtBu" means t-butoxy. "Ts" or "Tosyl" means p-toluenesulfonyl. "PS-DIEA" means polystyrene-bound diisopropylethylamine. "PS-NCO" means polystyrene-bound isocyanate resin. "Ph" means phenyl. As used herein, "hydrogenolysis" means the cleaving of a chemical bond by hydrogen. "EDCl" or "EDC" means 1-(3-dimethylaminopropyl)-3-ethylcarbondiimide hydrochloride. "NMP" means 1-methyl-2-pyrrolidinone.

The term "patient" or "subject" means all mammals including humans. Examples of patients or subjects include humans, cows, dogs, cats, goats, sheep, pigs, and rabbits.

A "therapeutically effective amount" is an amount of a compound of the present invention that when administered to a patient treats a symptom of hyperlipidemia, hypercholesterolemia, hypertriglyceridemia, atherosclerosis, Alzheimer's Disease, benign prostatic hypertrophy (BPH), diabetes and osteoporosis. As would be understood by one of skill in the art, a "therapeutically effective amount" will vary from subject to subject and will be determined on a case by case basis. Factors to consider include, but are not limited to, the subject being treated, weight, health, compound administered, etc.

The term "under conditions sufficient" as used herein refers to those reaction conditions know in the art that would enable the transformation of one compound to the next.

The term "a pharmaceutically acceptable salt, ester, amide, hydrate, stereoisomer or prodrug" as used herein refers to those acid addition salts, base addition salts, esters, amides, hydrates, stereoisomers, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "a pharmaceutically acceptable salt" refers to the relatively non-toxic, inorganic and organic acid or base addition salts of compounds of the invention. These salts can be prepared in situ during the final isolation and purification of the compounds or by separately reacting the purified compound in its free form with a suitable organic or inorganic acid or base and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to,ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.,* 1977;66:1-19, which is incorporated herein by reference.) The free base form may be regenerated by contacting the salt form with a base. While the free base may differ from the salt form in terms of physical properties, such as solubility, the salts are equivalent to their respective free bases for the purposes of the present invention.

Examples of pharmaceutically acceptable, non-toxic esters of the compounds of the invention include $C_1$-$C_6$ alkyl esters wherein the alkyl group is a straight or branched chain. Acceptable esters also include $C_5$-$C_7$ cycloalkyl esters as well as aralkyl esters such as, but not limited to, benzyl. $C_1$-$C_4$ alkyl esters are preferred. Esters of the compounds of the present invention may be prepared according to conventional methods.

Examples of pharmaceutically acceptable, non-toxic amides of the compounds of the invention include amides derived from ammonia, primary ($C_1$-$C_6$)alkyl amines and secondary di-($C_1$-$C_6$)alkyl amines wherein the alkyl groups are straight or branched chain. In the case of secondary amines, the amine may also be in the form of a 5-or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods.

"Prodrugs" are intended to include any covalently bonded carrier which releases the active parent drug according to Formulae I, Ia, II, IIa, III, IIIa, IV, and V in vivo. Further, the term "prodrug" refers to compounds that are transformed in vivo to yield the parent compound of the above formulae, for example, by hydrolysis in blood. A thorough discussion is provided in T. Higuchi and V. Stella, "Pro-drugs as Novel Delivery Systems,"Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include, but are not limited to, acetates, formates, benzoate derivatives of alcohols, and amines present in compounds of the invention.

In some situations, compounds may exist as tautomers. All tautomers of a compound of the invention are encompassed by the present invention.

Certain compounds of the present invention can exist in unsolvated form as well as solvated form including hydrated form. In general, the solvated form including hydrated form is equivalent to the unsolvated form and is intended to be encompassed within the scope of the present invention.

Certain of the compounds of the present invention possess one or more chiral centers and each center may exist in the R or S configuration. For example, compounds of formulae (Ia), (IIa), and (IIIa) are shown with a (3R, 5R) configuration. Also envisioned are compounds having a (3S, 5S), (3S, 5R) or (3R, 5S). If a compound of the invention further contains another chiral center(s), then that center(s) could independently have either an R or S configuration. The present invention includes all diastereomeric, enantiomeric, and epimeric forms as well as the appropriate mixtures thereof. Such stereoisomers may be obtained, if desired, by methods known in the art including, for example, the separation of stereoisomers by chiral chromatographic columns and by chiral synthesis. Additionally, the compounds of the present invention may exist as geometric isomers. The present invention includes all cis, trans, syn, anti, entgegen (E), and zusammen (Z) isomers as well as the appropriate mixtures thereof.

The compounds of the present invention are suitable to be administered to a patient or subject for the treatment of hyperlipidemia, hypercholesterolemia, hypertriglyceridemia, atherosclerosis, Alzheimer's Disease, benign prostatic hypertrophy (BPH), diabetes and osteoporosis. The compounds of the present invention can be administered to a patient/subject alone, or another compound of the invention, or as part of a pharmaceutical composition.

A pharmaceutical composition of the invention contains at least one compound of the invention and at least one pharmaceutically acceptable carrier, diluent, solvent or vehicle. The pharmaceutically acceptable carrier, diluent, solvent or vehicle may be any such carrier known in the art including those described in, for example, Remington's Pharmaceutical Sciences, Mack Publishing Co., (A. R. Gennaro edit. 1985). A pharmaceutical composition of the invention may be prepared by conventional means known in the art including, for example, mixing at least one compound of the invention with a pharmaceutically acceptable carrier.

A composition of the invention can be administered to a patient/subject either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain additives such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one (a) inert customary excipient (or carrier) such as sodium citrate or dicalcium phosphate; (b) fillers or extenders, as for example, starches, lactose, sucrose, glucose, mannitol, and silicic acid; (c) binders, as for example, carboxymethylcellulose, alignates, gelatin, polyvinylpyrrolidone, sucrose, and acacia; (d) humectants, as for example, glycerol; (e) disintegrating agents, as for example, agar-agar, calcium carbonate, potato or tapioca starch, alginic acid, certain complex silicates, and sodium carbonate; (f) solution retarders, as for example paraffin; (g) absorption accelerators, as for example, quaternary ammonium compounds; (h) wetting agents, as for example, cetyl alcohol and glycerol monostearate; (i) adsorbents, as for example, kaolin and bentonite; and (j) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include additives, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary from patient to patient. For example, the dosage can depend on a numbers of factors including the requirements of the patient, the severity of the condition being treated, and the pharmacological activity of the compound being used. The determination of optimum dosages for a particular patient is well known to those skilled in the art.

The compounds of the invention, as described herein, may be used either alone or in combination with another pharmaceutical agent described herein, in the treatment of the following diseases/conditions: dyslipidemia, hypercholesterolemia, hypertriglyceridemia, atherosclerosis, peripheral vascular disease, cardiovascular disorders, angina, ischemia, cardiac ischemia, stroke, myocardial infarction, reperfusion injury, angioplastic restenosis, hypertension, diabetes and vascular complications of diabetes, obesity, unstable angina pectoris, Alzheimer's Disease, BPH, osteoporosis, cerebrovascular disease, coronary artery disease, ventricular dysfunction, cardiac arrhythmia, pulmonary vascular disease, renal-vascular disease, renal disease, vascular hemostatic disease, autoimmune disorders, pulmonary disease, sexual dysfunction, cognitive dysfunction, cancer, organ transplant rejection, psoriasis, endometriosis, and macular degeneration. A combination of the invention may be part of a pharmaceutical composition further containing a pharmaceutically active carrier, diluent, solvent or vehicle, each as described herein.

Examples of a suitable pharmaceutically active agent include a CETP inhibitor, a PPAR-activator, an MTP/Apo B secretion inhibitor, a cholesterol absorption inhibitor, HDL-cholesterol raising agent, triglyceride lowering agent, a cholesterol synthesis inhibitor, a cholesterol modulating agent, a fibrate, niacin, an ion-exchange resin, an antioxidant, an ACAT inhibitor, or bile acid sequestrant; an anti-hypertensive agent; an acetylcholine esterase inhibitor, an anti-diabetic compound, an anti-obesity compound, a thyromimetic agent, an anti-resorptive agent, an anti-osteoporosis agent, an anti-hypertensive agent, or a drug for the treatment of Alzheirner's disease. Specific examples of each of these agents include those known in the art as well as those specificed below.

In combination therapy treatment, both the compounds of the invention and the other drug therapies are administered to mammals by conventional methods. The following discussion more specifically describes the various combination aspects of this invention.

Any cholesterol absorption inhibitor known in the art with the ability of a compound to prevent cholesterol contained within the lumen of the intestine from entering into the intestinal cells and/or passing from within the intestinal cells into the blood stream may be used. Such cholesterol absorption inhibition activity is readily determined according to standard assays (e.g., J. Lipid Res. (1993) 34: 377-395). Examples include, but are not limited to, ZETIA™ as well as the cholesterol absorption inhibitors described in WO 94/00480.

Any cholesterol ester transfer protein ("CETP") inhibitor known in the art that inhibits the transfer of cholesteryl ester and triglyceride between lipoprotein particles, including high density lipoproteins (HDL), low density lipoproteins (LDL), very low density lipoproteins (VLDL), and chylomicrons may be used. The effect of a CETP inhibitor on lipoprotein profile is believed to be anti-atherogenic. Such inhibition may be determined by means known in the art (e.g., Crook et al. Arteriosclerosis 10, 625, 1990; U.S. Pat. No. 6,140,343). Examples of suitable CETP inhibitors include, but are not limited to, those described in U.S. Pat. Nos. 6,197,786, 6,723, 752 and 6,723,753. Additional examples of useful CETP inhibitors include the following compounds: [2R,4S]4-[(3,5-bis-trifluoromethyl-benzyl)-methoxycarbonyl-amino]-2-ethyl-6-trifluoromethyl-3,4-dihydroxycarbonyl-amino]-2-ethyl-6-trifluoromethyl-3,4-dihydro-2H-quinoline-1-carboxylic acid ethyl ester (Torcetrapib™), and 3-{[3-(4-Chloro-3-ethyl-phenoxy)-phenyl]-[3-(1,1,2,2-tetrafluoro-ethoxy)-benzyl]-amino}-1,1,1-trifluoro-propan-2-ol. To address the poor solubility of many of the CETP inhibitors, an appropriate dosage form such as one comprising (1) a solid amorphous dispersion comprising a cholesteryl ester transfer protein (CETP) inhibitor and an acidic concentration-enhancing polymer; and (2) an acid-sensitive HMG-CoA reductase inhibitor, may be necessary. This dosage form is more fully described in U.S. Ser. No. 10/739,567.

Any peroxisome proliferator activated receptor ("PPAR") activator known in the art that activates or otherwise interacts with a human PPAR may be used. Three mammalian PPARs have been isolated and termed PPAR-alpha, PPAR-gamma, and PPAR-beta (also known as NUC1 or PPAR-delta). These PPARs regulate expression of target genes by binding to DNA sequence elements, termed PPAR response elements. These elements have been identified in the enhancers of a number of genes encoding proteins that regulate lipid metabolism suggesting that PPARs play a pivotal role in the adipogenic signaling cascade and lipid homeostasis. PPAR-gamma receptors are associated with regulation of insulin sensitivity and blood glucose levels. PPAR-α activators are associated with lowering plasma triglycerides and LDL cholesterol. PPAR-β activators have been reported to both increase HDL-C levels and to decrease LDL-C levels. Thus, activation of PPAR-P alone, or in combination with the simultaneous activation of PPAR-α and/or PPAR-gamma may be desirable in formulating a treatment for dyslipidemia in which HDL is increased and LDL lowered. PPAR-activation is readily determined by those skilled in the art by the standard assays (e.g. US 2003/0225158 and US 2004/0157885). Examples of suitable PPAR-activator compounds include, but are not limited to, those described in US 2003/0171377, US 2003/0225158, US 2004/0157885, and U.S. Pat. No. 6,710,063. Additional examples of useful PPAR-activator compounds include the following compounds: [5-Methoxy-2-methly-4-(4'-trifluoromethly-biphenyl-4ylmethylsulfanyl)-phenoxy]-acetic acid; [5-Methoxy-2-methyl-4-(3'-trifloromethly-biphenyl-4-ylmethylsulfanyl)-phenoxy]-acetic acid; [4-(4'Fluoro-biphenyl-4-ylmethylsulfanyl)-5-methoxy-2methyl-phenoxy]-acetic acid; {5-Methoxy-2methyl-4-[4-(4-trifluoromethyl-benzyloxy)-benzylsulfanyl]-phenoxy)-acetic acid; {{5-Methoxy-2-methyl-4-[4-(5-trifluoromethyl-pryidin-2-yl)-benzylsulfanyl]-phenoxy}-acetic acid; (4-{4-[2-(3-Fluoro-phenyl)-vinyl]-benzylsulfanyl}-5-methoxy-2-methyl-phenoxy)-acetic acid; [5-Methoxy-2-methyl-4-(3-methyl-4'-trifluoromethyl-biphenyl-4-ylmethylsulfanyl)-phenoxy]-acetic acid; [5-Methoxy-2-methyl-4-(4'-trifluoromethyl-biphenyl-3-ylmethylsulfanyl)-phenoxy]-acetic acid; {5-Methoxy-2-methyl-4-[2-(4-trifluoromethyl-benzyloxy)-benzylsulfanyl]-phenoxy}acetic acid; 3-{5-[2-(-5-Methyl-2  phenyl-oxazol-4yl-ethoxy]-indol-1-yl}-propionic acid; 3-{4[2-(5-methyl-2-phenyl-1,3-oxazol-4-yl) ethoxy-1H-indazol-1 yl}propanoic acid; 2-Methyl-2-{3-[({2-(5-methyl-2-phenyl-1,3-oxazol-4-yl)ethoxy] carbanoyl}amino)methyl]phenoxy}propionic acid; 1-{3'-[2-5-Methyl-2-phenyl-1,3-oxazol-4-y]-1,1'-biphenyl-3-yl}oxy)cyclobutanecarboxylic acid; 3-[3-(1-Carboxy-1-methyl-ethoxy)-phenyl]-piperidine-1-carboxylic acid 3-trifluoromethyl-benzyl ester; 2-{2-methyl-4-[({4-methyl-2-[4-(trifluoromethyl)phenyl]-1,3-thiazol-5-yl}methyl)sulfanyl]phenoxy}acetic acid; 2-{2-methyl-4-[({4-methyl-2-[4-(trifluoromethyl)phenyl]-1,3-oxazol-5-yl}methyl) sulfanyl]phenoxy}acetic acid; methyl 2-{4-[({4-methyl-2-[4-(trifluoromethyl)phenyl]-1,3-thiazol-5-yl}methyl) sulfanyl]phenoxy}acetate; 2-{4-[({4-methyl-2-[4-(trifluoromethyl)phenyl]-1,3-thiazol-5-yl}methyl)sulfanyl] phenoxy}acetic acid; (E)-3-[2-methyl-4-({4-methyl-2-[4-

(trifluoromethyl)phenyl]-1,3-thiazol-5-yl}methoxy)phenyl]-2-propenoic acid; 2-{3-chloro-4-[({4-methyl-2-[4-(trifluoromethyl)phenyl]-1,3-thiazol-5-yl}methyl)sulfanyl]phenyl}acetic acid; 2-{2-methyl-4-[({4-methyl-2-[3-fluoro-4-(trifluoromethyl)phenyl]-1,3-thiazo 1-5-yl}methyl)sulfanyl]phenoxy}acetic acid; and pharmaceutically acceptable salts thereof.

Any MTP/Apo B secretion (microsomal triglyceride transfer protein and/or apolipoprotein B secretion) inhibitor known in the art which inhibits the secretion of triglycerides, cholesteryl ester and phospholipids may be used. Such inhibition may be readily determined according to standard assays (e.g., Wetterau, J. R. 1992; Science 258:999). Examples of suitable a MTP/Apo B secretion inhibitor include, but are not limited to, imputapride (Bayer) as well as those described in WO 96/40640 and WO 98/23593.

Any ACAT inhibitor known in the art that inhibits the intracellular esterification of dietary cholesterol by the enzyme acyl CoA: cholesterol acyltransferase may be used. Such inhibition may be determined readily according to standard assays, such as the method of Heider et al. described in Journal of Lipid Research. 24:1127 (1983). Examples of suitable ACAT inhibitors include, but are not limited to, those described in U.S. Pat. No. 5,510,379 (carboxysulfonates), WO 96/26948 and WO 96/10559 (urea derivatives). Additional examples include Avasimibe (Pfizer), CS-505 (Sankyo) and Eflucimibe (Eli Lilly and Pierre Fabre).

Any lipase inhibitor (e.g., pancreatic lipase inhibitor, a gastric lipase inhibitor) known in the art that inhibits the metabolic cleavage of dietary triglycerides into free fatty acids and monoglycerides may be used. Such lipase inhibition activity may be readily determined according to standard assays (e.g., Methods Enzymol. 286: 190-231). Examples of a suitable lipase inhibitor include, but are not limited to, lipstatin, (2S,3S,5S,7Z,10Z)-5-[(S)-2-formamido-4-methyl-valeryloxy]-2-hexyl-3-hydro-xy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexa-decanoic 1,3 acid lactone, and the variously substituted N-formylleucine derivatives and stereoisomers thereof (U.S. Pat. No. 4,598,089); tetrahydrolipstatin U.S. Pat. Nos. 5,274,143; 5,420,305; 5,540,917; and 5,643,874; FL-386, 1-[4-(2-methylpropyl)cyclohexyl]-2-[-(phenylsulfonyl)oxy]-ethanone, and the variously substituted sulfonate derivatives related thereto (U.S. Pat. No. 4,452,813); WAY-121898, 4-phenoxyphenyl-4-methylpiperidin-1-yl-carboxylate, and the various carbamate esters and pharmaceutically acceptable salts related thereto (U.S. Pat. Nos. 5,512,565; 5,391,571 and 5,602,151); valilactone, and a process for the preparation thereof by the microbial cultivation of Actinomycetes strain MG147-CF2 (Kitahara, et al., J. Antibiotics, 40 (11), 1647-1650 (1987)); esterastin; ebelactone A and ebelactone B, and a process for the preparation thereof by the microbial cultivation of Actinomycetes strain MG7-G1 (Umezawa, et al., J. Antibiotics, 33, 1594-1596 (1980); Japanese Kokai 08-143457, published Jun. 4, 1996). The compound tetrahydrolipstatin is especially preferred. Additional examples include N-3-trifluoromethylphenyl-N'-3-chloro-4'-trifluoromethylphenylurea, and the various urea derivatives related thereto, U.S. Pat. No. 4,405,644; esteracin (U.S. Pat. Nos. 4,189,438 and 4,242,453); and cyclo-O,O'-[(1,6-hexanediyl)-bis-(iminocarbonyl)]dioxime, and the various bis(iminocarbonyl)dioximes related thereto (Petersen et al., Liebig's Annalen, 562, 205-229 (1949).

Any bile acid sequestrant known in the art may be used. Examples of suitable bile acid sequestrants include, but are not limited to, WELCHOL®, COLESTID®, LoCHOLEST®, QUESTRAN® and fibric acid derivatives, such as ATROMID®, LOPID® and TRICOR®.

A compound of the invention can be used in combination with an anti-diabetic compound, i.e. any compound (e.g. insulin) used in the treating diabetes (especially Type II), insulin resistance, impaired glucose tolerance, or the like, or any of the diabetic complications such as neuropathy, nephropathy, retinopathy or cataracts. Additional examples of an anti-diabetic compound include, but are not limited to, a glycogen phosphorylase inhibitor, an aldose reductase inhibitor, a sorbitol dehydrogenase inhibitor, a glucosidase inhibitor, and an amylase inhibitor.

Any glycogen phosphorylase inhibitor known in the art that inhibits the bioconversion of glycogen to glucose-1-phosphate which is catalyzed by the enzyme glycogen phosphorylase may be used. Such glycogen phosphorylase inhibition activity may be readily determined according to standard assays (e.g., J. Med. Chem. 41 (1998) 2934-2938). A variety of glycogen phosphorylase inhibitors are known to those skilled in the art including those described in WO 96/39384 and WO 96/39385.

Any aldose reductase inhibitor known in the art that inhibits the bioconversion of glucose to sorbitol catalyzed by the enzyme aldose reductase. Aldose reductase inhibition may be readily determined according to standard assays (e.g., J. Malone, Diabetes, 29:861-864 (1980). "Red Cell Sorbitol, an Indicator of Diabetic Control").

Any sorbitol dehydrogenase inhibitor known in the art that inhibits the bioconversion of sorbitol to fructose catalyzed by the enzyme sorbitol dehydrogenase may be used. Such sorbitol dehydrogenase inhibitor activity may be readily determined according to standard assays (e.g., Analyt. Biochem (2000) 280: 329-331). Examples of a suitable sorbitol dehydrogenase inhibitor include, but are not limited to, those described in U.S. Pat. Nos. 5,728,704 and 5,866,578.

Any glucosidase inhibitor known in the art that inhibits the enzymatic hydrolysis of complex carbohydrates by glycoside hydrolases, for example amylase or maltase, into bioavailable simple sugars, for example, glucose. Such glucosidase inhibition activity may be readily determined by those skilled in the art according to standard assays (e.g., Biochemistry (1969) 8: 4214).

A generally preferred glucosidase inhibitor includes an amylase inhibitor. Any amylase inhibitor known in the art that inhibits the enzymatic degradation of starch or glycogen into maltose may be used. Such amylase inhibition activity may be readily determined by those skilled in the art according to standard assays (e.g., Methods Enzymol. (1955)1: 149).

Other preferred glucosidase inhibitors include, but are not limited to, acarbose and the various amino sugar derivatives related thereto (U.S. Pat. Nos. 4,062,950 and 4,174,439); adiposine (U.S. Pat. No. 4,254,256); voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto (U.S. Pat. No. 4,701,559); miglitol, (2R,3R,4R,5S)-1-(2-hydroxyethyl)-2-(hydroxymethyl)-3,4,5-piperidinetriol, and the various 3,4,5-trihydroxypiperidines related thereto (U.S. Pat. No. 4,639,436); emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof (U.S. Pat. No. 5,192,772); MDL-25637, 2,6-dideoxy-7-O-.beta.-D-glucopyrano-syl-2,6-imino-D-glycero-L-gluco-heptitol, the various homodisaccharides related thereto and the pharmaceutically acceptable acid addition salts thereof (U.S. Pat. No. 4,634,765); camiglibose, methyl 6-deoxy-6-[(2R,3R,4R,5S)-3,4,5-trihydroxy-2-

(hydroxymethyl)piperidino]-.alpha.-D-glucopyranoside sesquihydrate, the deoxy-nojirimycin derivatives related thereto, the various pharmaceutically acceptable salts thereof and synthetic methods for the preparation thereof (U.S. Pat. Nos. 5,157,116 and 5,504,078); pradimicin-Q; and salbostatin and the various pseudosaccharides related thereto (U.S. Pat. No. 5,091,524).

Any amylase inhibitor known in the art may be used. Examples include, but are not limited to, tendamistat and the various cyclic peptides related thereto (U.S. Pat. No. 4,451,455); Al-3688 and the various cyclic polypeptides related thereto (U.S. Pat. No. 4,623,714); and trestatin, consisting of a mixture of trestatin A, trestatin B and trestatin C and the various trehalose-containing aminosugars related thereto, (U.S. Pat. No. 4,273,765).

Additional examples of an anti-diabetic compound for use in a combination of the invention include: biguanides (e.g., mefformin), insulin secretagogues (e.g., sulfonylureas and glinides), glitazones, non-glitazone PPAR.gamma. agonists, PPAR.beta. agonists, inhibitors of DPP-IV, inhibitors of PDE5, inhibitors of GSK-3, glucagon antagonists, inhibitors of f-1,6-BPase (Metabasis/Sankyo), GLP-1/analogs (AC 2993, also known as exendin-4), insulin and insulin mimetics (Merck natural products), PKC-beta inhibitors, and AGE breakers.

A compound of the invention can be used in combination with any anti-obesity agent known in the art. Anti-obesity activity may be readily determined according to standard assays known in the art. Examples of suitable anti-obesity agents include, but are not limited to, phenylpropanolamine, ephedrine, pseudoephedrine, phentermine, .beta..sub.3 adrenergic receptor agonists, apolipoprotein-B secretion/microsomal triglyceride transfer protein (apo-B/MTP) inhibitors, MCR-4 agonists, cholecystokinin-A (CCK-A) agonists, monoamine reuptake inhibitors (e.g., sibutramine—U.S. Pat. No. 4,929,629), sympathomimetic agents, serotoninergic agents, cannabinoid receptor antagonists (e.g., rimonabant (SR-141,716A)), dopamine agonists (e.g., bromocriptine—U.S. Pat. Nos. 3,752,814 and 3,752,888), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine.™), human agouti-related proteins (AGRP), ghrelin receptor antagonists, histamine 3 receptor antagonists or inverse agonists, neuromedin U receptor agonists, and the like.

Any thyromimetic agent known in the art may also be used in combination with a compound of the invention. Thyromimetic activity may be readily determined according to standard assays (e.g., Atherosclerosis (1996) 126: 53-63). Examples of suitable thyromimetic agents include, but are not limited to, those described in U.S. Pat. Nos. 4,766,121; 4,826,876; 4,910,305; 5,061,798; 5,284,971; 5,401,772; 5,654,468; and 5,569,674.

A compound of the invention may further be used in combination with an anti-resorptive agent (e.g., progestins, polyphosphonates, bisphosphonate(s), estrogen agonists/antagonists, estrogen, estrogen/progestin combinations, Premarin.™, estrone, estriol or 17.alpha.- or 17.beta.-ethynyl estradiol). Exemplary progestins are available from commercial sources and include, but are not limited to: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type described in U.S. Pat. No. 3,683,080. Preferred polyphosphonates are geminal diphosphonates (also referred to as bis-phosphonates), 6-amino-1-hydroxy-hexylidene-bisphosphonic acid and 1-hydroxy-3(methylpentylamino)-propylidene-bisphosphonic acid. Tiludronate disodium, ibandronic acid, alendronate, resindronate, and zoledronic acid are each especially preferred polyphosphonates. The polyphosphonates may be administered in the form of the acid, or of a soluble alkali metal salt or alkaline earth metal salt. Hydrolyzable esters of the polyphosphonates are likewise included. Specific examples include, but are not limited to, ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

Any estrogen agonist/antagonist known in the art which bind with the estrogen receptor, inhibit bone turnover and/or prevent bone loss may be used in a combination of the invention. More specifically, an estrogen agonist may be any chemical compound capable of binding to the estrogen receptor sites in mammalian tissue, and mimicking the actions of estrogen in one or more tissue. An estrogen antagonist may be any chemical compound capable of binding to the estrogen receptor sites in mammalian tissue, and blocking the actions of estrogen in one or more tissues. Such activities may be readily determined according to standard assays, including estrogen receptor binding assays, and standard bone histomorphometric and densitometer methods (Eriksen E. F. et al., Bone Histomorphometry, Raven Press, New York, 1994, pages 1-74; Grier S. J. et. al., "The Use of Dual-Energy X-Ray Absorptiometry In Animals", Inv. Radiol., 1996, 31(1):50-62; Wahner H. W. and Fogelman I., The Evaluation of Osteoporosis: Dual Energy X-Ray Absorptiometry in Clinical Practice., Martin Dunitz Ltd., London 1994, pages 1-296). Examples of a suitable estrogen agonist/antagonist is 3-(4-(1,2-diphenyl-but-1-enyl)-phenyl)-acrylic acid (see Willson et al., Endocrinology, 1997, 138, 3901-3911); tamoxifen (ethanamine,2-(-4-(1,2-diphenyl-1-butenyl)phenoxy)-N,N-dimethyl, (Z)-2-,2-hydroxy-1,2,3-propanetricarboxylate (1:1)) and related compounds (U.S. Pat. No. 4,536,516); 4-hydroxy tamoxifen (U.S. Pat. No. 4,623,660); raloxifene (methanone, (6-hydroxy-2-(4-hydroxyphenyl)benzo[b]thien-3-yl)(4-(2-(1-piperidinyl)eth-oxy)phenyl)-hydrochloride)(U.S. Pat. No. 4,418,068); toremifene (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) (U.S. Pat. No. 4,996,225); centchroman (1-(2-((4-(-methoxy-2,2, dimethyl-3-phenyl-chroman-4-yl)-phenoxy)-ethyl)-pyrrolidine) (U.S. Pat. No. 3,822,287); levormeloxifene; idoxifene ((E)-1-(2-(4-(1-(4-iodo-phenyl)-2-phenyl-but-1-enyl)-phenoxy)-ethyl)-pyrrolidinone (U.S. Pat. No. 4,839,155); 2-(4-methoxy-phenyl)-3-[4-(2-piperidin-1-yl-ethoxy)-phenoxy]-benzo[b]thiophen-6-ol (U.S. Pat. No. 5,488,058); 6-(4-hydroxy-phenyl)-5-(4-(2-piperidin-1-yl-ethoxy)-benzyl)-naphthalen-2-ol (U.S. Pat. No. 5,484,795); (4-(2-(2-azabicyclo[2.2.1]hept-2-yl)-ethoxy)-phenyl)-(6-hydroxy-2-(4-hyd-roxy-phenyl)-benzo[b]thiophen-3-yl)-methanone (WO 95/10513 assigned to Pfizer Inc.); TSE-424 (Wyeth-Ayerst Laboratories); arazoxifene; derivatives of 2-phenyl-3-aroyl-benzoth-iophene and 2-phenyl-3-aroylbenzothiophene-1-oxide(U.S. Pat. No. 4,133,814); estrogen agonist/antagonists described in U.S. Pat. No. 4,133,814; and estrogen agonist/antagonists described in commonly assigned U.S. Pat. No. 5,552,412.

Especially preferred estrogen agonist/antagonists described in U.S. Pat. No. 5,552,412 are: cis-6-(4-fluorophenyl)-5-(4-(2-piperidin-1-yl-ethoxy)-phenyl)-5,6,-7,8-tetrahydro-naphthalene-2-ol; (–)-cis-6-phenyl-5-(4-(2-pyrrolidin-1-yl-ethoxy)-phenyl)-5,6,7,8-te-trahydro-naphthalene-2-ol (also known as lasofoxifene); cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,-4-tetrahydroisoquinoline; cis-6-(4-hydroxyphenyl)-5-(4-(2-piperidin-1-yl-ethoxy)-phenyl)-5,6,-7,8-tetrahydro-naphthalene-2-ol; and 1-(4'-pyrrolidinolethoxyphenyl)-2-phenyl-6-hydroxy-1,2,3,4-tetrahyd-roisoquinoline.

Any anti-osteoporosis agent known in the art may be used in a combination of the invention. Examples include, but are not limited to, parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs.

Any antihypertensive agent known in the art may be used in a combination of the invention. Antihypertensive activity may be determined according to standard tests (e.g. blood pressure measurements). Examples of suitable antihypertensive agents include, but are not limited to, (a) amlodipine and related dihydropyridine compounds (U.S. Pat. Nos. 4,572,909 and 5,155,120) such as, but not limited to, amlodipine benzenesulfonate salt (also termed amlodipine besylate (NORVASCl))(U.S. Pat. No. 4,879,303) and other pharmaceutically acceptable acid addition salts of amlodipine (U.S. Pat. No. 5,155,120); (b) calcium channel blockers such as, but not limited to, bepridil (U.S. Pat. No. 3,962, 238 or U.S. Reissue No. 30,577), clentiazem (U.S. Pat. No. 4,567,175), diltiazem (U.S. Pat. No. 3,562), fendiline (U.S. Pat. No. 3,262,977), gallopamil (U.S. Pat. No. 3,261,859); mibefradil, prenylamine, semotiadil, terodiline, verapamil, aranipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, and perhexiline; (c) angiotensin converting enzyme inhibitors ("ACE-inhibitors") such as, but not limited to, alacepril (U.S. Pat. No. 4,248,883), benazepril (U.S. Pat. No. 4,410,520), captopril, ceronapril, delapril, enalapril, fosinopril, imadapril, lisinopril, moveltopril, perindopril, quinapril, ramipril, spirapril, temocapril, and trandolapril; (d) angiotensin-II receptor antagonists such as, but not limited to, candesartan (U.S. Pat. No. 5,196,444), eprosartan (U.S. Pat. No. 5,185,351), irbesartan, losartan, and valsartan; (e) beta-adrenergic receptor blockers (beta- or β-blockers) such as, but not limited to, acebutolol (U.S. Pat. No. 3,857,952), alprenolol, amosulalol (U.S. Pat. No. 4,217, 305), arotinolol, atenolol, befunolol, betaxolol; and (f) alpha-adrenergic receptor blockers (alpha- or α-blockers) such as, but not limited to, amosulalol (U.S. Pat. No. 4,217,307), arotinolol (U.S. Pat. No. 3,932,400), dapiprazole, doxazosin, fenspiride, indoramin, labetolol, naftopidil, nicergoline, prazosin, tamsulosin, tolazoline, trimazosin, and yohimbine, which may be isolated from natural sources according to methods well known to those skilled in the art.

Any compound that is known to be useful in the treatment of Alzheimer's disease may be used in a combination of the invention. Such compounds include acetylcholine esterase inhibitors. Examples of known acetylcholine esterase inhibitors include, but not limited to donepezil (ARICEPT®; U.S. Pat. Nos. 4,895,841, 5,985,864, 6,140,321, 6,245,911 and 6,372,760), tacrine (COGNEX®; U.S. Pat. Nos. 4,631,286 and 4,816,456), rivastigmine (EXELON®; U.S. Pat. Nos. 4,948,807 and 5,602,17) and galantamine (REMINYL; U.S. Pat. Nos. 4,663,318 and 6,099,863).

The present invention contains compounds that can be synthesized in a number of ways familiar to one skilled in organic synthesis. The following non-limiting reaction schemes illustrate the preparation of the compounds of the present invention. Unless otherwise indicated, all variables in the reaction schemes and the discussion that follow are defined above. Also unless indicated otherwise, all starting materials and/or reagents are commercially available. As would be understood by one of skill in the art, individual compounds may require manipulation of the conditions in order to accommodate various functional groups. A variety of protecting groups known to one skilled in the art may be required. Purification, if necessary, may be accomplished on a silica gel column eluted with the appropriate organic solvent system. Also, reverse phase HPLC or recrystallization may be employed.

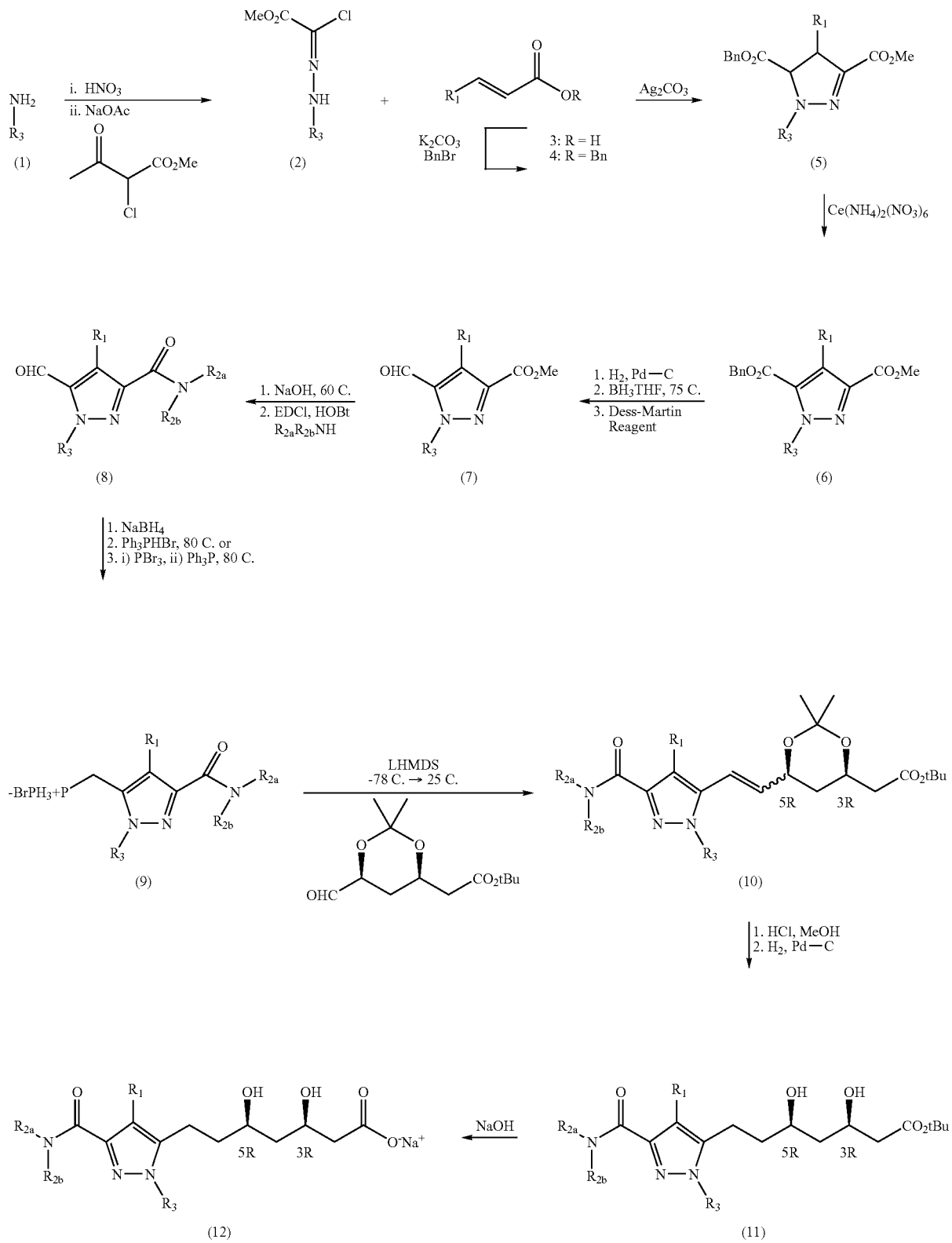

Scheme 1 describes a general synthetic scheme for the preparation of a compound (12) from an amine (1). As would be understood by one of skill in the art, elimination of the hydrogenation step from the conversion of compound (10) to compound (11) provides the corresponding olefin derivative.
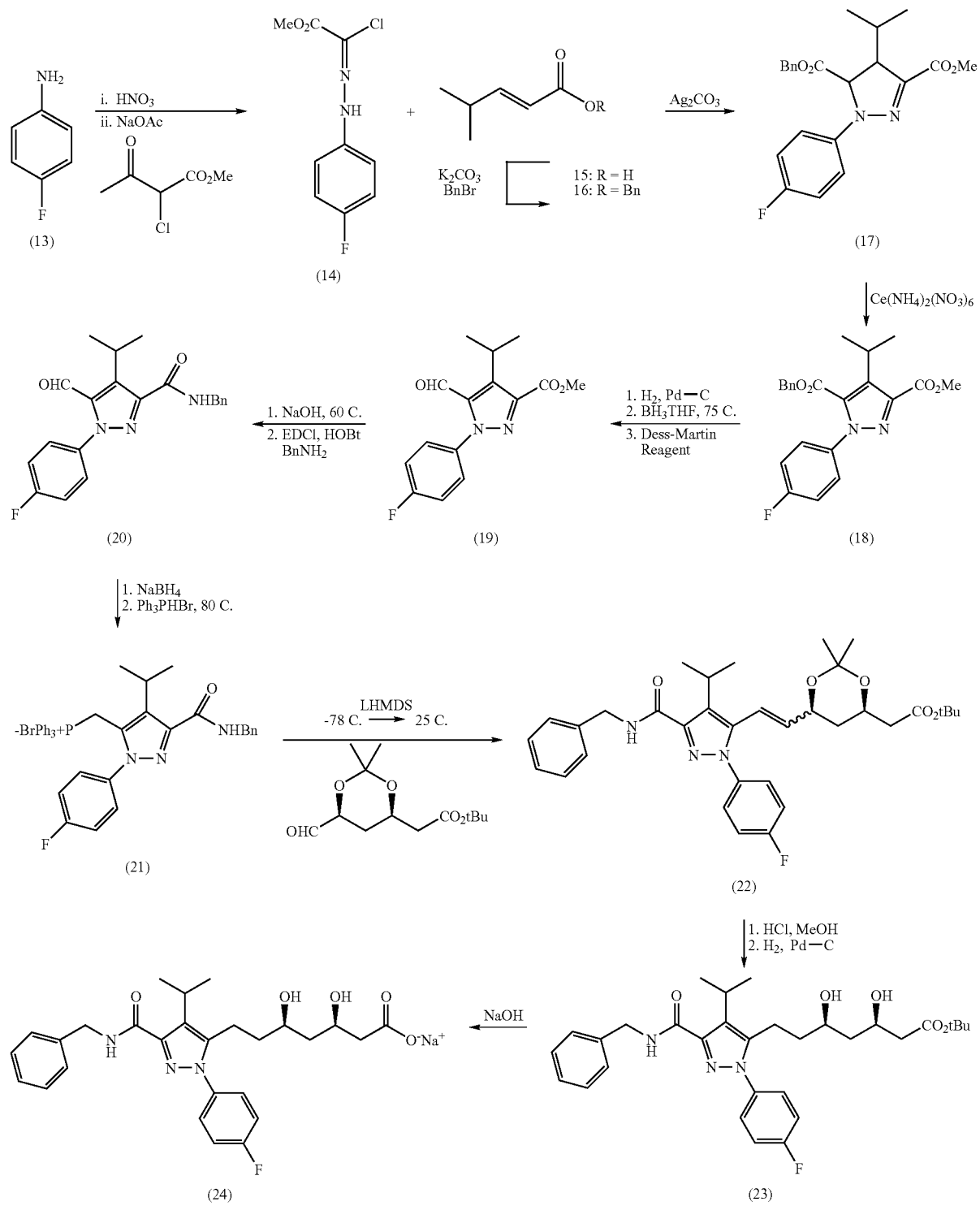
Scheme 1a Scheme 1a highlights the preparation of compounds of this invention using compound (24) as a representative, non-limiting example. As shown, 4-fluoroaniline (13) (commercially available from Sigma-Aldrich, Milwaukee, Wis.) was initially converted to a diazonium salt and reacted with methyl 2-chloroacetoacetate to give hydrazonoyl chloride (14). Treatment of hydrazonoyl chloride (14) with $Ag_2CO_3$ resulted in in-situ generation of a nitrilimine that was engaged in a 1,3-dipolar cycloaddition with enone (16) to provide dihydropyrazole (17) as the major regioisomer. Ceric ammonium nitrate (CAN) oxidation converted dihydropyrazole (17) to pyrazole (18). Through a subsequent series of routine manipulations pyrazole (18) was converted to amide (20). The mevalonate side chain was installed by initial reduction of the aldehyde functionality of intermediate (20) to the corresponding alcohol which was converted to phosphonium salt (21) by treatment with triphenylphosphine hydrobromide. Wittig olefination of phosphonium salt (21) afforded olefin (22). Removal of the acetonide protecting group with HCl followed by hydrogenation gave intermediate (23). Elimination of the hydrogenation step in this last step provides the corresponding olefin derivative. Finally, the ester of compound (23) was hydrolyzed by treatment with NaOH to give compound (24) which was isolated as a carboxylate salt.

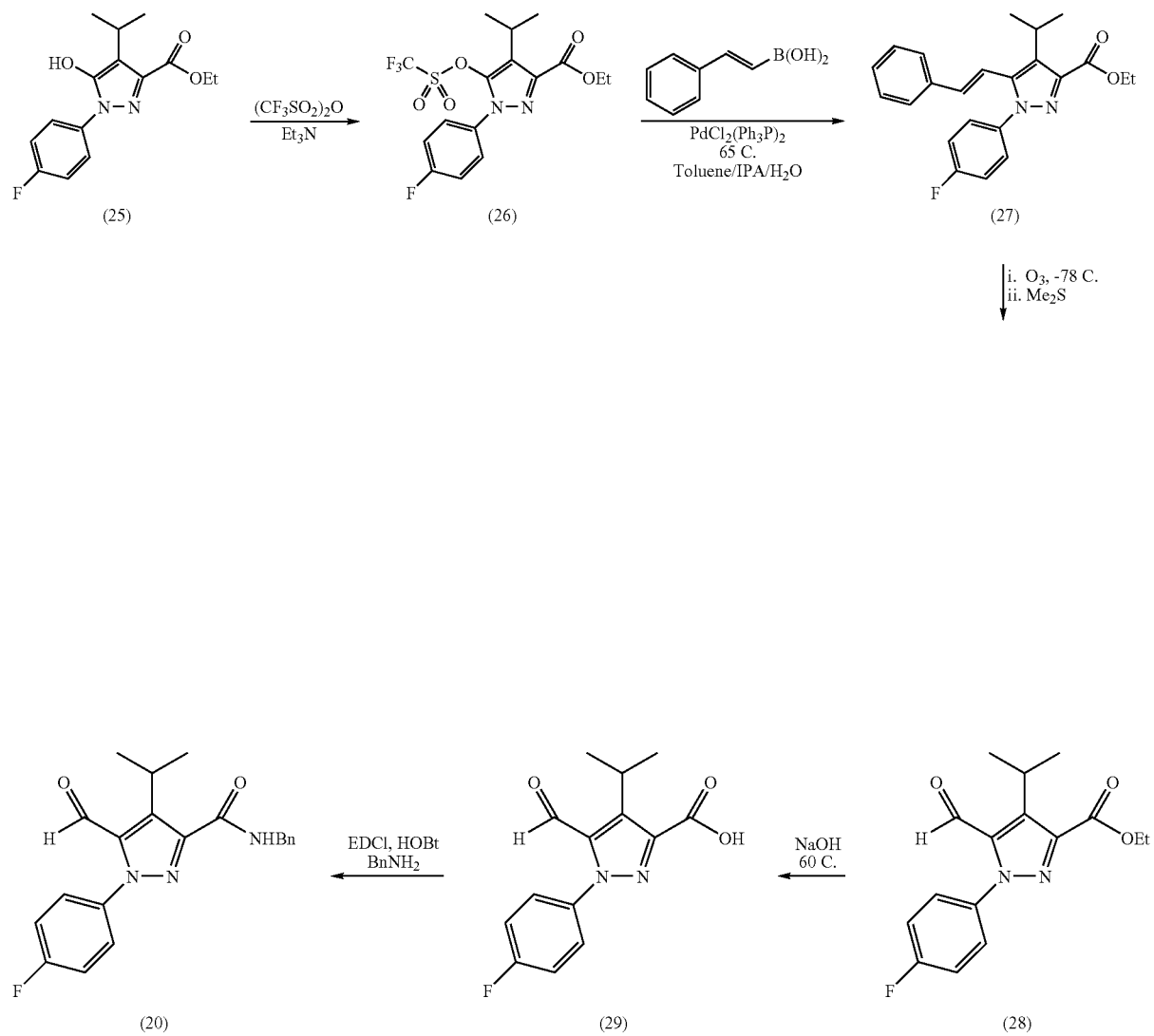

Scheme 1b

Scheme 1b illustrates another method for the preparation of amide (20). Hydroxy-pyrazole (25) was prepared according to procedures described in attorney docket number PC32787, U.S. Provisional Application No. 60/653,469 filed on Feb. 15, 2005 and was then converted to triflate (26). A palladium-mediated coupling of triflate (26) with 2-styreneboronic acid afforded compound (27) which was subsequently subjected to ozonolysis conditions to provide aldehyde (28). Hydrolysis of the ester of intermediate (28) provided carboxylic acid (29) which was finally converted to amide (20) via an N-(3-dimethylaminopropyl)-N-ethylcarbodiimide hydrochloride (EDCI) mediated coupling reaction.

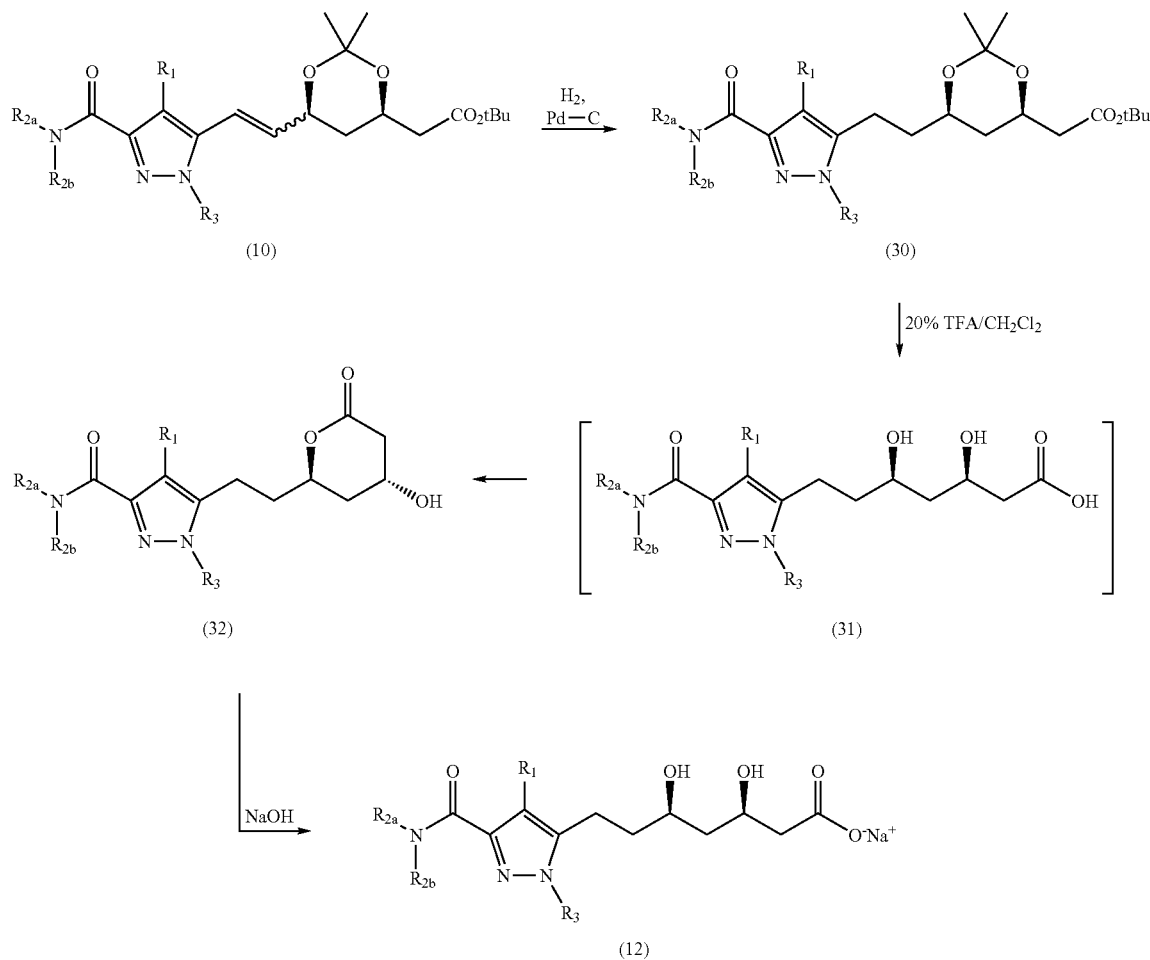

Scheme 2 describes an additional method for the preparation of compounds of this invention. As illustrated, intermediate (10, from Scheme 1) is hydrogenated over Pd—C to provide compound (30). Treatment of compound (30) with 20% TFA/CH$_2$Cl$_2$ provides lactone (32) via carboxylic acid (31). Lactone (32) can be utilized as is or converted to the corresponding carboxylate sodium salt (12) by treatment with NaOH.

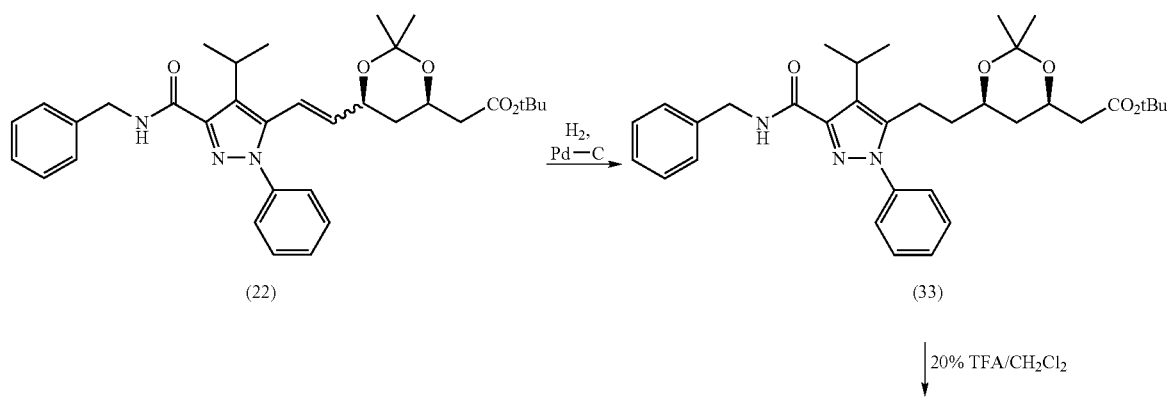

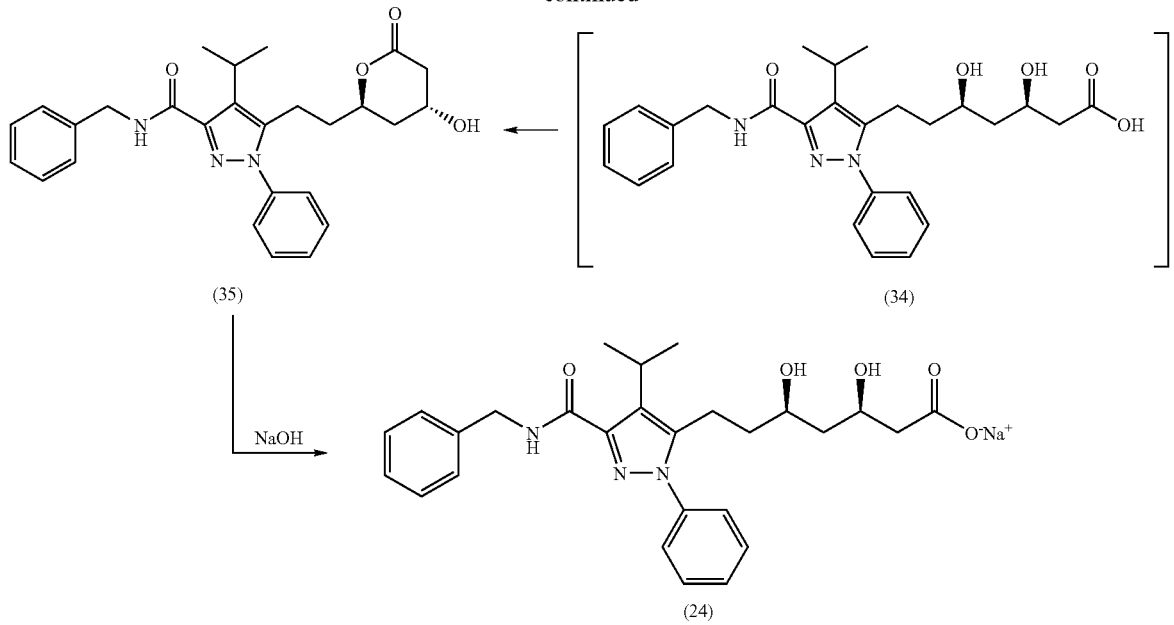

Scheme 2a describes an alternative method for the preparation of compound (24) utilizing compound (22) as a representative, non-limiting example of the invention. As illustrated, intermediate (22, from Scheme 1a) is hydrogenated over Pd—C to provide compound (33). Treatment of compound (28) with 20% TFA/CH$_2$Cl$_2$ provides lactone (35) via the intermediacy of carboxylic acid (34). Lactone (35) can be utilized as is or converted to the corresponding carboxylate sodium salt (24) by treatment with NaOH.

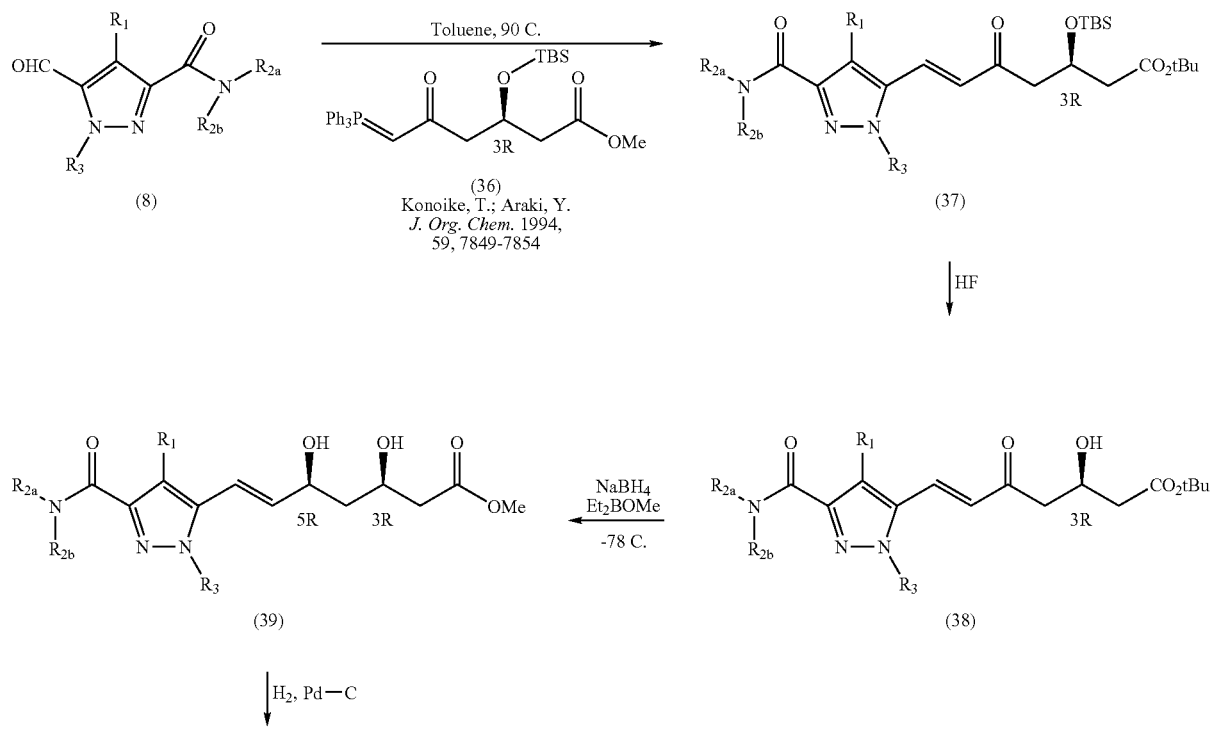

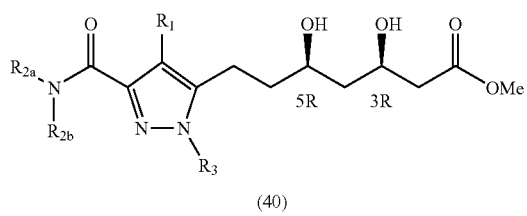

(40)

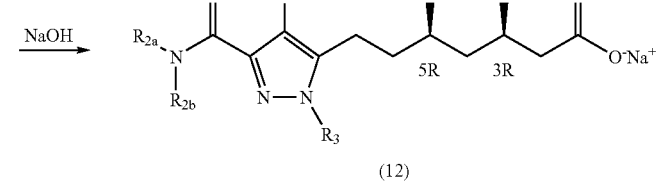

(12)

Scheme 3 illustrates a method for preparing compound (12). Aldehyde (8) was prepared as set forth in Scheme 1 and was then condensed with the known phosphonium ylide (36) [for preparation, see: Konoike, T.; Araki, Y. *J. Org. Chem.* 1994, 59, 7849-7854] to afford olefin (37). Treatment of compound (37) with hydrofluoric acid afforded keto-alcohol (38) which was subsequently reduced with sodium borohydride to give diol (39). The olefin of compound (39) was then hydrogenated giving (40) which was treated with aqueous sodium hydroxide to provide compound (12).

Scheme 3a illustrates a method for preparing compound (46) as a representative, non-limiting example of the invention. Aldehyde (41) was prepared according to the method of Scheme 1 for the preparation of compound (8) and was then condensed with the known phosphonium ylide (36) [for preparation, see: Konoike, T.; Araki, Y. *J. Org. Chem.* 1994, 59, 7849-7854] to afford olefin (42). Treatment of compound (42) with hydrofluoric acid afforded keto-alcohol (43) which was subsequently reduced with sodium borohydride to give diol (44). The olefin of compound (44) was then hydroge-

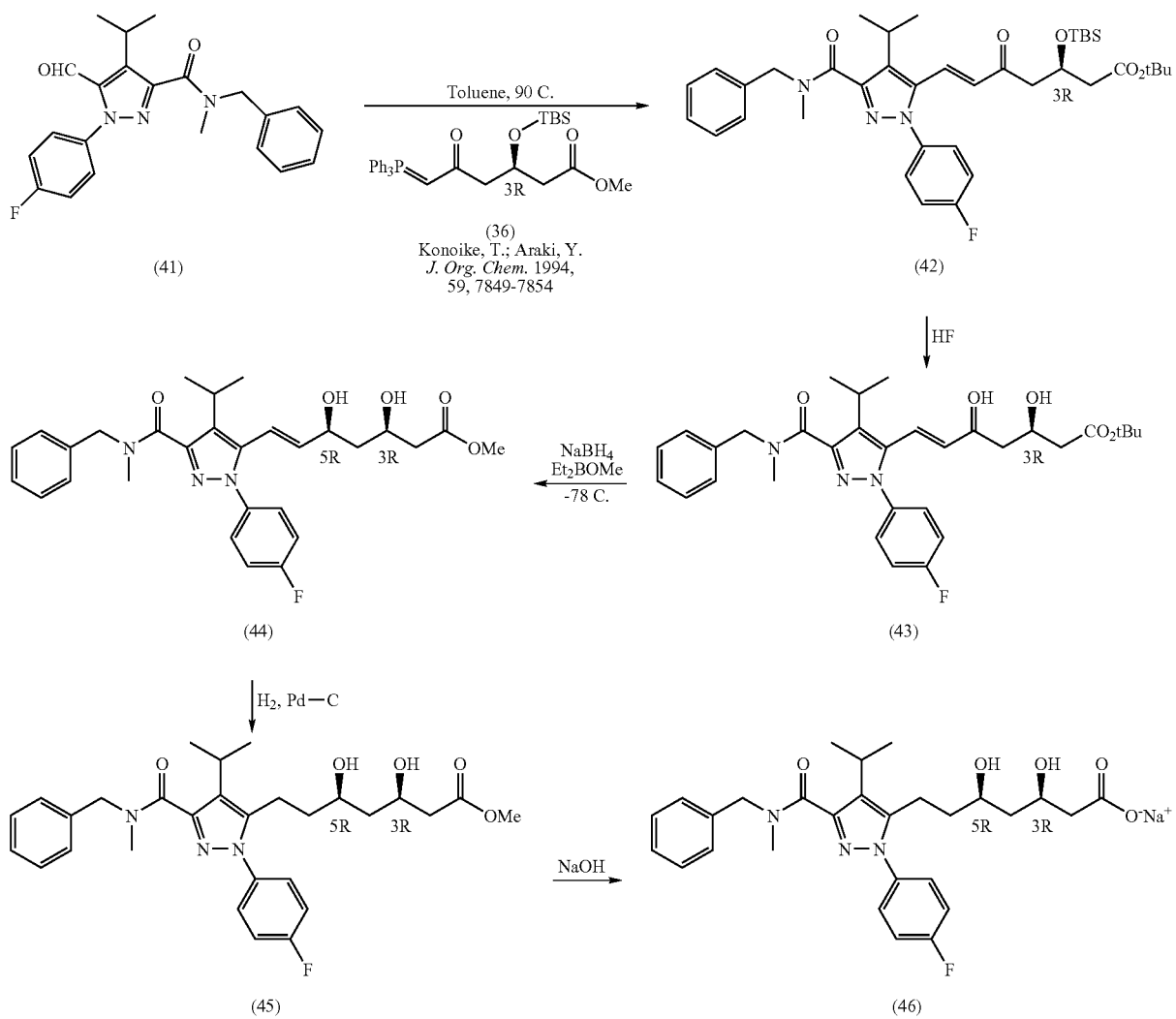

nated giving (45) which was treated with aqueous sodium hydroxide to provide compound (46).

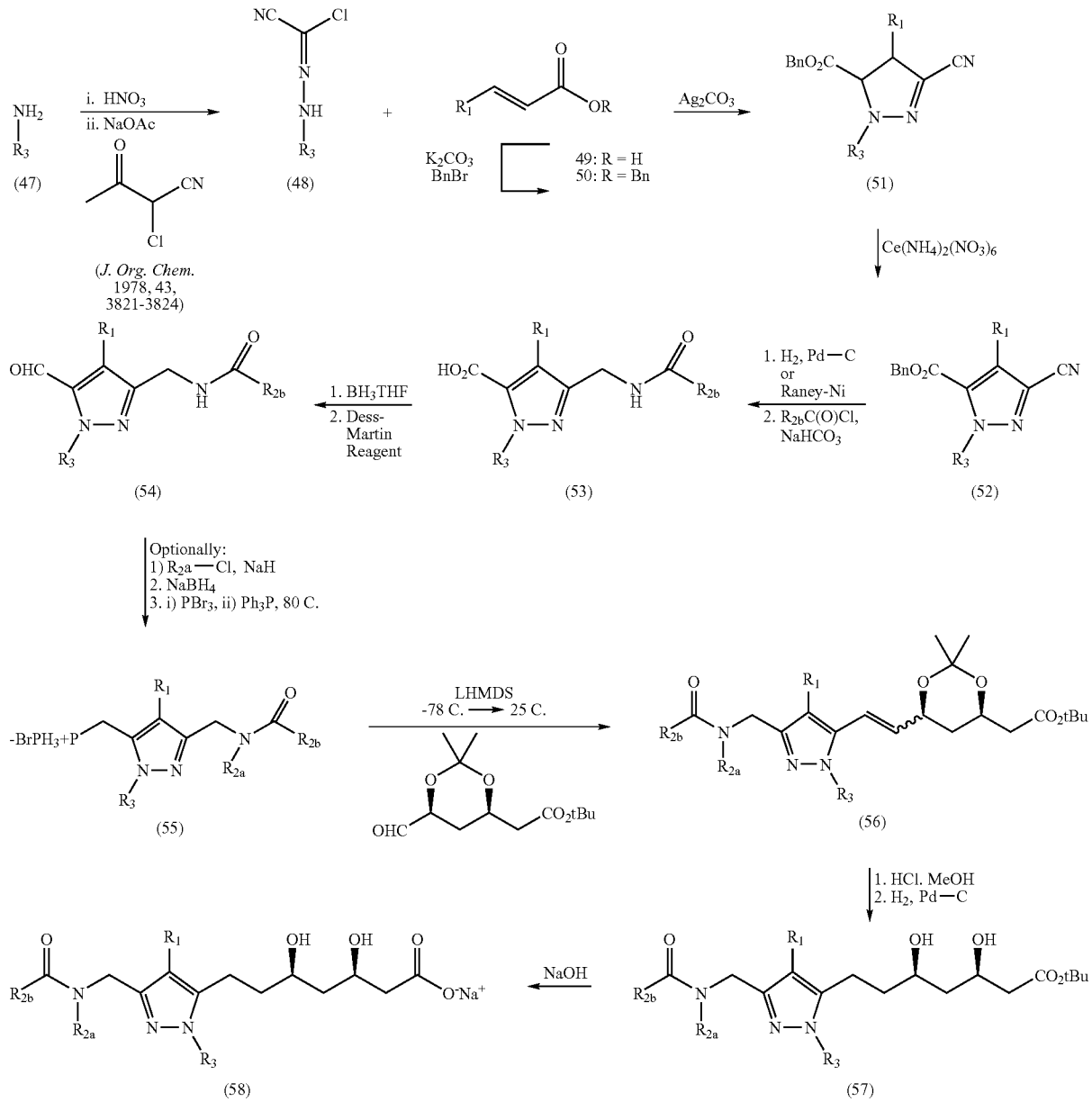

Scheme 4

Scheme 4 highlights the preparation of compounds of this invention using compound (58) as a representative, non-limiting example. As shown, amine (47) is converted to a diazonium salt and reacted with 2-chloro-3-oxo-butyronitrile (*J. Org. Chem.* 1978, 43, 3821-3824) to give hydrazonoyl chloride (48). Treatment of hydrazonoyl chloride (48) with $Ag_2CO_3$ results in in-situ generation of a nitrilimine that is engaged in a 1,3-dipolar cycloaddition with enone (50) to provide dihydropyrazole (51). Ceric ammonium nitrate (CAN) oxidation converts dihydropyrazole (51) to pyrazole (52). Hydrogenation of pyrazole (52) over either Pd—C or Raney-Ni followed by treatment with $R_{2b}C(O)Cl$ and base provides amide (53). Reduction of (53) followed by oxidation provides intermediate (54). Intermediate (54) can be optionally N-alkylated by treatment with $R_{2a}$—Cl and base. The mevalonate side chain is installed by initial reduction of the aldehyde functionality of intermediate (54) to the corresponding to alcohol which is converted to phosphonium salt (55) by treatment with triphenylphosphine hydrobromide. Wittig olefination of phosphonium salt (55) affords olefin (56). Removal of the acetonide protecting group with HCl followed by hydrogenation gives intermediate (57). Elimination of the hydrogenation step in this last step provides the corresponding olefin derivative. Finally, the ester of compound (57) is hydrolyzed by treatment with NaOH to give compound (58) which is isolated as a carboxylate salt. Notably, substitution of $R_{2b}C(O)Cl$ with $R_{2b}SOCl$ or $R_{2b}SO_2Cl$ in the conversion of (52) to (53) allows for preparation of the corresponding sulfinamide and sulfonamide derivatives of compound (58), respectively.
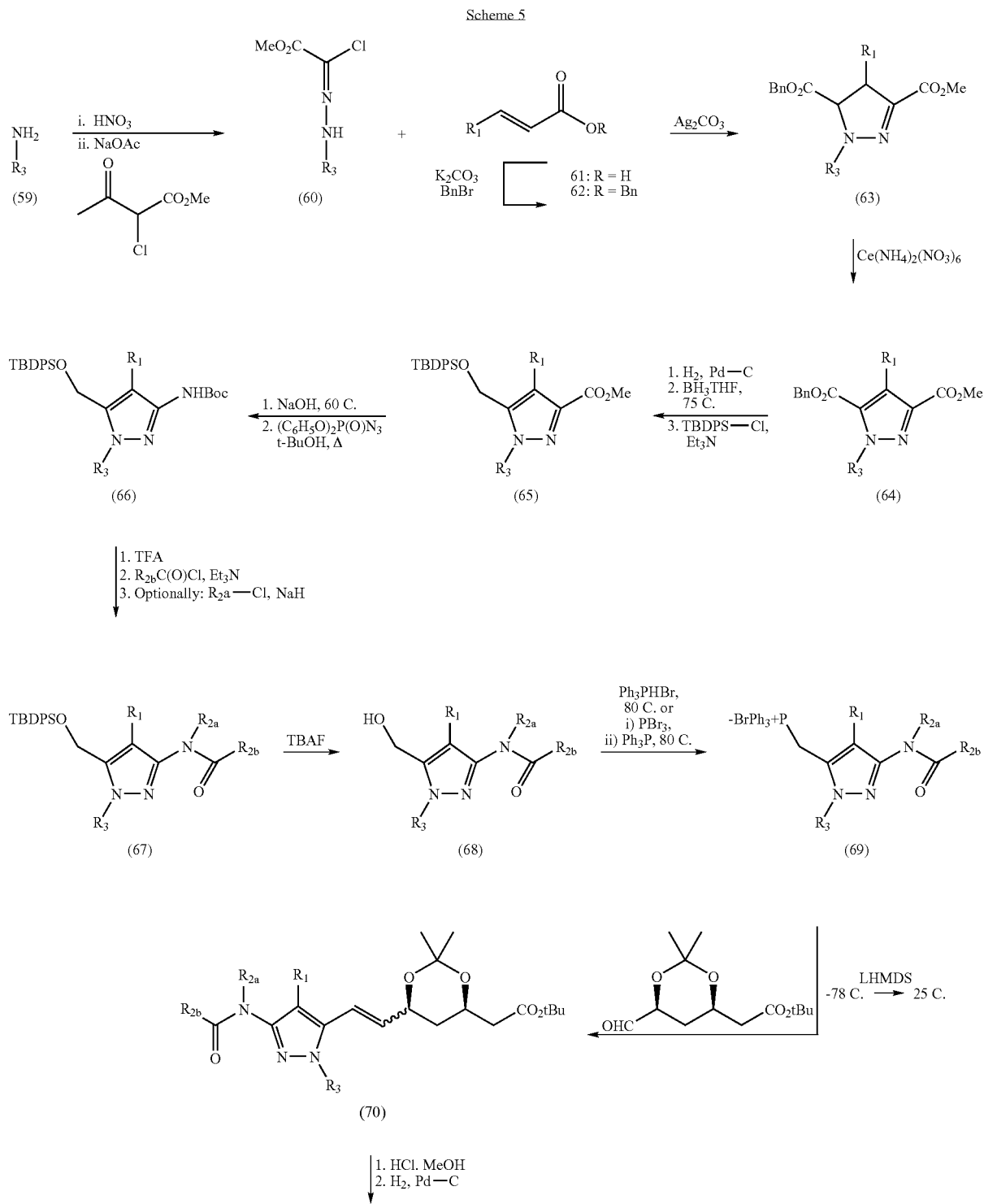

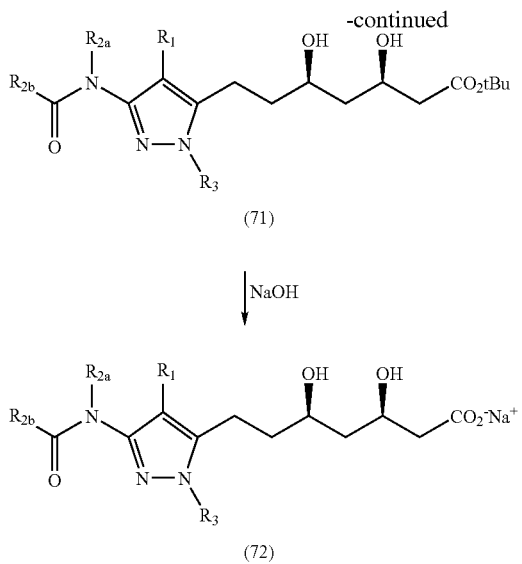

Scheme 5 highlights the preparation of compounds of this invention using compound (72) as a representative, non-limiting example. As shown, amine (59) is converted to a diazonium salt and reacted with methyl 2-chloroacetoacetate to give hydrazonoyl chloride (60). Treatment of hydrazonoyl chloride (60) with $Ag_2CO_3$ results in in-situ generation of a nitrilimine that is engaged in a 1,3-dipolar cycloaddition with enone (62) to provide dihydropyrazole (63). Ceric ammonium nitrate (CAN) oxidation converts dihydropyrazole (63) to pyrazole (64). Hydrogenation of pyrazole (64) over Pd—C followed by reduction and protection provides compound (65). Hydrolysis of (65) gives a carboxylic acid that is treated with diphenylphosphoryl azide in t-BuOH at elevated temperature to provide compound (66). Acidic deprotection and acylation with $R_{2b}C(O)Cl$ provides intermediate (67) which can be optionally N-alkylated by treatment with $R_{2a}$—Cl and base. The mevalonate side chain is installed by initial deprotection of the alcohol functionality of intermediate (67) and conversion to phosphonium salt (69) by treatment with triphenylphosphine hydrobromide. Wittig olefination of phosphonium salt (69) affords olefin (70). Removal of the acetonide protecting group with HCl followed by hydrogenation gives intermediate (71). Elimination of the hydrogenation step in this last step provides the corresponding olefin derivative. Finally, the ester of compound (71) is hydrolyzed by treatment with NaOH to give compound (72) which is isolated as a carboxylate salt. Notably, substitution of $R_{2b}C(O)Cl$ with $R_{2b}SOCl$ or $R_{2b}SO_2Cl$ in the conversion of (66) to (67) allows for preparation of the corresponding sulfinamide and sulfonamide derivatives of compound (72). Notably, substitution of $R_{2b}C(O)Cl$ with $R_{2b}SOCl$ or $R_{2b}SO_2Cl$ in the conversion of (66) to (67) allows for preparation of the corresponding sulfinamide and sulfonamide derivatives of compound (72), respectively.

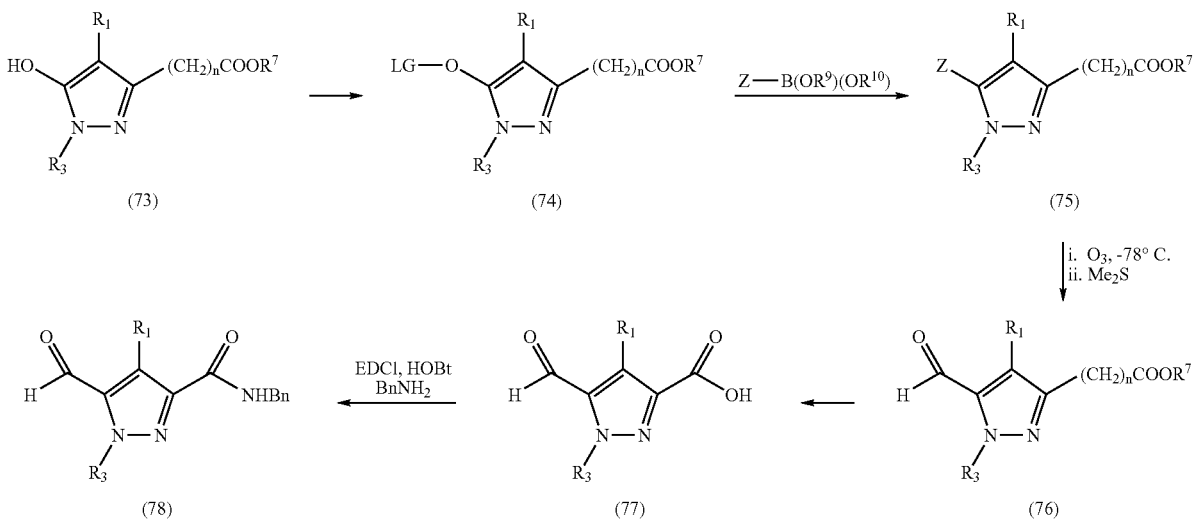

Scheme 6a illustrates the preparation of compound (78). Hydroxyl compound (73) is reacted under suitable conditions to form compound (74). The "LG-O" of compound (74) together represents any suitable leaving group such as, for example, tirfluoromethanesulfonate ($CF_3SO_3$), mesylate ($CH_3SO_3$), tosylate ($CH_3C_6H_4SO_3$), such that upon reaction with a suitable boronic acid or ester affords compound (75). Examples of suitable boronic acids and esters include any boronic acid or boronic ester that would convert compound (74) to compound (75) including those of formula Z-B($OR^9$)($OR^{10}$) where Z is R''' or R''''CX'=CX''Y where R''' can be alkenyl; $R^9$, $R^{10}$, R'''', X' and X'' can each be hydrogen, alkyl, alkenyl, aryl, heteroaryl, or alkenyl substituent and where $R^9$ and $R^{10}$ can be taken together with the oxygens to which they are attached to form a mono-, bi- or polycyclic ring optionally containing one or more degrees of unsaturation and optionally further substituted; Y is either a direct bond or a linker group (e.g. alkylene group); and wherein the non-hydrogen groups of $R^9$, $R^{10}$, R''', R'''', X', X'', and Y are optionally substituted as defined herein.

Compound (75) can then be subjected to ozonolysis conditions to afford aldehyde (76). Hydrolysis of the ester moiety of (76) will provide carboxylic acid (77) which in turn can then be converted to amide (78) via an EDCI mediated coupling reaction. Compound (78) can then be converted to a compound of the invention in a manner analogous to the conversion of compound (8) to compound (12) illustrated in Scheme 1.

Alternatively, the conversion of compound (74) to compound (75) can be achieved using a compound of formula ($R^{10}O$)($R^9O$)B-Z-B($OR^9$)($OR^{10}$), wherein Z,$R^9$ and $R^{10}$ are each independently as defined herein.

Alternatively, the conversion of compound (74) to compound (75) can be achieved using a compound of formula Z-$BF_3$K, wherein Z is as defined herein.

Scheme 6b

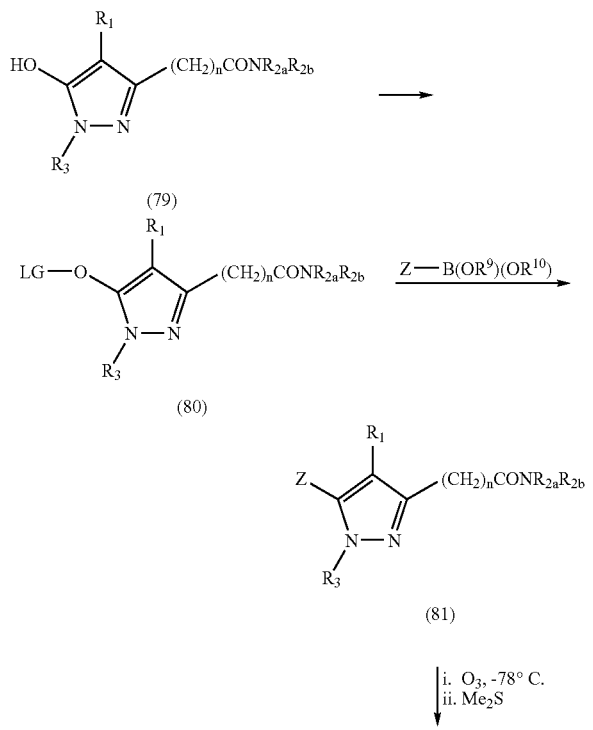

i. $O_3$, -78° C.
ii. $Me_2S$

-continued

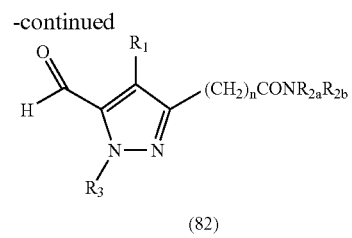

(82)

Scheme 6b illustrates the preparation of compound (82). Hydroxyl compound (79) is reacted under suitable conditions to form compound (80). The "LG-O" of compound (80) together represents any suitable leaving group such as, for example, trifluoromethanesulfonate ($CF_3SO_3$), mesylate ($CH_3SO_3$), tosylate ($CH_3C_6H_4SO_3$), such that upon reaction with a suitable boronic acid or ester affords compound (81). Examples of suitable boronic acids and esters include any boronic acid or ester that would convert compound (80) to compound (81) including those of formula Z-B($OR^9$)($OR^{10}$) where Z is R''' or R''''CX'=CX''Y where R''' can be alkenyl; $R^9$, $R^{10}$, R'''', X' and X'' can each be hydrogen, alkyl, alkenyl, aryl, heteroaryl, or alkenyl substituent and where $R^9$ and $R^{10}$ can be taken together with the oxygens to which they are attached to form a mono-, bi- or polycyclic ring optionally containing one or more degrees of unsaturation and optionally further substituted; Y is either a direct bond or a linker group (e.g. alkylene linker group); and wherein the non-hydrogen groups of $R^9$, $R^{10}$, R''', R'''', X', X'', and Y are optionally substituted as defined herein.

Compound (81) can then be subjected to ozonolysis conditions to afford aldehyde (82). Compound (82) can then be converted to a compound of the invention in a manner analogous to the conversion of compound (8) to compound (12) illustrated in Scheme 1.

Examples of suitable compounds for the conversion of compound (74) or (80) to, respectively, compound (75) and (81), as illustrated in Schemes 6a and 6b, include but are not limited to:

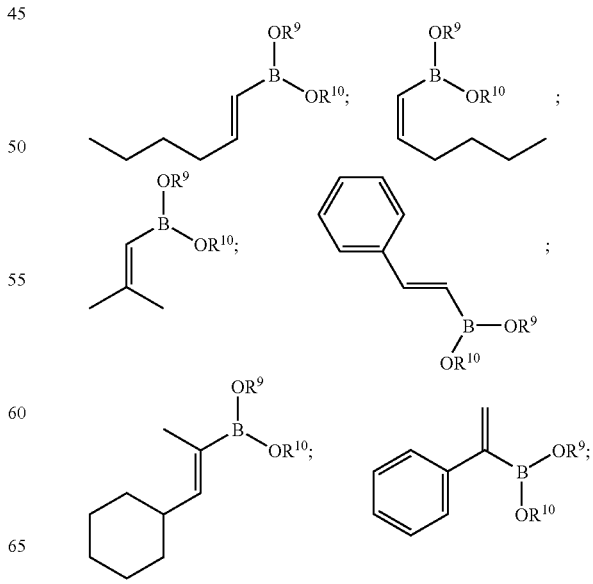

-continued

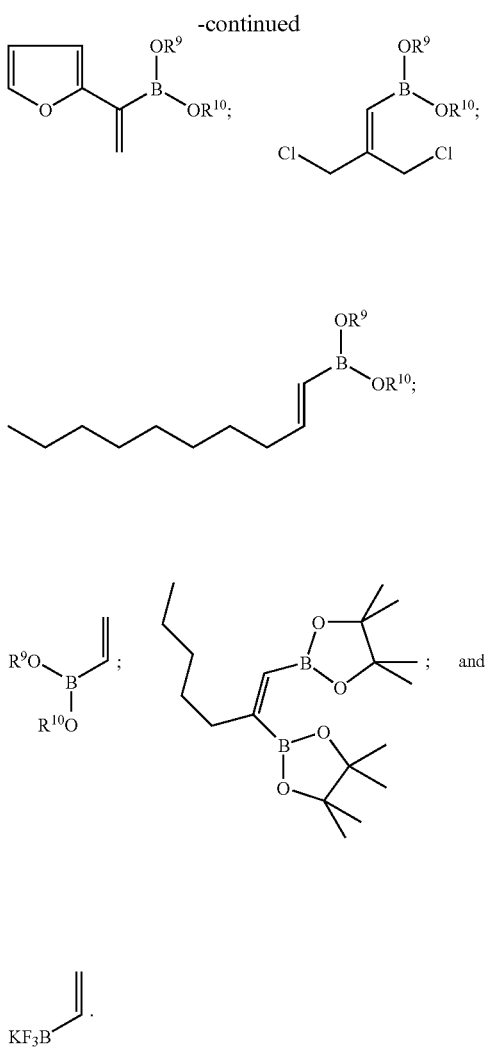

Biological Activity

The compounds of the invention have demonstrated HMG Co-A reductase inhibition in standard assays commonly employed by those skilled in the art. (See, e.g., J. of Lipid Research 1998;39:75-84; Analytical Biochemistry, 1991;196:211-214; RR 740-01077 Pharmacology 8 Nov. 1982). Accordingly, such compounds as well as their pharmaceutical compositions and formulations are useful for treating, controlling or preventing inter alia hypercholesterolemia, hyperlipidemia, hypercholesterolemia, hypertriglyceridemia, atherosclerosis, Alzheimer's Disease, benign prostatic hypertrophy (BPH), diabetes and osteoporosis.

A.) In Vitro Assay

Rat Liver Microsomal Isolation Procedure:

Male Charles River Sprague-Dawley rats were fed with 2.5% cholestyramine in rat chow diets for 5 days before sacrificing. Livers were minced and homogenized in a sucrose homogenizing solution in an ice bath 10 times. Homogenates were diluted into a final volume of 200 mL, and centrifuged 15 min. with a Sorvall Centrifuge at 5° C., 10,000 rpm (12,000×G ). The upper fat layer was removed and the supernatant decanted into fresh tubes. This step was repeated one more time before transferring the supernatant into ultracentrifuge tubes and centrifuged at 36,000 rpm (105,000×G ) for an hour at 5° C. The resulting supernatant was discarded and the pellet was added to total of 15 mL 0.2 M $KH_2PO_4$. Pellets were homogenized gently by hand about 10 times. Samples were pooled and diluted into total of 60 mL buffer. The protein concentration of the homogenate was determined by the Lowry Method using a BCA (Bicinchoninic acid), kit from Pierce Chemical Company. 1 mL aliquots of microsomes were kept frozen in liquid nitrogen.

HMGCoA (3-Hydroxy-3-methylglutaryl CoA) Reductase Assay:

Materials and Methods:

[3-$^{14}$C]-HMGCoA (57.0 mCi/mmol) was purchased from Amersham Biosciences, UK. HMGCoA, mevalonolactone, β-NADPH (β-Nicotinamide Adenine Dinucleotide Phosphate, Reduced form) were purchased from Sigma Chemical Co. AG 1-8X resin was purchased from Bio-Rad Laboratory.

One μL of dimethyl sulfoxide (DMSO) or 1 μL of DMSO containing a test compound at a concentration sufficient to give a final assay concentration of between 0.1 nM to 1 mM was placed into each well of a Corning 96 well plate. A Volume of 34 μL of buffer (100 mM $NaH_2PO_4$, 10 mM Imidazole and 10 mM EDTA), (Ethylenediaminetetraacetic acid) containing with 50 μg/mL rat liver microsomes was added into each well. After incubation for 30 min. on ice, 15 μL of $^{14}$C-HMGCoA (0.024 μCi) with 15 mM NADPH, 25 mM DTT, (Dithiothreitol) was added and incubated at 37° C. for an additional 45 min. The reaction was terminated by the addition of 10 μL of HCl followed by 5 μL of mevalonolactone. Plates were incubated at room temperature overnight to allow lactonization of mevalonate to mevalonolactone. The incubated samples were applied to columns containing 300 μL of AG1-X8 anion exchange resin in a Corning filter plate. The eluates were collected into Corning 96 well capture plates. Scintillation cocktail (Ultima-Flo-M) was added into each well and plates counted on a Trilux Microbeta Counter. The $IC_{50}$ values were calculated with GraphPad software (Prism).

Procedure:

1. Add 1 μL DMSO or compounds into the wells according to the protocol
2. Add 35 μL incubation buffer with the rat microsomes into each well. Incubate 30 min. at 4° C.
3. Add 15 μL $^{14}$C-HMGCoA. Incubate 45 min. at 37° C.
4. Add 10 μL HCl stop reagent
5. Add 5 μL mevelonolactone. Incubate overnight at room temperature
6. Apply the containing into the AG 1-X8 anion exchange resin in Corning filter plate
7. Collect the eluate into Corning capture plate
8. Add scintillation cocktail Ultima-Flo-M
9. Count on a Trilux Microbeta Counter
10. Calculate $IC_{50}$ values Compounds of the invention exhibit a range of $IC_{50}$ values of less than about 500 nM in the aforementioned in vitro assay. Preferably, compounds of the invention exhibit a range of $IC_{50}$ values of less than about 100 nM. More preferably, compounds of the invention exhibit a range of $IC_{50}$ values of less than about 20 nM.

B.) Cell Assay

Protocol for Sterol Biosynthesis in Rat Hepatocytes:

Cell Culture, Compounds Treatment and Cell Labeling:

Frozen rat hepatocytes purchased from XenoTech(cat# N400572) were seeded on 6-well collagen I coated plates at a density of $10^5$ cells/per well. The cells were grown in DMEM, (Dulbecco's Modified Eagle Medium) (Gibco, #11054-020) containing 10% FBS (Fetal Bovine Serum) and 10 mM HEPES, (N-2-hydroxyethyl-piperazine-$N^1$-2-ethane sulfonic acid) (Gibco # 15630-080) for 24 hrs. The cells were pre-incubated with compounds for 4 hrs and then labeled by incubating in medium containing 1 uCi/per mL of $^{14}C$ acetic acid for an additional 4 hrs. After labeling, the cells were washed twice with 5 mM MOPS, (3-[N-morpholino]propane sulfonic acid) solution containing 150 mM NaCl and 1 mM EDTA and collected in the lysis buffer containing 10% KOH and 80% (vol.) ethanol.

Cholesterol Extraction and Data Analysis:

In order to separate labeled cholesterol from labeled non-cholesterol lipids, the cells lysates were subject to saponification at 60° C. for 2 hrs. The lysates were then combined with 0.5 volume of $H_2O$ and 2 volumes of hexane, followed by 30 minutes of vigorous shaking. After the separation of two phases, the upper-phase solution was collected and combined with 5 volumes of scintillation cocktail. The amount of $^{14}C$ cholesterol was quantified by liquid scintillation counting. The $IC_{50}$ values were calculated with GraphPad software (Prism 3.03).

Compounds of the invention exhibit a range of $IC_{50}$ values of less than about 1000 nM in the aforementioned cell assay. Preferably, compounds of the invention exhibit a range of $IC_{50}$ values of less than about 100 nM.

C.) Protocol for Sterol Biosynthesis in L6 Rat Myoblast:

Cell Culture, Compounds Treatment and Cell Labeling:

L6 rat myoblast purchased from ATCC (CRL-1458) were grown in T-150 vented culture flasks and seeded on 12-well culture plates at a density of 60,000 cells per well. The cells were grown in DMEM, (Dulbecco's Modified Eagle Medium) (Gibco, #10567-014) containing 10% heat inactivated FBS (Fetal Bovine Serum) (Gibco # 10082-139) for 72 hours until reaching confluence. The cells were pre-incubated in media with compound and 0.2% DMSO (dimethyl sulfoxide) for 3 hours and then labeled by incubating in medium containing compound, 0.2% DMSO and 1 μCi/per mL of $^{14}C$ acetic acid for an additional 3 hours. After labeling, the cells were washed once with 1×PBS (Gibco #14190-144) then lysed overnight at 4° C. in buffer containing 10% KOH and 78% (vol.) ethanol.

Cholesterol Extraction and Data Analysis:

Lipid ester bonds were hydrolyzed by saponification of the lysates at 60° C. for 2 hours. Sterols (including cholesterol) were extracted from saponified lysates by combining with 3 volumes of hexane and mixing by pipette 6 times. The upper organic phase solution was collected and combined with an equal volume of 1N KOH in 50% methanol and mixed by pipette 6 times. The upper organic phase was collected in a scintilant-coated plate (Wallac #1450-501) and hexanes removed by evaporation at room temperature for 3 hours. The amount of $^{14}C$ cholesterol was quantified by scintillation counting in a Trilux 1450 plate reader (Wallac). The $IC_{50}$ values were calculated from % inhibitions relative to negative controls vs. compound concentration on Microsoft excel 2000 data analysis wizard using a sigmoid inhibition curve model with formula:

$$y = B\max(1 - (x^n/K^n + x^n)) + y2$$

Where K is the $IC_{50}$ for the inhibition curve, X is inhibitor concentration, Y is the response being inhibited and Bmax+Y2 is the limiting response as X approaches zero.

Compounds of the invention have a L6 $IC_{50}$ value greater than about 100 nM in the aforementioned L6 Rat Myoblast. Preferably, compounds of the invention exhibit a hepatocyte selectivity greater than about ((L6 $IC_{50}$/Rat hepatocyte $IC_{50}$) >1000), and have a L6 $IC_{50}$ value greater than about 1000 nM.

EXAMPLES

Example 1

(3R,5R)-7-.5-benzylcarbamoyl-2-(4-fluoro-phenyl)-4-isopropyl-2H-pyrazol-3-yl]-3,5-dihydroxy-heptanoic-acid sodium salt

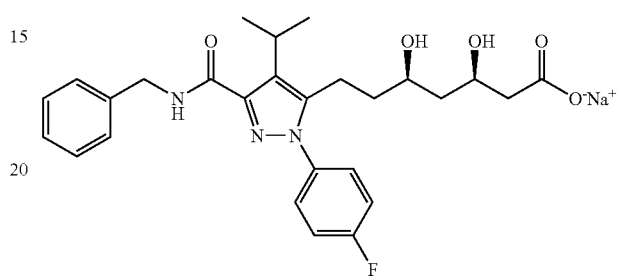

(a) Step A. Preparation of [(4-Fluoro-phenyl)-hydrazonol-chloroacetic acid methyl ester

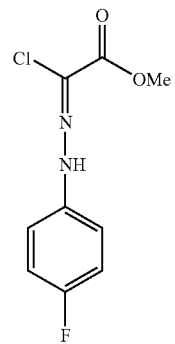

(Reference: *Tetrahedron Asymmetry* 1999, 4447-4454): To a solution of 4-fluoroaniline (10.0 g, 90.0 mmol; commercially available from Sigma Aldrich) in MeOH (80 mL) was added 6 N HCl (80 mL) and the solution was cooled to 0° C. $NaNO_2$ (12.4 g, 180 mmol) was then slowly added as a solid. The reaction was stirred for 15 min at 0° C. after which time NaOAc was added as a solid to adjust the reaction to pH 5. Subsequently, a solution of methyl 2-chloroacetoacetate (10.96 mL, 90.0 mmol; commercially available from Sigma Aldrich) in MeOH (40 mL) was slowly added at 0° C. The reaction was then allowed to warm to 25° C. and stirred for 12 hr after which time the MeOH was removed under reduced pressure and ether (300 mL) was added. The organic layer was separated and washed with saturated $NaHCO_3$ and water prior to drying over $Na_2SO_4$. The organic layer was concentrated to afford [(4-fluoro-phenyl)-hydrazono]-chloroacetic acid methyl ester (19.42 g, 94%) that was utilized without further purification: H-NMR ($CDCl_3$) δ 8.37 (bs, 1 H), 7.22-7.12 (m, 2 H), 7.00-6.96 (m, 2 H), 3.87 (s, 3 H).

(b) Step B. Preparation of 4-Methyl-pent-2-enoic acid benzyl ester

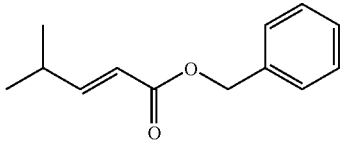

To a solution of 4-methyl-2-pentenoic acid (24.0 g, 210 mmol; commercially available from TCI America) in acetone (300 mL) was added $K_2CO_3$ (55.8 g, 404 mmol) and the reaction was stirred at 25° C. for 30 min. A solution of benzyl bromide (25.2 mL, 212 mmol; commercially available from Sigma Aldrich) in acetone (100 mL) was then added dropwise. The reaction mixture was subsequently heated to reflux for 16 hrs. After cooling to 25° C., the acetone was removed under reduced pressure and ether (300 mL) and water (300 mL) were added and the organic layer was separated, washed with brine and dried over $Na_2SO_4$. After concentration, the crude product was subjected to silica gel chromatography (1-5% Ether/Hex) to afford 4-methyl-pent-2-enoic acid benzyl ester (40.5 g, 98%): H-NMR ($CDCl_3$) δ 7.36-7.28 (m, 5 H), 6.96 (dd, 1 H), 5.79 (d, 1 H), 5.14 (s, 2 H), 2.45-2.40 (m, 1 H), 1.01 (d, 6 H).

(c) Step C. Preparation of 1-(4-fluoro-phenyl)-4-isopropyl-4,5-dihydro-1H-pyrazole-3,5-dicarboxylic acid 5-benzyl ester 3-methyl ester

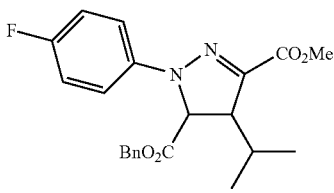

To a solution of [(4-fluoro-phenyl)-hydrazono]-chloroacetic acid methyl ester (20.93 g, 90.8 mmol) and 4-methyl-pent-2-enoic acid benzyl ester (18.54 g, 90.8 mmol) in dioxane (400 mL) at 25° C. was added $Ag_2CO_3$ (63.0 g, 227 mmol; commercially available from Sigma Aldrich). The reaction was protected from light and stirred at 25° C. for 48 hr. Subsequently, the reaction mixture was filtered through a pad of celite and the filtrate was concentrated. The crude product mixture was subjected to silica gel chromatography (5-20% EtOAc/Hex) to afford 1-(4-fluoro-phenyl)-4-isopropyl-4,5-dihydro-1H-pyrazole-3,5-dicarboxylic acid 5-benzyl ester 3-methyl ester in approximately 90% purity (29.3 g, 73%):: H-NMR ($CDCl_3$) δ 7.30-7.24 (m, 3 H), 7.15-7.12 (m, 2 H), 7.01-6.96 (m, 2 H), 6.93-6.88 (m, 2 H), 5.14 (d, 1 H), 4.58 (d, 1 H), 3.83 (s, 3 H), 3.51-3.49 (m, 1 H), 2.40-2.36 (m, 1 H), 1.00 (d, 3 H), 0.69 (d, 3 H).

(d) Step D. Preparation of 1-(4-fluoro-phenyl)-4-isopropyl-1H-pyrazole-3,5-dicarboxylic acid 5-benzyl ester 3-methyl ester

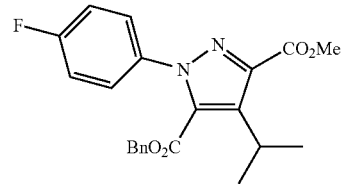

To a solution of 1-(4-fluoro-phenyl)-4-isopropyl-4,5-dihydro-1H-pyrazole-3,5-dicarboxylic acid 5-benzyl ester 3-methyl ester (29.3, 73.5 mmol) in THF:Water (1:1, 500 mL) at 0° C. was slowly added ceric ammonium nitrate (80.5 g, 147 mmol; commercially available from Sigma Aldrich). The reaction was stirred at 0° C. for 1 hr after which time the THF was removed under reduced pressure and DCM (500 mL) was added. The organic layer was separated and washed with water and brine. The organic layer was dried over $Na_2SO_4$ and concentrated, and the product was purified by silica gel chromatography (5-15% EtOAc/Hex) to provide 1-(4-fluoro-phenyl)-4-isopropyl-1H-pyrazole-3,5-dicarboxylic acid 5-benzyl ester 3-methyl ester (18.95 g, 65%):: H-NMR ($CDCl_3$) δ 7.29-7.21 (m, 5 H), 7.07 (d, 2 H), 6.94 (t, 2 H), 5.12 (s, 2 H), 3.89 (s, 3 H), 3.88-3.80 (m, 1 H), 1.31 (d, 6 H).

(e) Step E. Preparation of 1-(4-fluoro-phenyl)-4-isopropyl-1H-pyrazole-3,5-dicarboxylic acid 3-methyl ester

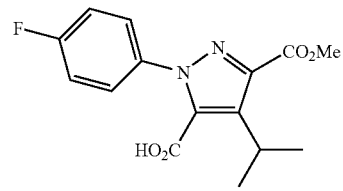

To a solution of 1-(4-fluoro-phenyl)-4-isopropyl-1H-pyrazole-3,5-dicarboxylic acid 5-benzyl ester 3-methyl ester (18.95 g, 47.8 mmol) in MeOH (300 mL) at 25° C. under $N_2$ was added 10% Pd—C (700 mg; commercially available from Sigma Aldrich). The reaction vessel was evacuated and filled with $H_2$ and then stirred at 25° C. for 3 hrs. Subsequently, the reaction vessel was flushed with $N_2$ and filtered through a pad of celite. The filtrate was concentrated to afford 1-(4-fluoro-phenyl)-4-isopropyl-1H-pyrazole-3,5-dicarboxylic acid 3-methyl ester (14.6g, 99%) in sufficient purity for use in the next step: H-NMR ($CDCl_3$) δ 7.36-7.31 (m, 2 H), 7.11-7.06 (m, 2 H), 3.90 (s, 3 H), 3.86-3.82 (m, 1 H), 1.43 (d, 6 H).

(f) Step F. Preparation of 1-(4-fluoro-phenyl)-5-hydroxymethyl-4-isopropyl-1H-pyrazole-3-carboxylic acid methyl ester

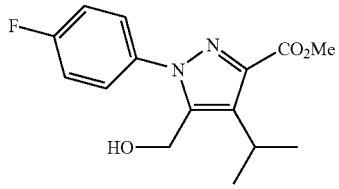

(Reference: *J. Med. Chem.* 1996, 549-555) To a solution of 1-(4-fluoro-phenyl)-4-isopropyl-1H-pyrazole-3,5-dicarboxylic acid 3-methyl ester (15.9 g, 51.8 mmol) in THF (300 mL) at 0° C. was slowly added $BH_3$.THF (1.0 M solution in THF, 104 mL, 104 mmol; commercially available from Sigma Aldrich). The reaction was allowed to warm to 25° C. for 30 min and then heated to 65° C. for 3 hr. After cooling to 25° C., MeOH (50 mL) was slowly added. Subsequently, the solvent was removed under reduced pressure and a second portion of MeOH (100 mL) was slowly added and the solution was stirred at 25° C. for an additional 20 min. The MeOH was then evaporated and EtOAc was added and the organic layer was washed with 1N NaOH and brine prior to drying over $Na_2SO_4$. The organic layer was concentrated and purified by silica gel chromatography (15-35% EtOAc/Hex) to provide 1-(4-fluoro-phenyl)-5-hydroxymethyl-4-isopropyl-1H-pyrazole-3-carboxylic acid methyl ester (13.6 g, 90%): H-NMR ($CDCl_3$) δ 7.59-7.56 (m, 2 H), 7.15-7.11 (m, 2 H), 4.57 (s, 2 H), 3.89 (s, 3 H), 3.66-3.62 (m, 1 H), 1.36 (d, 6 H).

(g) Step G. Preparation of 1-(4-fluoro-phenyl)-5-formyl-4-isopropyl-1H-pyrazole-3-carboxylic acid methyl ester

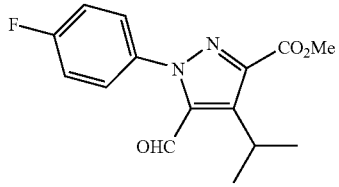

To a solution of 1-(4-fluoro-phenyl)-5-hydroxymethyl-4-isopropyl-1H-pyrazole-3-carboxylic acid methyl ester (13.6 g, 46.7 mmol) in $CH_2Cl_2$ (300 mL) at 25° C. was added solid $NaHCO_3$ (19.6 g, 233 mmol) followed by Dess Martin reagent (20.8 g, 49.0 mmol; commercially available from Lancaster). The reaction was stirred at 25° C. for 4 hr after which time saturated sodium bisulfite (50 mL) was added and the organic layer was separated and washed with water and brine. The organic layer was dried over $Na_2SO_4$ and concentrated to an oil that was purified by silica gel chromatography (15% EtOAc/Hex) to afford 1-(4-fluoro-phenyl)-5-formyl-4-isopropyl-1H-pyrazole-3-carboxylic acid methyl ester (11.3 g, 84%): H-NMR ($CDCl_3$) δ 9.95 (s, 1 H), 7.42-7.38 (m, 2 H), 7.17-7.13 (m, 2 H), 4.01-3.96 (m, 1 H), 3.92 (s, 3 H), 1.38 (d, 6 H).

(h) Step H. Preparation of 1-(4-fluoro-phenyl)-5-formyl-4-isopropyl-1H-pyrazole-3-carboxylic acid

To a solution of 1-(4-fluoro-phenyl)-5-formyl-4-isopropyl-1H-pyrazole-3-carboxylic acid methyl ester (11.34 g, 39.1 mmol) in MeOH (150 mL) was added NaOH (156 mL of 1 N solution, 156 mmol). The reaction was heated to 60° C. for 4 hr. The solvent was then removed under reduced pressure and water (150 mL) and $Et_2O$ (100 mL) were added. The organic layer was discarded and the aqueous layer was acidified with 10% HCl to pH 1 and then extracted with EtOAc (200 mL×2). The combined organic extracts were dried over $Na_2SO_4$ and concentrated to give 1-(4-fluoro-phenyl)-5-formyl-4-isopropyl-1H-pyrazole-3-carboxylic acid (8.55 g, 79%) as a white solid that required no purification: MS($APCI^+$): m/z 277.0 (M+H).

(i) Step I. Preparation of 1-(4-Fluoro-phenyl)-5-formyl-4-isopropyl-1H-pyrazole-3-carboxylic acid benzylamide

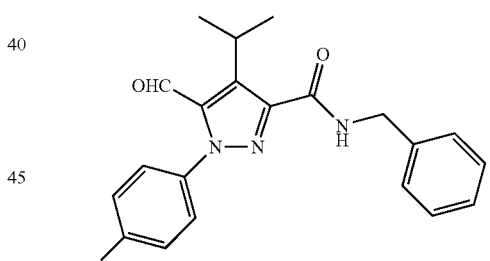

To a solution of 1-(4-fluoro-phenyl)-5-formyl-4-isopropyl-1H-pyrazole-3-carboxylic acid (1.25 g, 4.52 mmol) in $CH_2Cl_2$ (50 mL) at 25° C. was added 1-(3-dimethylaminopropyl)-3-ethylcarbodiimide hydrochloride (1.30 g, 6.79 mmol; commercially available from Sigma Aldrich) followed by 1-hydroxybenzotriazole hydrate (1.04 g, 6.79 mmol; commercially available from Sigma Aldrich) and the reaction was stirred for 5 min at 25° C. Subsequently, benzyl amine (0.533 g, 4.98 mmol; commercially available from Sigma Aldrich) was added and the reaction was stirred for an additional 4 hrs as a fine white precipitate developed. The organic layer was washed with 1 N HCl, saturated $NaHCO_3$ and brine. After drying and concentration, the product was purified by silica gel chromatography (20% EtOAc/Hex) to provide 1-(4-fluoro-phenyl)-5-formyl-4-isopropyl-1H-pyrazole-3-carboxylic acid benzylamide (0.65 g, 39%): MS($APCI^+$): m/z 366.1 (M+H).

(j) Step J. Preparation of 1-(4-Fluoro-phenyl)-5-hydroxymethyl-4-isopropyl-1H-pyrazole-3-carboxylic acid benzylamide

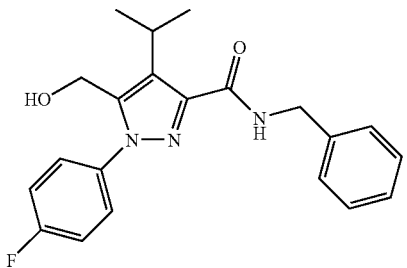

To a solution of 1-(4-fluoro-phenyl)-5-formyl-4-isopropyl-1H-pyrazole-3-carboxylic acid benzylamide (0.620 g, 1.70 mmol) in THF:MeOH (40 mL) at 0° C. was added sodium borohydride (96.3 mg, 2.55 mmol; commercially available from Sigma Aldrich). The reaction was stirred for 30 min at 0° C. at which point TLC analysis indicated the reaction was complete and the solvent was removed under reduced pressure. To the reaction residue was added ethyl acetate (50 mL) and saturated NaHCO$_3$ (15 mL), and the organic layer was separated, dried (Na$_2$SO$_4$) and concentrated. The resulting oil was purified by silica gel chromatography (40% EtOAc/Hex) to afford 1-(4-fluoro-phenyl)-5-hydroxymethyl-4-isopropyl-1H-pyrazole-3-carboxylic acid benzylamide (0.540 g, 87%): MS(APCI$^+$): m/z368.1 (M+H).

(k) Step K. Preparation of [5-Benzylcarbamoyl-2-(4-fluoro-phenyl)-4-isopropyl-2H-pyrazol-3-ylmethl]-triphenyl-phosphonium bromide

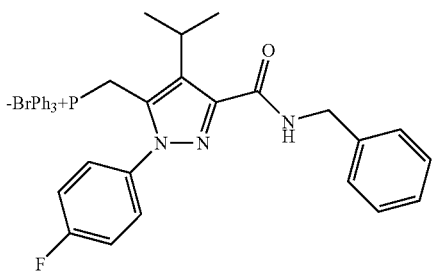

To a solution of 1-(4-fluoro-phenyl)-5-hydroxymethyl-4-isopropyl-1H-pyrazole-3-carboxylic acid benzylamide (0.525 g, 1.43 mmol) in acetonitrile (50 mL) was added triphenylphosphine hydrobromide (0.49 g, 1.43 mmol; commercially available from Sigma Aldrich). The reaction was heated to 80° C. for 24 hr after which time all starting material was consumed as determined by TLC. The reaction solvent was removed under reduced pressure and the resulting white solid was dried under high vacuum for 12 hr to provide [5-benzylcarbamoyl-2-(4-fluoro-phenyl)-4-isopropyl-2H-pyrazol-3-ylmethyl]-triphenyl-phosphonium bromide (0.977 g, 98%) in sufficient purity for use in the next step.

(l) Step L. Preparation of (6-{2-[5-Benzylcarbamoyl-2-(4-fluoro-phenyl)-4-isopropyl-2H-pyrazol-3-yl]-vinyl}-2,2-dimethyl-[1 R,3R]dioxan-4-yl)-acetic acid tert-butyl ester

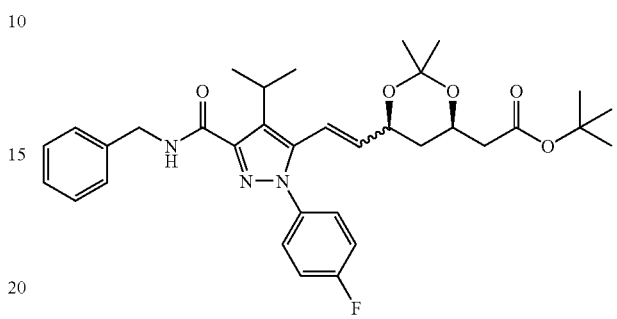

To a solution of [5-benzylcarbamoyl-2-(4-fluoro-phenyl)-4-isopropyl-2H-pyrazol-3-ylmethyl]-triphenyl-phosphonium bromide (0.562 g, 0.811 mmol) in THF:DMSO (50:1, 50 mL) at −78° C. was added 1.0 M LiHMDS (Lithium Hexamethyldisilazide; 1.055 mL, 1.055 mmol; commercially available from Sigma Aldrich). An orange color was noted as the base was added. The reaction mixture was stirred at −78° C. for 5 min after which time a solution of (6-formyl-2,2-dimethyl-[1,3]dioxan-4-yl)-acetic acid tert-butyl ester (0.252 g, 0.974 mmol; *Tetrahedron Lett.*, 1990, 31,2545-2548) in THF (10 mL) was slowly added. After the addition, the reaction mixture was stirred at −78° C. for 30 min then allowed to warm to 25° C. and stirred at that temperature for 5 hr. The reaction was quenched by drop-wise addition of saturated NH$_4$Cl. Ethyl acetate (50 mL) was then added and organic layer was separated, washed with water, dried (Na$_2$SO$_4$), concentrated. The crude product was purified by silica gel chromatography (15-20% EtOAc/Hex) to afford (6-12-[5-benzylcarbamoyl-2-(4-fluoro-phenyl)-4-isopropyl-2H-pyrazol-3-yl]-vinyl}-2,2-dimethyl-[1R,3R]dioxan-4-yl)-acetic acid tert-butyl ester (0.24 g, 50%) as an inseparable 1:4 mixture cis/trans olefin isomers: MS(APCI$^+$): m/z 592.3 (M+H).

(m) Step M. Preparation of (3R,5R)-7-[5-Benzylcarbamoyl-2-(4-fluoro-phenyl)-4-isopropyl-2H-pyrazol-3-yl]-3,5-dihydroxy-heptanoic acid tert-butyl ester

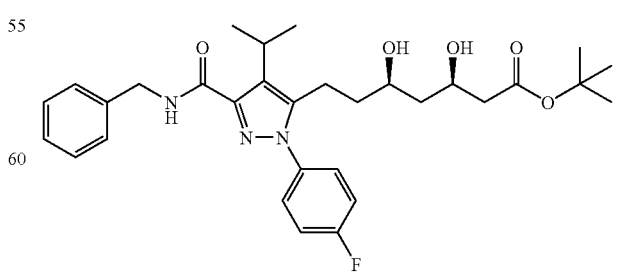

To a solution of (6-{2-[5-benzylcarbamoyl-2-(4-fluoro-phenyl)-4-isopropyl-2H-pyrazol-3-yl}-2,2-dimethyl-[1,3]dioxan-4-yl)-acetic acid tert-butyl ester (0.360 g, 0.61 mmol) in MeOH (20 mL) was added 1N HCl (2 mL) and the solution was stirred for 3 hrs at 25° C. Subsequently, the reaction solvent was removed under reduced pressure and ethyl acetate (50 mL) and saturated NaHCO₃ (10 mL) were added. The organic layer was separated, washed with brine, dried (Na₂SO₄) and concentrated to afford, after silica gel chromatography (35% EtOAc/Hex), 7-[5-benzylcarbamoyl-2-(4-fluoro-phenyl)-4-isopropyl-2H-pyrazol-3-yl]-3,5-dihydroxy-hept-6-enoic acid tert-butyl ester (0.231 g, 69%). Subsequently, to a solution of 7-[5-benzylcarbamoyl-2-(4-fluoro-phenyl)-4-isopropyl-2H-pyrazol-3-yl]-3,5-dihydroxy-hept-6-enoic acid tert-butyl ester (0.241 g, 0.437 mmol) in MeOH (20 mL) was added 10% Pd-C (50 mg; commercially available from Sigma Aldrich), and the reaction vessel was evacuated and filled with hydrogen gas (via balloon) for 3 hours. The reaction mixture was then filtered through a pad of celite and to the filtrate was added The crude product was purified by silica gel chromatography (30-50% EtOAc/Hex) to provide (3R,5R)-7-[5-benzylcarbamoyl-2-(4-fluoro-phenyl)-4-isopropyl-2H-pyrazol-3-yl]-3,5-dihydroxy-heptanoic acid tert-butyl ester (0.143 g, 59%): MS(APCI⁺): m/z554.3 (M+H).

(n) Step N. Preparation of (3R,5R)-7-3,5-benzylcarbamoyl-2-(4-fluoro-phenyl)-4-isopropyl-2H-pyrazol-3-yl]-3,5-dihydroxy-heptanoic acid sodium salt To a solution of 7-[5-benzylcarbamoyl-2-(4-fluoro-phenyl)-4-isopropyl-2H-pyrazol-3-yl]-3,5-dihydroxy-heptanoic acid tert-butyl ester (0.103 g, 0.186 mmol) in MeOH (5 mL) was added 1.0 N NaOH (0.190 mL, 0.195 mmol; commercially available from Sigma Aldrich) and the reaction was stirred at 25° C. for 48 hr after which time the reaction was solvent was removed under reduced pressure. The resulting solid was then azeotroped toluene (3×100 mL) and triturated with diethyl ether to provide a light yellow solid that was dried under vacuum at 60° C. to afford (3R,5R)-7-[5-benzylcarbamoyl-2-(4-fluoro-phenyl)-4-isopropyl-2H-pyrazol-3-yl]-3,5-dihydroxy-heptanoic acid sodium salt (0.091 g, 94%): MS(APCI⁺): m/z498.2 (M+H); H-NMR (DMSO-d₆) δ 8.55 (t, 1 H), 7.53-7.49 (m, 2 H), 7.33-7.13 (m, 7 H), 4.70 (bs, 1 H), 4.34 (d, 1 H), 3.63-3.57 (m, 1 H), 3.45-3.42 (m, 1 H), 2.74-2.66 (m, 1 H), 2.58-2.50 (m, 1 H), 1.95-1.90 (m, 1 H), 1.75-1.69 (m, 1 H), 1.40-1.10 (m, 10 H).

Example 2

(3R,5R)-7-[2-(4-fluoro-phenyl)-4-isopropyl-5-(2-methyl-benzylcarbamoyl)-2H-pyrazol-3,5-dihydroxy-heptanoic acid sodium salt

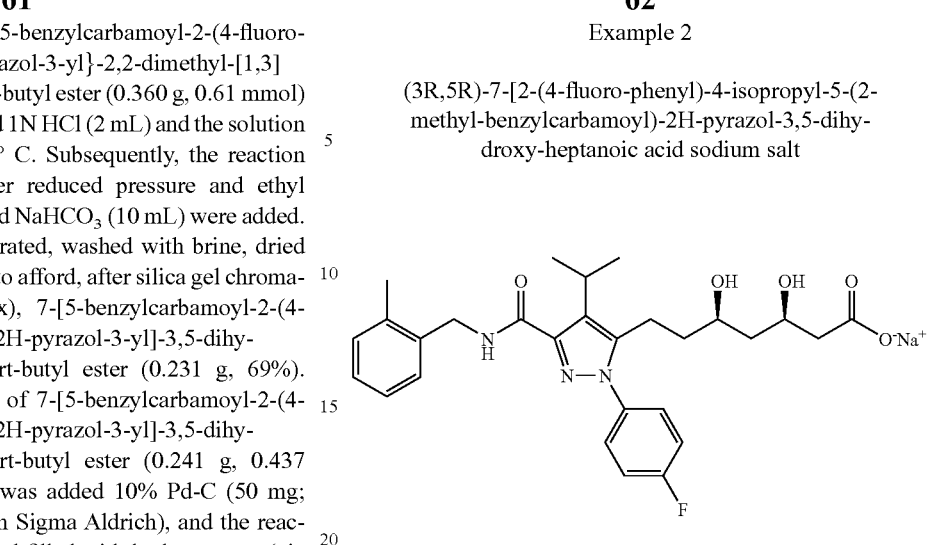

The title compound was prepared in a manner analogous to the method of Example 1. MS(APCI⁺): m/z 510.2 (M–H); H-NMR (DMSO-d₆) δ 7.53-7.50 (m, 2 H), 7.30 (t, 2 H), 7.20-7.17 (m, 1 H), 7.08-7.05 (m, 3 H), 4.33 (s, 3 H), 3.61-3.59 (m, 1 H), 3.45-3.44 (m, 1 H), 3.25 (bs, 1 H), 2.73-2.67 (m, 1 H), 2.58-2.51 (m, 1 H), 2.24 (s, 3 H), 1.94-1.89 (m, 1 H), 1.75-1.69 (m, 1 H), 1.37-1.10 (m, 10 H).

Example 3

(3R,5R)-7-[2-(4-fluoro-phenyl)-4-isopropyl-5-(3-methyl-benzylcarbamoyl)-2H-pyrazol-3]-3,5-dihydroxy-heptanoic acid sodium salt The title compound was prepared in a manner analogous to the method of Example 1: MS(APCI⁺): m/z 512.2 (M+H); H-NMR (DMSO-d₆) δ 7.53-7.49 (m, 2 H), 7.30 (t, 2 H), 7.14-6.95 (m, 4 H)m 4.30 (s, 2 H), 3.62-3.55 (m, 1 H), 3.46-3.42 (m, 1 H), 3.26-3.19 (m, 1 H), 2.69-2.61 (m, 1 H), 2.58-2.51 (m, 1 H), 2.21 (s, 3 H), 1.91-1.88 (m, 1 H), 1.72-1.66 (m, 1 H), 1.34-1.10 (m, 10 H).

The title compound was prepared in a manner analogous to the method of Example 1. MS(APCI⁺): m/z 512.2 (M+H); H-NMR (DMSO-d₆) δ 7.52-7.48 (m, 2 H), 7.29 (t, 2 H), 7.10 (d, 2 H), 7.02 (d, 2 H), 4.29 (s, 2 H), 3.62-3.56 (m, 1 H), 3.45-3.42 (m, 1 H), 3.28 (bs, 1 H), 2.73-2.66 (m, 1 H), 2.57-2.51 (m, 1 H), 2.20 (s, 3 H), 1.92-1.88 (m, 1 H), 1.73-1.67 (m, 1 H), 1.53-1.11 (m, 10 H).

Example 5

(3R,5R)-7-[2-(4-fluoro-phenyl)-4-isopropyl-5-(2-methyl-benzylcarbamoyl)-2H-pyrazol-3-yl]-3,5-dihydroxy-hept-6-enoic acid sodium salt

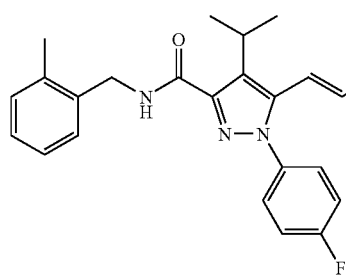

The title compound was prepared in a manner analogous to the method of Example 1. MS(APCI$^+$): m/z 510.3 (M+H); H-NMR (DMSO-d$_6$) δ 8.50 (t, 1 H), 7.53-7.46 (m, 3 H), 7.31 (t, 2 H), 7.20-7.18 (m, 1 H), 7.08-7.06 (m, 3 H), 6.28 (d, 1 H), 5.69 (dd, 1 H), 4.35 (d, 2 H), 4.19-4.17 (m, 1 H), 3.62-3.60 (m, 1 H), 2.26 (s, 3 H), 1.98-1.93 (m, 1 H), 1.78-1.72 (m, 1 H), 1.44-1.18 (m, 8 H).

Example 6

(3R,5R)-7-[2-(4-fluoro-phenyl)-4-isopropyl-5-(4-methyl-benzylcarbamoyl)-2H-pyrazol-3-yl]-3,5-dihydroxy-hept-6-enoic acid sodium salt

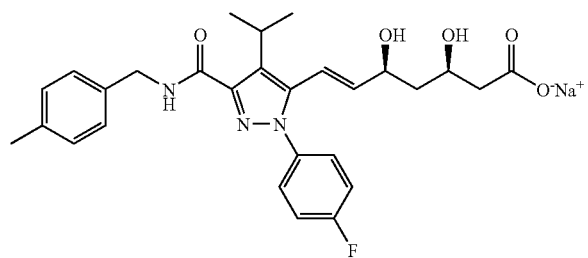

The title compound was prepared in a manner analogous to the method of Example 1. MS(APCI$^+$): m/z 510.2 (M+H); H-NMR (DMSO-d$_6$) δ 8.57 (t, 1 H), 7.54-7.48 (m, 3 H), 7.32-7.28 (m, 2 H), 7.15-7.13 (m, 2 H), 7.06-7.04 (m, 2 H), 6.27 (d, 1 H), 5.68 (dd, 1 H), 5.17 (bs, 1 H), 4.32 (d, 2 H), 4.18-4.17 (m, 1 H), 3.62-3.58 (m, 1 H), 2.21 (s, 3 H), 1.96-1.91 (m, 1 H), 1.77-1.71 (m, 1 H), 1.48-1.41 (m, 1 H), 1.29-1.23 (m, 7 H).

Example 7

(3R,5R)-7-[2-(4-fluoro-phenyl)-4-isopropyl-5-(3-methoxy-benzylcarbamoyl)-2H-pyrazol-3-yl]-3,5-dihydroxy-heptanoic acid sodium salt

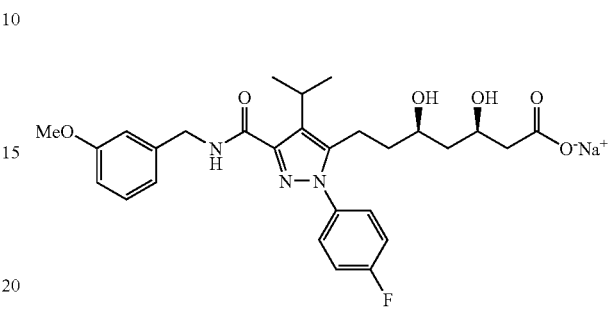

The title compound was prepared in a manner analogous to the method of Example 1. MS(APCI$^+$): m/z 528.2 (M+H); H-NMR (DMSO-d$_6$) δ 7.52-7.49 (m, 2 H), 7.30 (t, 2 H), 7.16-7.12 (m, 1 H), 6.84-6.81 (m, 2 H), 6.72-6.70 (m, 1 H), 4.31 (s, 2 H), 3.66 (s, 3 H), 3.62-3.57 (m, 1 H), 3.47-3.43 (m, 1 H), 3.29-3.18 (m, 2 H), 2.70-2.66 (m, 1 H), 2.56-2.54 (m, 1 H), 1.92-1.88 (m, 1 H), 1.72-1.67 (m, 1 H), 1.36-1.10 (m, 10 H).

Example 8

(3R,5R)-7-[2-(4-fluoro-phenyl)-4-isopropyl-5-(4-methoxy-benzylcarbamoyl)-2H-pyrazol-3-yl]-3,5-dihydroxy-heptanoic acid sodium salt The title compound was prepared in a manner analogous to the method of Example 1. MS(APCI$^+$): m/z 528.2 (M+H); H-NMR (DMSO-d$_6$) δ 7.51-7.48 (m, 2 H), 7.32-7.28 (m, 2 H), 7.21-7.16 (m, 3 H), 6.80 (d, 2 H), 4.27 (s, 2 H), 3.65 (s, 3 H), 3.64-3.49 (m, 3 H), 2.73-2.69 (m, 1 H), 2.57-2.49 (m, 1 H), 1.96-1.92 (m, 1 H), 1.77-1.71 (m, 1 H), 1.37-1.10 (m, 10 H).

Example 9

(3R,5R)-7-[2-(4-fluoro-phenyl)-4-isopropyl-5-(3-methoxy-benzylcarbamoyl)-2H-pyrazol-3-yl]-3,5-dihydroxy-hept-6-enoic acid sodium salt

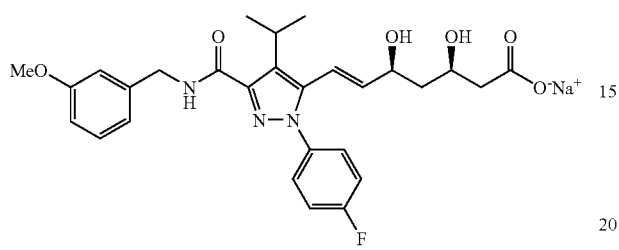

The title compound was prepared in a manner analogous to the method of Example 1: MS(APCI+): m/z 526.3 (M+H); H-NMR (DMSO-d$_6$) δ 8.63 (t, 1 H), 7.52-7.49 (m, 2 H), 7.34-7.28 (m, 3 H), 7.19-7.10 (m, 2 H), 6.83-6.82 (m, 2 H), 6.73 (d, 1 H), 6.28 (dd, 1 H), 5.73-5.69 (m, 1 ), 5.15-5.14 (m, 1 H), 4.34 (d, 2 H), 4.19-4.15 (m, 1 H), 3.66 (s, 3 H), 3.62-3.61 (m, 1 H), 1.99-1.94 (m, 1 H), 1.78-1.74 (m, 1 H), 1.49-1.42 (m, 1 H), 1.25-1.19 (m, 7 H).

Example 10

(3R,5R)-7-[2-(4-fluoro-phenyl)-4-isopropyl-5-(4-methoxy-benzylcarbamoyl)-2H-pyrazol-3-yl]-3,5-dihydroxy-hept-6-enoic acid sodium salt

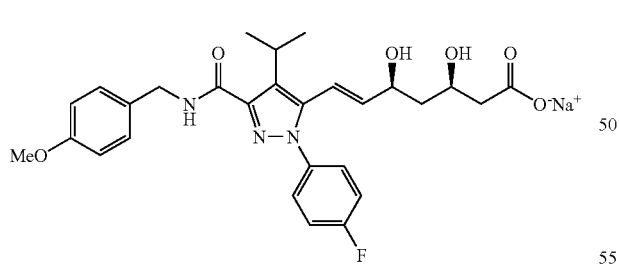

The title compound was prepared in a manner analogous to the method of Example 1: MS(APCI+): m/z 524.1 (M+H); H-NMR (DMSO-d$_6$) δ 8.55 (t, 1 H), 7.52-7.48 (m, 2 H), 7.37 (s, 1 H), 7.30 (t, 2 H), 7.18 (d, 2 H), 6.80 (d, 1 H), 5.68 (dd, 1 H), 5.15 (bs, 1 H), 4.29 (d, 2 H), 4.17-4.15 (m, 1 H), 3.66 (s, 3 H), 3.62-3.58 (m, 1 H), 1.98-1.93 (m, 1 H), 1.79-1.73 (m, 1 H), 1.49-1.42 (m, 1 H), 1.30-1.23 (m, 7 H).

Example 11

(3R,5R)-7-[5-(benzyl-methyl-carbamoyl)-2-(4-fluoro-phenyl)-4-isopropyl-2H-pyrazol-3-yl]-3,5-dihydroxy-heptanoic acid sodium salt

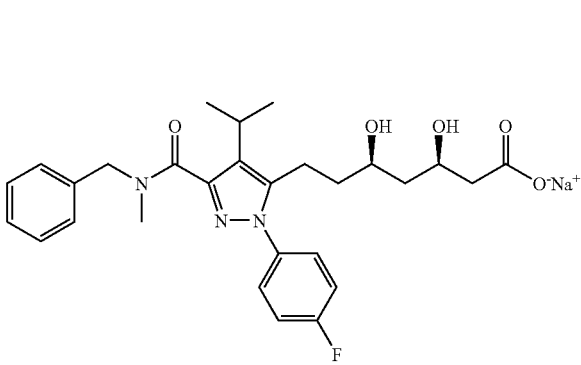

The title compound was prepared in a manner analogous to the method of Example 1 MS(APCI+): m/z 512.1 (M−H); H-NMR (DMSO-d$_6$) δ 7.42-7.06 (m, 9 H), 4.61 (s, 1 H), 4.49 (s, 1 H), 3.87-3.71 (m, 4 H), 3.47-3.42 (m, 1 H), 2.80-2.69 (m, 3 H), 1.97-1.94 (m, 1 H), 1.79-1.75 (m, 1 H), 1.57-1.21 (m, 10 H).

Example 12

(3R,5R)-7-[5-[(3-fluoro-benzyl)-methyl-carbamoyl]-2-(4-fluoro-phenyl)-4-isopropyl-2H-pyrazol-3-yl]-3,5-dihydroxy-heptanoic acid sodium salt

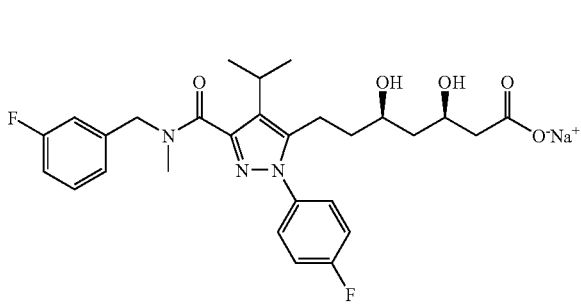

The title compound was prepared in a manner analogous to the method of Example 1: MS(APCI+): m/z 530.3 (M−H); H-NMR (DMSO-d$_6$) δ 7.48-7.01 (m, 8 H), 4.63 (s, 1 H), 4.52 (s, 1 H), 3.62-3.58 (m, 1 H), 3.46-3.44 (m, 1 H), 2.89-2.85 (m, 1 H), 2.83 (s, 3 H), 2.74-2.66 (m, 1 H), 2.54-2.45 (m, 1 H), 1.93-1.88 (m, 1 H), 1.73-1.67 (m, 1 H), 1.53-1.10 (m, 10 H).

Example 13

(3R,5R)-7-[5-(4-fluoro-benzyl)-methyl-carbamoyl]-2-(4-fluoro-phenyl)-4-isopropyl-3-yl]-3,5-dihydroxy-hept-6-enoic acid sodium salt

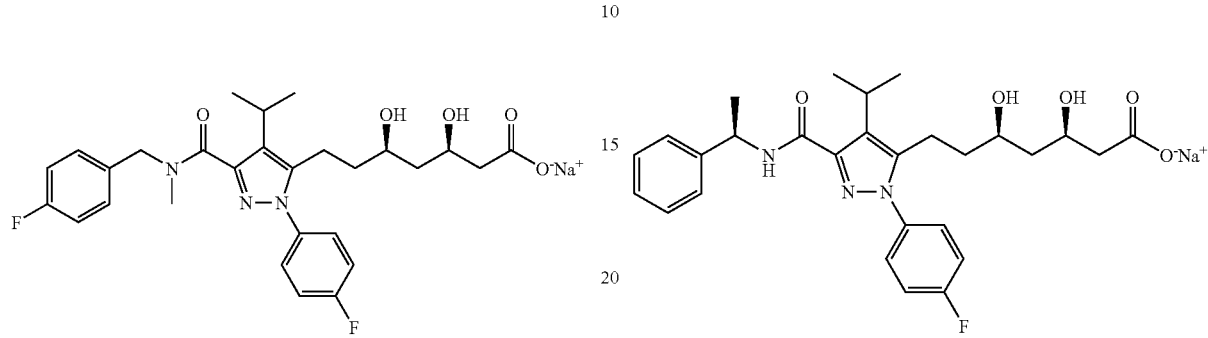

The title compound was prepared in a manner analogous to the method of Example 1: MS(APCI+): m/z 530.2 (M−H); H-NMR (DMSO-$d_6$) δ 7.52-7.08 (m, 8 H), 4.71 (bs, 1 H), 4.60 (s, 1 H), 4.48 (s, 1 H), 3.60-3.58 (m, 1 H), 3.47-3.42 (m, 1 H), 2.89-2.84 (m, 1 H), 2.80 (s, 3 H), 2.73-2.70 (m, 1 H), 2.67-2.58 (m, 1 H), 1.92-1.88 (m, 1 H), 1.72-1.66 (m, 1 H), 1.36-1.26 (m, 3 H), 1.16-1.11 (m, 7 H).

Example 14

(3R,5R)-7-{2-(4-fluoro-phenyl)-4-isopropyl-5-[N-methyl-(R)-α-methyl-benzylcarbamoyl]-2H-pyrazol-3-yl}-3,5-dihydroxy-heptanoic acid sodium salt

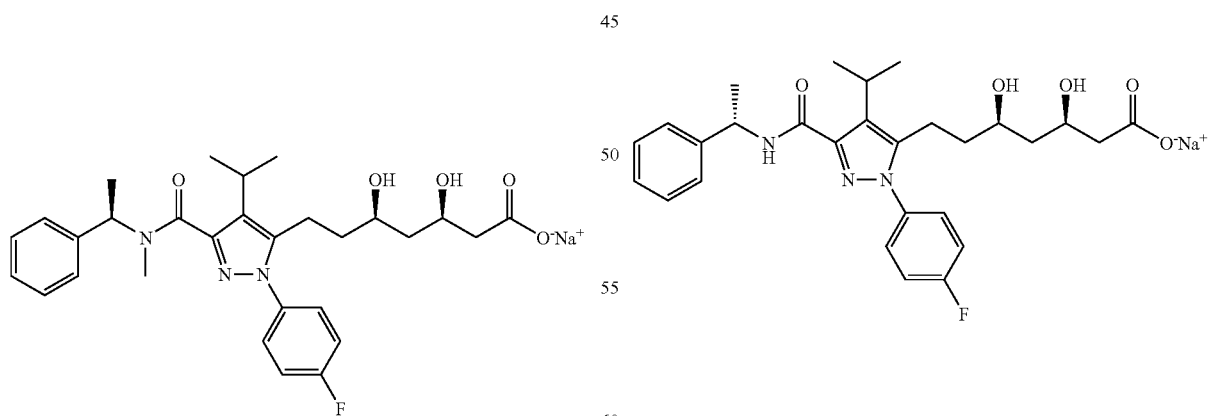

The title compound was prepared in a manner analogous to the method of Example 1: MS(APCI+): m/z 526.22 (M+H).

Example 15

(3R,5R)-7-[2-(4-fluoro-phenyl)-4-isopropyl-5-[(R)-α-methyl-benzylcarbamoyl]-2H-pyrazol-3-yl]-3,5-dihydroxy-heptanoic acid sodium salt The title compound was prepared in a manner analogous to the method of Example 1: MS(APCI+) 512.3 m/z (M+H); H-NMR (DMSO-$d_6$) δ 8.27 (d, 1 H), 7.54-7.50 (m, 2 H), 7.46-7.07 (m, 8 H), 5.11-5.03 (m, 1 H), 4.70 (d, 1 H), 3.65-3.52 (m, 1 H), 3.49-3.38 (m, 1 H), 3.22-3.12 (m, 1H), 2.73-2.65 (m, 1 H), 2.57-2.49 (m, 1 H), 1.94-1.89 (m, 1 H), 1.74-1.68 (m, 1 H), 1.40-1.06 (m, 13 H).

Example 16

(3R,5R)-7-[2-(4-fluoro-phenyl)-4-isopropyl-5-[(S)-α-methyl-benzylcarbamoyl-2H-pyrazol-3-yl]-3,5-dihydroxy-heptanoic acid sodium salt

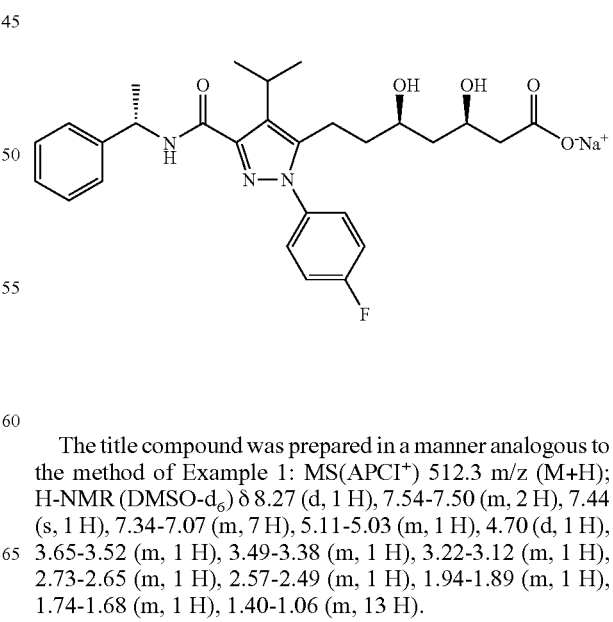

The title compound was prepared in a manner analogous to the method of Example 1: MS(APCI+) 512.3 m/z (M+H); H-NMR (DMSO-$d_6$) δ 8.27 (d, 1 H), 7.54-7.50 (m, 2 H), 7.44 (s, 1 H), 7.34-7.07 (m, 7 H), 5.11-5.03 (m, 1 H), 4.70 (d, 1 H), 3.65-3.52 (m, 1 H), 3.49-3.38 (m, 1 H), 3.22-3.12 (m, 1 H), 2.73-2.65 (m, 1 H), 2.57-2.49 (m, 1 H), 1.94-1.89 (m, 1 H), 1.74-1.68 (m, 1 H), 1.40-1.06 (m, 13 H).

Example 17

(3R,5R)-7-[5-(benzyl-methyl-carbamoyl)-2-(4-fluoro-phenyl)-4-isopropyl-2H-pyrazol-3-yl]-3,5-hept-6-enoic acid sodium salt

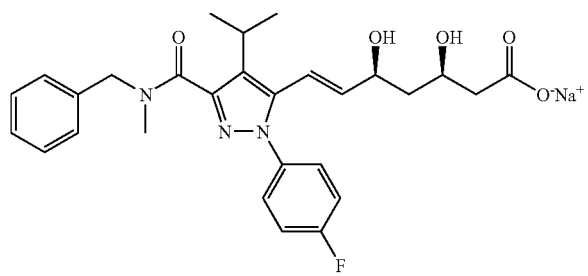

The title compound was prepared in a manner analogous to the method of Example 1:H-NMR (DMSO-$d_6$) δ 7.50-7.17 (m, 9 H), 6.24 (d, 1 H), 5.82 (dd, 1 H), 4.53 (s, 1 H), 4.19-4.18 (m, 1 H), 3.63-3.59 (m, 1 H), 2.97-2.94 (m, 1 H), 2.83 (d, 2 H), 1.96-1.92 (m, 1 H), 1.78-1.72 (m, 1 H), 1.47-1.43 (m, 1 H), 1.35-1.29 (m, 1 H), 1.19-1.10 (m, 6 H).

Example 18

(3R,5R)-7-[2-(4-fluoro-phenyl)-4-isopropyl-5-[(R)-α-methyl-benzylcarbamoyl]-2H-pyrazol-3-yl]-3,5-dihydroxy-hept-6-enoic acid sodium salt

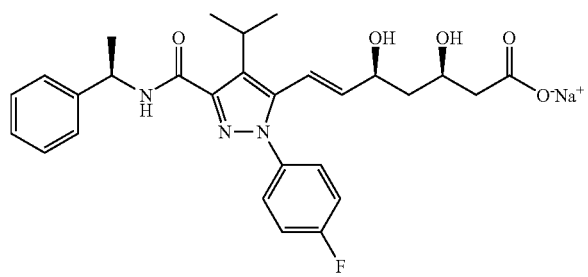

The title compound was prepared in a manner analogous to the method of Example 1: MS(APCI$^+$) m/z 510.3 (M+H); H-NMR (DMSO-$d_6$) δ 8.38 (d, 1 H), 7.53-7.50 (m, 2 H), 7.35-7.09 (m, 8 H), 6.27 (d, 1 H), 5.69 (dd, 1 H), 5.15 (s, 1 H), 5.09 (t, 1 H), 4.18-4.17 (m, 1 H), 3.63-3.57 (m, 1 H), 3.24-3.17 (m, 1H), 1.96 (dd, 1 H), 1.77 (dd, 1 H), 1.54-1.18 (m, 13 H).

Example 19

(3R,5R)-7-[2-(4-fluoro-phenyl)-4-isopropyl-5-[(S)-α-methyl-benzylcarbamoyl]-2H-pyrazol-3-yl]-3,5-dihydroxy-hept-6-enoic acid sodium salt

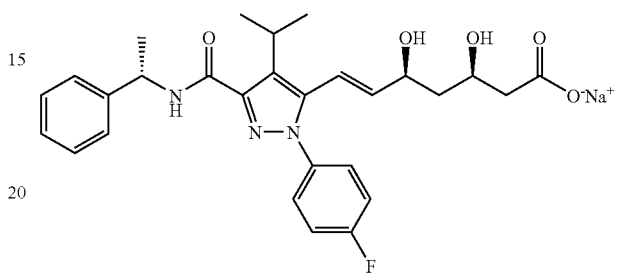

The title compound was prepared in a manner analogous to the method of Example 1: MS(APCI$^+$) 510.3 m/z (M+H); H-NMR (DMSO-$d_6$) δ 8.38 (d, 1 H), 7.54-7.50 (m, 2 H), 7.35-7.09 (m, 8 H), 6.28 (d, 1 H), 5.69 (dd, 1 H), 5.21-5.07 (m, 2 H), 4.17 (q, 1 H), 3.63-3.57 (m, 1 H), 3.24-3.17 (m, 1H), 1.96 (dd, 1 H), 1.77 (dd, 1 H), 1.54-1.18 (m, 13 H).

Example 20

(3R,5R)-7-[2-(4-fluoro-phenyl)-4-isopropyl-5-phenethylcarbamoyl-2H-pyrazol-3-yl]-3,5-dihydroxy-heptanoic acid sodium salt

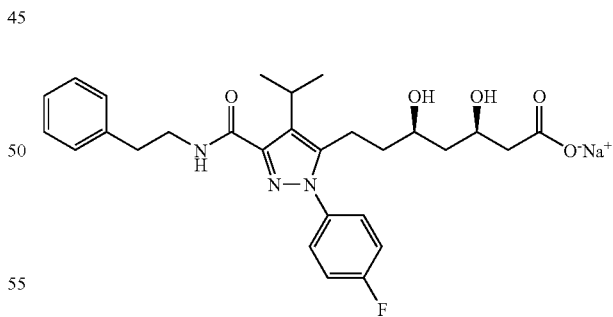

The title compound was prepared in a manner analogous to the method of Example 1: MS(APCI$^+$) 512.6 m/z (M+H); H-NMR (DMSO-$d_6$) δ 8.19-7.95 (m, 1 H), 7.55-7.01 (m, 10 H), 4.78-4.63 (m, 1 H), 3.66-3.51 (m, 1 H), 3.42-3.35 (m, 1 H), 3.26-3.08 (m, 1 H), 2.78-2.60 (m, 1 H), 2.58-2.40 (m, 2 H), 1.98-1.83 (m, 1 H), 1.76-1.63 (m, 1 H), 1.43-1.05 (m, 13 H).

Example 21

(3R,5R)-7-[2-(4-fluoro-phenyl)-4-isopropyl-5-methylcarbamoyl-2H-pyrazol-3-yl]-3,5-dihydroxy-heptanoic acid sodium salt

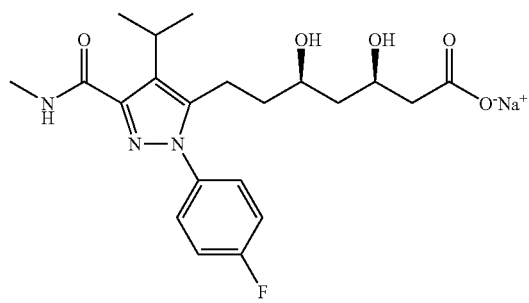

The title compound was prepared in a manner analogous to the method of Example 1: MS(APCI+): m/z 422.2 (M+H); H-NMR (DMSO-d₆) δ 7.96-7.95 (m, 1 H), 7.64 (s, 1 H), 7.51-7.47 (m, 2 H), 7.34-7.28 (m, 2 H), 4.72 (bs, 1 H), 3.59-3.51 (m, 1 H), 3.47-3.42 (m, 1 H), 2.72-2.43 (m, 5 H), 1.91-1.86 (m, 1 H), 1.70-1.64 (m, 1 H), 1.47-1.11 (m, 10H).

Example 22

(3R,5R)-7-[5-ethylcarbamoyl-2-(4-fluoro-phenyl)-4-isopropyl-2H-pyrazol-3-yl]-3,5-dihydroxy-heptanoic acid sodium salt

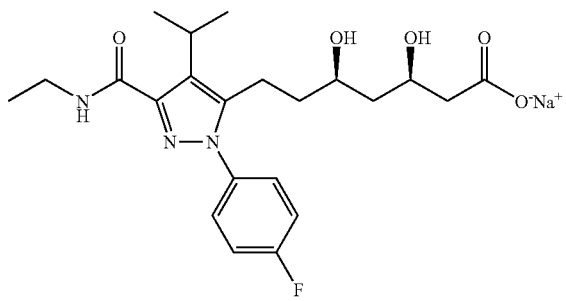

The title compound was prepared in a manner analogous to the method of Example 1: MS(APCI+) 436.6 m/z (M+H); H-NMR (DMSO-d₆) δ 8.09-7.97 (m, 1 H), 7.55-7.45 (m, 2 H), 7.35-7.03 (m, 4 H), 4.78-4.63 (m, 1 H), 3.66-3.55 (m, 1 H), 3.51-3.39 (m, 1 H), 3.26-3.08 (m, 3 H), 2.78-2.60 (m, 1 H), 2.58-2.40 (m, 1 H), 1.98-1.83 (m, 1 H), 1.76-1.63 (m, 1 H), 1.43-1.05 (m, 13 H).

Example 23

(3R,5R)-7-[5-dimethylcarbamoyl-2-(4-fluoro-phenyl)-4-isopropyl-2H-pyrazol-3-yl]-3,5-dihydroxy-heptanoic acid sodium salt

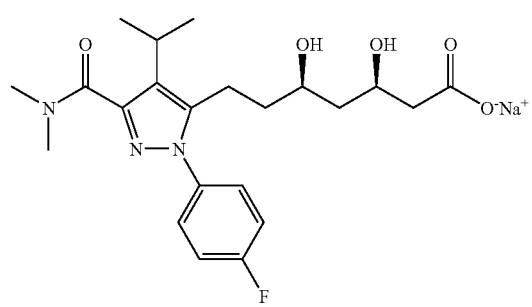

The title compound was prepared in a manner analogous to the method of Example 1: MS(APCI+) 436.3 m/z (M+H); H-NMR (DMSO-d₆) δ 7.55-7.45 (m, 2 H), 7.35-7.03 (m, 4 H), 4.78-4.55 (m, 1 H), 3.66-3.55 (m, 1 H), 3.51-3.39 (m, 1 H), 2.98-2.77 (d, 6 H), 2.78-2.60 (m, 1 H), 2.58-2.40 (m, 1 H), 1.98-1.83 (m, 1 H), 1.76-1.63 (m, 1 H), 1.43-1.05 (m, 10 H).

Examples 24-29

Examples 24-29 can be prepared in a manner analogous to the method of Scheme 2:

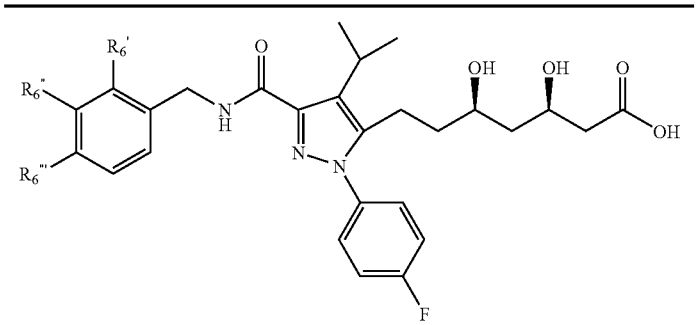

| Ex | Compound | $R_6'$ | $R_6''$ | $R_6'''$ |
|---|---|---|---|---|
| 24 | 7-(5-Benzylcarbamoyl-4-isopropyl-2-(4-fluoro-phenyl)-2H-pyrazol-3-yl)-3R,5R-dihydroxy-heptanoic acid | H | H | H |
| 25 | 3R,5R-Dihydroxy-7-[4-isopropyl-5-(2-methyl-benzylcarbamoyl)-2-(4-fluoro-phenyl)-2H-pyrazol-3-yl]-heptanoic acid | Me | H | H |
| 26 | 3R,5R-Dihydroxy-7-[4-isopropyl-5-(3-methyl-benzylcarbamoyl)-2-(4-fluoro-phenyl)-2H-pyrazol-3-yl]- | H | Me | H |

-continued

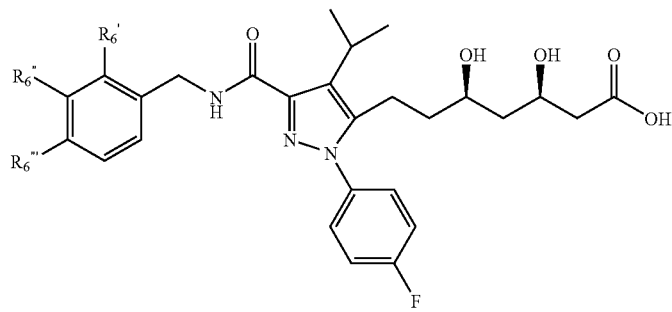

| Ex | Compound | $R_6'$ | $R_6''$ | $R_6'''$ |
|----|----------|--------|---------|----------|
|    | heptanoic acid | | | |
| 27 | 3R,5R-Dihydroxy-7-[4-isopropyl-5-(4-methyl-benzylcarbamoyl)-2-(4-fluoro-phenyl)-2H-pyrazol-3-yl]-heptanoic acid | H | H | Me |
| 28 | 3R,5R-Dihydroxy-7-[4-isopropyl-5-(3-methoxy-benzylcarbamoyl)-2-(4-fluoro-phenyl)-2H-pyrazol-3-yl]-heptanoic acid | H | OMe | H |
| 29 | 3R,5R-Dihydroxy-7-[4-isopropyl-5-(4-methoxy-benzylcarbamoyl)-2-(4-fluoro-phenyl)-2H-pyrazol-3-yl]-heptanoic acid | H | H | OMe |

Examples 30-32

Examples 30-32 can be prepared in a manner analogous to the method of Scheme 2:

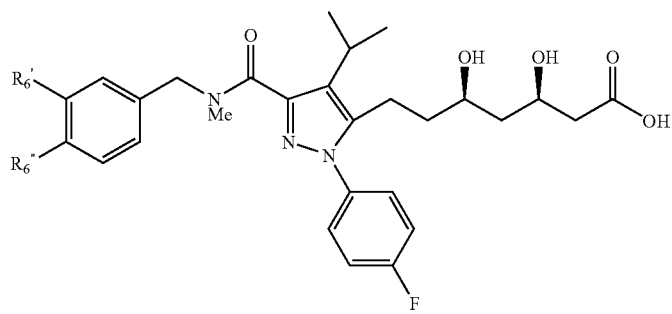

| Ex | Compound | $R_6'$ | $R_6''$ |
|----|----------|--------|---------|
| 30 | 7-[5-(Benzyl-methyl-carbamoyl)-4-isopropyl-2-(4-fluoro-phenyl)-2H-pyrazol-3-yl]-3R,5R-dihydroxy-heptanoic acid | H | H |
| 31 | 7-{5-[(3-Fluoro-benzyl)-methyl-carbamoyl]-4-isopropyl-2-(4-fluoro-phenyl)-2H-pyrazol-3-yl}-3R,5R-dihydroxy-heptanoic acid | F | H |
| 32 | 7-{5-[(4-Fluoro-benzyl)-methyl-carbamoyl]-4-isopropyl-2-(4-fluoro-phenyl)-2H-pyrazol-3-yl}-3R,5R-dihydroxy-heptanoic acid | H | F |

Examples 33-35

Examples 33-35 can be prepared in a manner analogous to the method of Scheme 2:

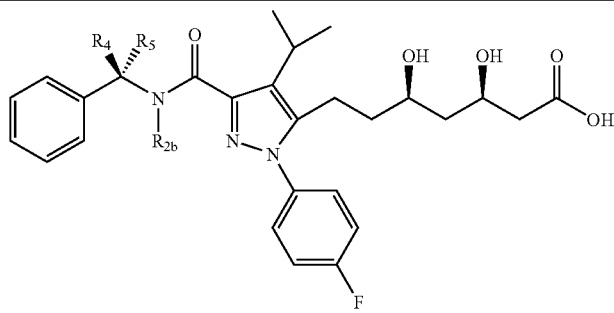

| Ex | Example | $R_{2b}$ | $R_4$ | $R_5$ |
|----|---------|----------|-------|-------|
| 33 | 3R,5R-Dihydroxy-7-[4-isopropyl-2-(4-fluoro-phenyl)-5-[(R)-α-methyl-benzylcarbamoyl]-2H-pyrazol-3-yl]-heptanoic acid | H | Me | H |
| 34 | 3R,5R-Dihydroxy-7-[4-issopropyl-2-(4-fluoro-phenyl)-5-[(S)-α-methyl-benzylcarbamoyl]-2H-pyrazol-3-yl]-heptanoic acid | H | H | Me |
| 35 | 3R,5R-Dihydroxy-7-{4-isopropyl-5-[N-methyl-(R)-α-methyl-benzylcarbamoyl]-2-(4-fluoro-phenyl)-2H-pyrazol-3-yl}-heptanoic acid | Me | Me | H |

Examples 36-39

Examples 36-39 can be prepared in a manner analogous to the method of Scheme 2:

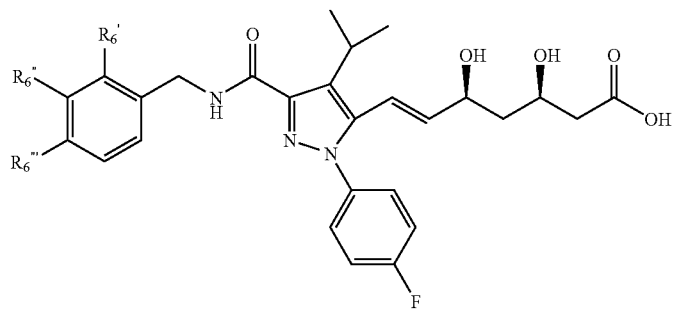

| Ex | Compound | $R_6'$ | $R_6''$ | $R_6'''$ |
|----|----------|--------|---------|----------|
| 36 | 3R,5R-Dihydroxy-7-[4-isopropyl-5-(2-methyl-benzylcarbamoyl)-2-(4-fluoro-phenyl)-2H-0pyrazol-3-yl]-hept-6-enoic acid | Me | H | H |
| 37 | 3R,5R-Dihydroxy-7-[4-isopropyl-5-(4-meethyl-benzylcarbamoyl)-2-(4-fluoro-phenyl)-2H-pyrazol-3-yl]-hept-6-enoic acid | H | H | Me |
| 38 | 3R,5R-Dihydroxy-7-[4-isopropyl-5-(3-methoxy-benzylcarbamoyl)-2-(4-fluoro-phenyl)-2H-pyrazol-3-yl]-hept-6-enoic acid | H | OMe | H |
| 39 | 3R,5R-Dihydroxy-7-[4-isopropyl-5-(4-methoxy-benzylcarbamoyl)-2-(4-fluoro-phenyl)-2H-pyrazol-3-yl]-hept-6-enoic acid | H | H | OMe |

Examples 40-42

Examples 40-42 can be prepared in a manner analogous to the method of Scheme 2:

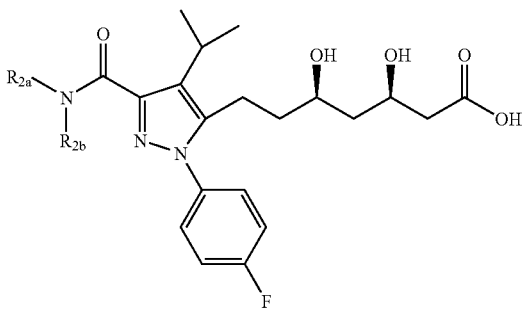

| Ex | Compound | $R_{2a}$ | $R_{2b}$ |
|----|----------|----------|----------|
| 40 | 3R,5R-Dihydroxy-7-(4-isopropyl-5-methylcarbamoyl-2-(4-fluoro-phenyl)-2H-pyrazol-3-yl)-heptanoic acid | Me | H |
| 41 | 7-(5-Ethylcarbamoyl-4-isopropyl-2-(4-fluoro-phenyl)-2H-pyrazol-3-yl)-3R,5R-dihydroxy-heptanoic acid | Ethyl | H |
| 42 | 7-(5-Dimethylcarbamoyl-4-isopropyl-2-(4-fluoro-phenyl)-2H-pyrazol-3-yl)-3R,5R-dihydroxy-heptanoic acid | Me | Me |

Examples 43-45

Examples 43-45 can be prepared in a manner analogous to the method of Scheme 2:

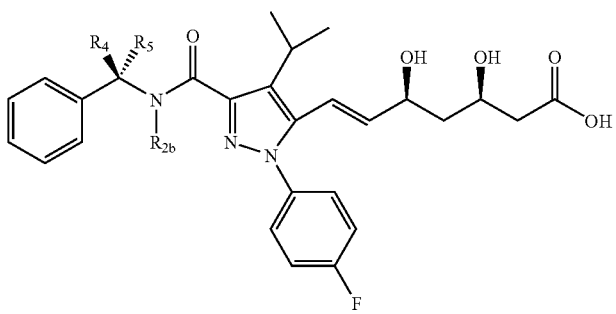

| Ex | Compound | $R_{2b}$ | $R_4$ | $R_5$ |
|----|----------|----------|-------|-------|
| 43 | 7-[5-(Benzyl-methyl-carbamoyl)-4-isopropyl-2-(4-fluoro-phenyl)-2H-pyrazol-3-yl]-3R,5R-dihydroxy-hept-6-enoic acid | Me | H | H |
| 44 | 3R,5R-Dihydroxy-7-[4-isopropyl-2-(4-fluoro-phenyl)-5-[(R)-α-methyl-benzylcarbamoyl]-2H-pyrazol-3-yl]-hept-6-enoic acid | H | Me | H |
| 45 | 3R,5R-Dihydroxy-7-[4-isopropyl-2-(4-fluoro-phenyl)-5-[(S)-α-methyl-benzylcarbamoyl]-2H-pyrazol-3-yl]-hept-6-enoic acid | H | H | Me |

Example 46

(3R,5R)-7-{2-(4-fluoro-phenyl)-4-isopropyl-5-[methyl-(4-methyl-benzyl)-carbamoyl]-2H-pyrazol-3-yl}-3,5-dihydroxy-heptanoic acid sodium salt

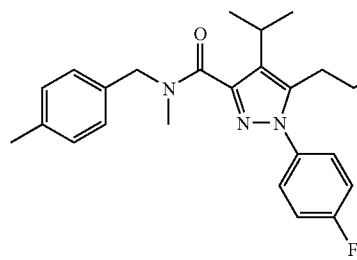

The title compound was prepared in a manner analogous to the method of Example 1: MS(APCI$^+$) 526.3 m/z (M+H); H-NMR (DMSO-d$_6$) [Mixture of rotamers at 25° C.] δ 7.51-7.40, 7.35-7.22, 7.20-7.06, 5.70, 4.71, 4,57, 4,44, 3.65-3.55, 3.47-3.41, 3.11, 2.93-2.83, 2.78, 2.77, 2.68-2.63, 2.60-2.48, 2.46-2.44, 1.93-1.86, 1.75-1.64, 1.42-1.23, 1.05-1.10.

Example 47

(3R,5R)-7-[2-(4-fluoro-phenyl)-4-isopropyl-5-phenylcarbamoyl-2H-pyrazol-3-yl]-3,5-dihydroxy-heptanoic acid sodium salt

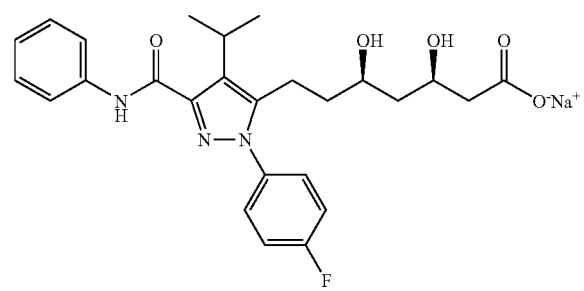

The title compound was prepared in a manner analogous to the method of Example 1: MS(APCI$^+$) 484.2 m/z (M+H); H-NMR (DMSO-d$_6$) δ 9.93 (s, 1 H), 7.75-7.50 (m, 4 H), 7.45-7.23 (m, 5 H), 7.05 (t, 1 H), 5.72 (s, 1 H), 3.68-3.54 (m, 1 H), 3.51-3.41 (m, 1 H), 3.25-3.18 (m, 1 H), 2.80-2.67 (m, 1 H), 2.63-2.51 (m, 1 H), 1.97-1.84 (m, 1 H), 1.76-1.63 (m, 1 H), 1.43-1.13 (m, 10 H).

Example 48

(3R,5R)-7-[5-(3-fluoro-benzylcarbamoyl)-2-(4-fluoro-phenyl)-4-isopropyl-2H-pyrazol-3-yl]-3,5-dihydroxy-heptanoic acid sodium salt

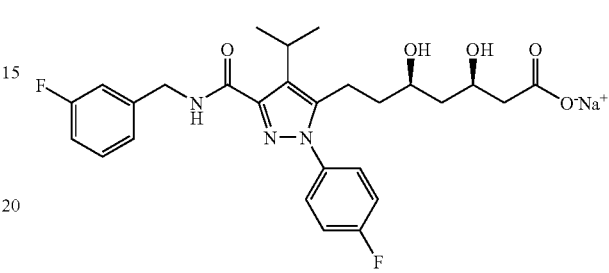

The title compound was prepared in a manner analogous to the method of Example 1: MS(APCI$^+$) 516.2 m/z (M+H); H-NMR (DMSO-d$_6$) δ 7.53-7.50 (m, 2 H), 7.33-7.26 (m, 3 H), 7.09-6.96 (m, 3 H), 4.35 (s, 2 H), 3.60-3.58 (m, 1 H), 3.46-3.43 (m, 1 H), 2.70-2.65 (m, 1 H), 2.55-2.45 (m, 1 H), 1.94 (dd, 1 H), 1.74-1.68 (m, 1 H), 1.37-1.10 (m, 10 H).

Example 49

(3R,5R)-7-[5-(4-fluoro-benzylcarbamoyl)-2-(4-fluoro-phenyl)-4-isopropyl-2H-pyrazol-3-yl]-3,5-dihydroxy-heptanoic acid sodium salt

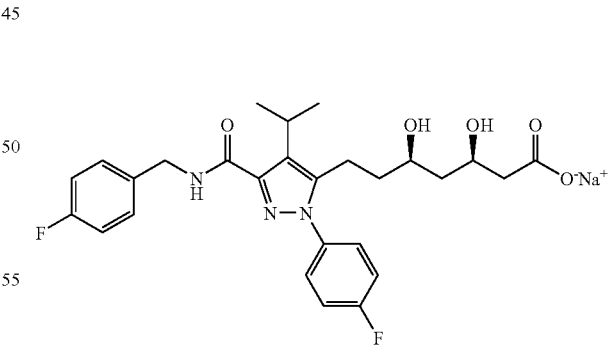

The title compound was prepared in a manner analogous to the method of Example 1: MS(APCI$^+$) 516.3 m/z (M+H); H-NMR (DMSO-d$_6$) δ 7.52-7.48 (m, 2 H), 7.32-7.26 (m, 4 H), 7.08-7.04 (m, 2 H), 4.31 (s, 2 H), 3.61-3.55 (m, 1 H), 3.45-3.42 (m, 1 H), 2.73-2.66 (m, 1 H), 2.57-2.53 (m, 1 H), 1.91-1.87 (m, 1 H), 1.71-1.65 (m, 1 H), 1.35-1.05 (m, 10 H).

Example 50

(3R,5R)-7-[2-(4-fluoro-phenyl)-4-isopropyl-5-(1-methyl-1-phenyl-ethylcarbamoyl)-2H-pyrazol-3-yl]-3,5-dihydroxy-heptanoic acid sodium salt

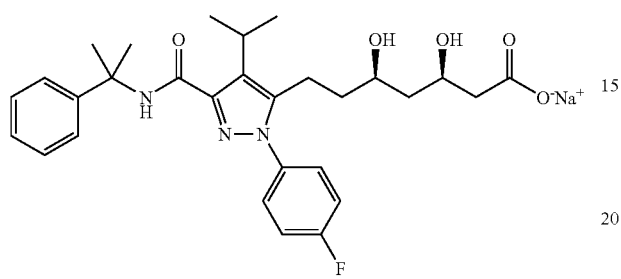

The title compound was prepared in a manner analogous to the method of Example 1: MS(APCI$^+$) 526.3 m/z (M+H); H-NMR (DMSO-d$_6$) δ 7.55-7.51 (m, 2 H), 7.35-7.10 (m, 7 H), 3.61-3.58 (m, 1 H), 3.45-3.43 (m, 1 H), 3.10 (bs, 1 H), 2.57-2.50 (m, 1 H), 2.49-2.44 (m, 1 H), 1.92-1.87 (m, 1 H), 1.72-1.66 (m, 1 H), 1.58 (s, 6 H), 1.34-1.08 (m, 10 H).

Example 51

(3R,5R)-7-[2-(4-fluoro-phenyl)-4-isopropyl-5-(4-methoxymethyl-benzylcarbamoyl)-2H-pyrazol-3-yl]-3,5-dihydroxy-heptanoic acid sodium salt

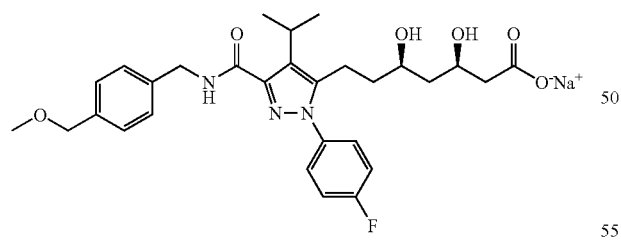

The title compound was prepared in a manner analogous to the method of Example 1: MS(APCI$^+$) 542.3 m/z (M+H); H-NMR (DMSO-d$_6$) δ 7.52-7.49 (m, 2 H), 7.32-7.28 (t, 2 H), 7.23-7.17 (m, 4 H), 4.33 (s, 2 H), 4.31 (s, 2 H), 3.59-3.57 (m, 1 H), 3.45-3.43 (m, 1 H), 3.20 (s, 3 H), 2.57-2.49 (m, 1 H), 2.48-2.42 (m, 1 H), 1.92-1.87 (m, 1 H), 1.71-1.66 (m, 1 H), 1.29-1.09 (m, 10 H).

Example 52

(3R,5R)-7-{2-(4-fluoro-phenyl)-4-isopropyl-5-[(4-methoxy-benzyl)-methyl-carbamoyl]-2H-pyrazol-3-yl}-3,5-dihydroxy-heptanoic acid sodium salt The title compound was prepared in a manner analogous to the method of Example 1: MS(APCI$^+$) 542.3 m/z (M+H); H-NMR (DMSO-d$_6$) [Mixture of rotamers at 25° C.] δ 7.53-7.40, 7.38-7.24, 7.23-7.03, 6.90-6.80, 4.75, 4.54, 4.41, 3.69, 3.67, 3.63-3.53, 3.49-3.40, 2.94-2.81, 2.78, 2.76, 2.74-2.63, 2.61-2.48, 2.24, 1.94-1.83, 1.72-1.66, 1.53, 1.42-1.20, 1.18-1.05.

Example 53

(3R,5R)-7-{2-(4-fluoro-phenyl)-4-isopropyl-5-[methyl-(3-methyl-benzyl)-carbamoyl]-2H-pyrazol-3-yl}-3,5-dihydroxy-heptanoic acid sodium salt The title compound was prepared in a manner analogous to the method of Example 1: MS(APCI$^+$) 526.3 m/z (M+H); H-NMR (DMSO-d$_6$) [Mixture of rotamers at 25° C.] δ 7.48-7.40, 7.31-7.21, 7.19-7.00, 5.70, 4.71, 4.58, 4,47, 3.65-3.55, 3.47-3.41, 3.11, 2.93-2.83, 2.78, 2.77, 2.68-2.63, 2.60-2.48, 2.46-2.44, 1.93-1.86, 1.75-1.64, 1.42-1.23, 1.05-1.10.

Example 54

(3R,5R)-7-{2-(4-fluoro-phenyl)-4-isopropyl-5-[(3-methoxy-benzyl)-methyl-carbamoyl]-2H-pyrazol-3-yl}-3,5-dihydroxy-heptanoic acid sodium salt

Example 56

(3R,5R)-7-[5-(benzyl-isopropyl-carbamoyl)-2-(4-fluoro-phenyl)-4-isopropyl-2H-pyrazol-3-yl]-3,5-dihydroxy-heptanoic acid sodium salt

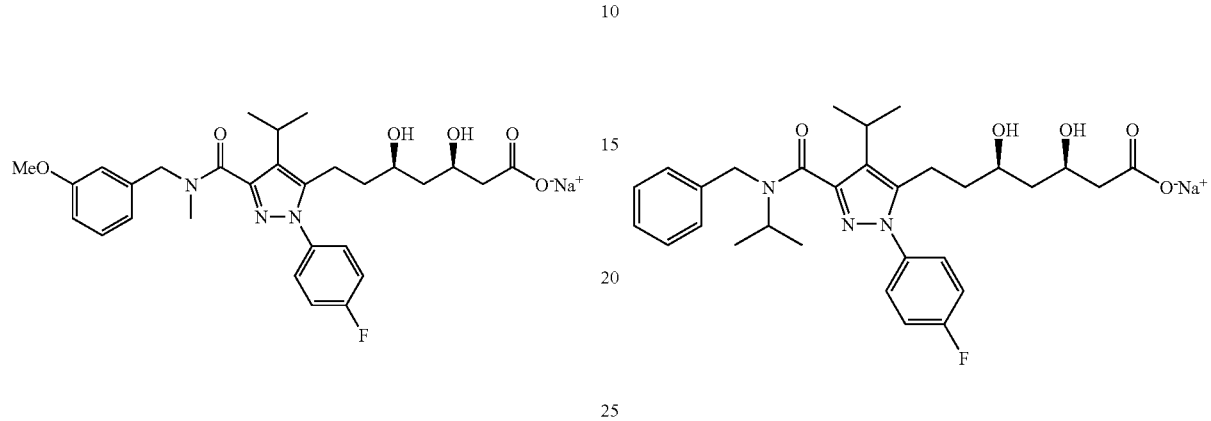

The title compound was prepared in a manner analogous to the method of Example 1: MS(APCI$^+$) 542.3 m/z (M+H); H-NMR (DMSO-d$_6$) [Mixture of rotamers at 25° C.] δ 7.48-7.44, 7.40-7.11, 6.88-6.76, 4.71, 4.59, 4.50, 3.68, 3.59, 3.45, 2.89-2.86, 2.81, 2.80, 2.76-2.63, 2.58-2.52, 1.94-1.89, 1.74-1.68, 1.42-1.23, 1.17-1.12.

The title compound was prepared in a manner analogous to the method of Example 1: MS(APCI$^+$) 540.3 m/z (M+H); H-NMR (DMSO-d$_6$) [Mixture of rotamers at 25° C.] δ 7.49-7.41, 7.38-7.07, 4.71, 4.57, 4.44, 4.38-4.24, 4.09-4.03, 3.64-3.50, 3.47-3.28, 2.95-2.80, 2.77-2.63, 2.61-2.45, 2.24, 1.94-1.90, 1.74-1.65, 1.43-1.02.

Example 55

(3R,5R)-7-[5-(benzyl-ethyl-carbamoyl)-2-(4-fluoro-phenyl)-4-isopropyl-2H-pyrazol-3-yl]-3,5-dihydroxy-heptanoic acid sodium salt

Example 57

(3R,5R)-7-{2-(4-fluoro-phenyl)-4-isopropyl-5-[methyl-(1S-phenyl-ethyl)-carbamoyl]-2H-pyrazol-3-yl}-3,5-dihydroxy-heptanoic acid sodium salt

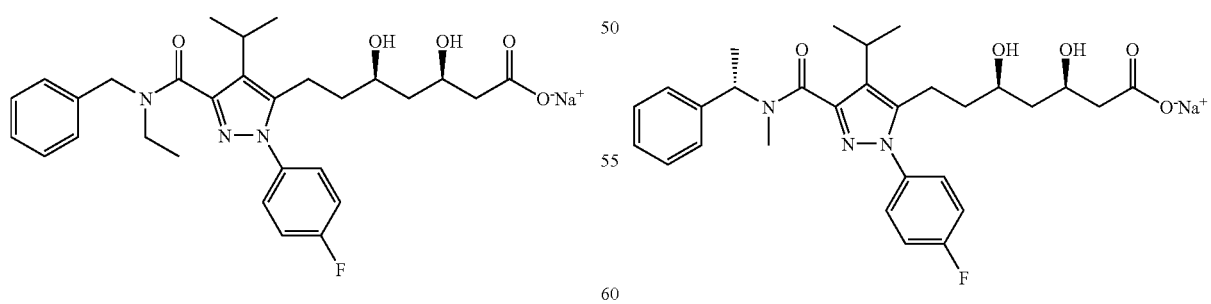

The title compound was prepared in a manner analogous to the method of Example 1: MS(APCI$^+$) 526.3 m/z (M+H); H-NMR (DMSO-d$_6$) [Mixture of rotamers at 25° C.] δ 7.48-7.44, 7.39-7.32, 7.31-7.08, 4.71, 4.62, 4.47, 3.64-3.53, 3.51-3.39, 3.24-3.18, 2.95-2.80, 2.78-2.63, 2.62-2.49, 1.93-1.89, 1.73-1.67, 1.41-1.23, 1.22-1.08, 1.07-1.02.

The title compound was prepared in a manner analogous to the method of Example 1: MS(APCI$^+$) 526.3 m/z (M+H); H-NMR (DMSO-d$_6$) [Mixture of rotamers at 25° C.] δ 7.46-7.42, 7.35-7.12, 5.94-5.91, 5.25-5.21, 3.60-3.52, 3.46-3.41, 2.92-2.83, 2.71-2.65, 2.60, 2.54, 1.92-1.88, 1.72-1.66, 1.49-1.11.

Example 58

(3R,5R)-7-[5-(cyclohexylmethyl-carbamoyl)-2-(4-fluoro-phenyl)-4-isopropyl-2H-pyrazol-3-yl]-3,5-dihydroxy-heptanoic acid sodium salt

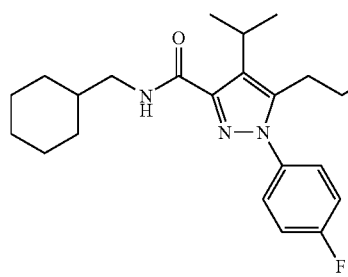

The title compound was prepared in a manner analogous to the method of Example 1: MS(APCI⁺) 504.2 m/z (M+H); H-NMR (DMSO-d₆) δ 7.51-7.48 (m, 2 H), 7.33-7.28 (m, 2 H), 3.60-3.56 (m, 1 H), 3.44-3.40 (m, 1 H), 3.29-3.15 (m, 3 H), 2.98 (d, 2 H), 2.68-2.61 (m, 1 H), 2.52-2.46 (m, 1 H), 1.92-1.87 (m, 1 H), 1.72-1.66 (m, 2 H), 1.62-1.11 (m, 18 H)–.

Example 59

(3R,5R)-7-[2-(4-fluoro-phenyl)-4-isopropyl-5-(1S-p-tolyl-ethylcarbamoyl)-2H-pyrazol-3-yl]-3,5-dihydroxy-heptanoic acid sodium salt

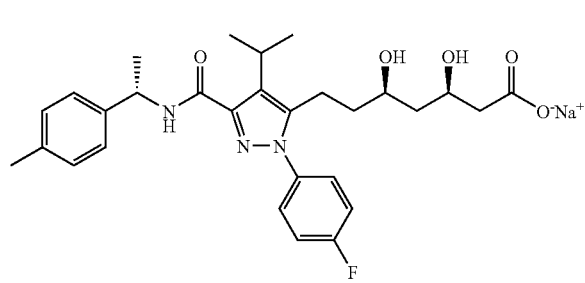

The title compound was prepared in a manner analogous to the method of Example 1: MS(APCI⁺) 526.1 m/z (M+H); H-NMR (DMSO-d₆) δ 7.51-7.48 (m, 2 H), 7.32-7.27 (m, 2 H), 7.22-7.17 (m, 2 H), 7.03-7.01 (m, 2 H), 5.03-5.01 (m, 1 H), 3.60-3.56 (m, 1 H), 3.46-3.41 (m, 1 H), 2.68-2.46 (m, 1 H), 2.56-2.52 (m, 1 H), 2.19 (s, 3 H), 1.92-1.87 (m, 1 H), 1.72-1.67 (m, 1 H), 1.37-1.08 (m, 13 H).

Example 60

(3R,5R)-7-[2-(4-fluoro-phenyl)-4-isopropyl-5-(3-methoxymethyl-benzylcarbamoyl)-2H-pyrazol-3-yl]-3,5-dihydroxy-heptanoic acid sodium salt

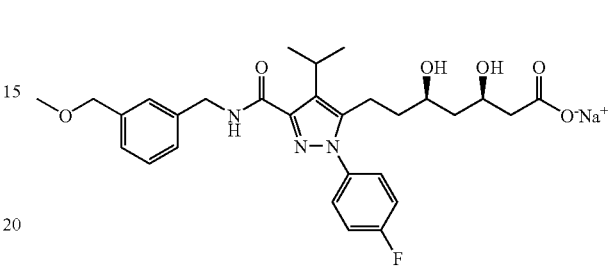

The title compound was prepared in a manner analogous to the method of Example 1: MS(APCI⁺) 542.2 m/z (M+H); H-NMR (DMSO-d₆) δ 8.56 (t, 1 H), 7.55-7.52 (m, 2 H), 7.35-7.11 (m, 6 H), 4.73 (bs, 1 H), 4.37-4.33 (m, 4 H), 3.64-3.62 (m, 1 H), 3.48-3.46 (m, 1 H), 3.23 (s, 3 H), 2.72-2.69 (m, 1 H), 2.59-2.45 (m, 1 H), 1.95 (dd, 1 H), 1.78-1.73 (m, 1 H), 1.40-1.13 (m, 10 H).

Example 61

(3R,5R)-7-{2-(4-fluoro-phenyl)-4-isopropyl-5-[1S-(3-methoxy-phenyl)-ethylcarbamoyl-2H-pyrazol-3-yl}-3,5-dihydroxy-heptanoic acid sodium salt

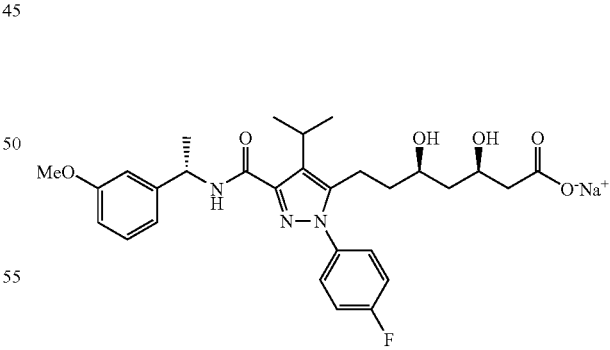

The title compound was prepared in a manner analogous to the method of Example 1: MS(APCI⁺) 542.3 m/z (M+H); H-NMR (DMSO-d₆) δ 8.26 (bs, 1 H), 7.53-7.50 (m, 2 H), 7.33-7.29 (m, 2 H), 7.17-7.10 (m, 1 H), 6.91-6.88 (m, 2 H), 6.73-6.70 (m, 1 H), 5.05-5.01 (m, 1 H), 3.66 (s, 3 H), 3.61-3.57 (m, 1 H), 3.45-3.41 (m, 1 H), 2.71-2.65 (m, 1 H), 2.57-2.50 (m, 1 H), 1.93-1.88 (m, 1.73-1.67 (m, 1 H), 1.37-1.11 (m, 13 H).

Example 62

(3R,5R)-7-{2-(4-fluoro-phenyl)-4-isopropyl-5-[1S-(4-methoxy-phenyl)-ethylcarbamoyl-2H-pyrazol-3-yl}-3,5-dihydroxy-heptanoic acid sodium salt

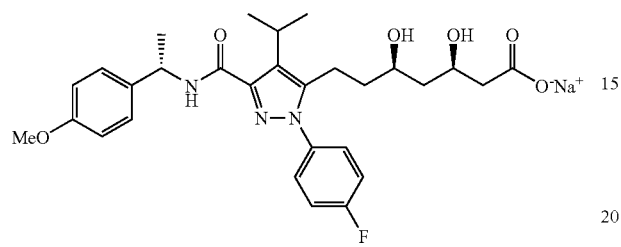

The title compound was prepared in a manner analogous to the method of Example 1: MS(APCI⁺) 542.3 m/z (M+H); H-NMR (DMSO-d$_6$) δ 8.35-8.08 (m, 1 H), 7.65-7.40 (m, 2 H), 7.38-7.15 (m, 4 H), 6.93-6.70 (m, 2 H), 5.17-4.95 (m, 1 H), 4.80-4.60 (m, 1 H), 3.80-3.50 (s, 3 H), 2.80-2.58 (m, 1 H), 2.56-2.50 (m, 1 H), 2.40-2.18 (m, 1 H), 1.98-1.82 (m, 1 H), 1.79-1.63 (m, 1 H), 1.54-0.78 (m, 14 H).

Example 63

(3R,5R)-7-{2-(4-fluoro-phenyl)-4-isopropyl-5-[methyl-(3-trifluoromethyl-benzyl)-carbamoyl]-2H-pyrazol-3-yl}-3,5-dihydroxy-heptanoic acid sodium salt

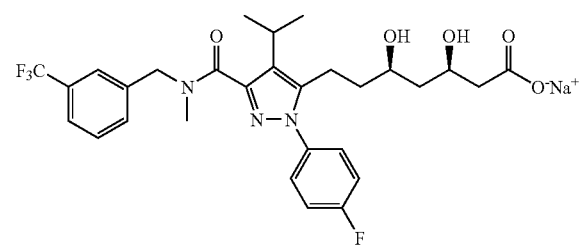

The title compound was prepared in a manner analogous to the method of Example 1: MS(APCI⁺) 580.3 m/z (M+H); H-NMR (DMSO-d$_6$) [Mixture of rotamers at 25° C.] δ 7.66-7.23, 4.71, 4.61, 3.58, 3.44, 3.27, 3.26, 2.61-2.44, 1.91-1.86, 1.71-1.65, 1.29-1.05.

Example 64

(3R,5R)-7-{2-(4-fluoro-phenyl)-4-isopropyl-5-[methyl-(4-trifluoromethyl-benzyl)-carbamoyl]-2H-pyrazol-3-yl}-3,5-dihydroxy-heptanoic acid sodium salt

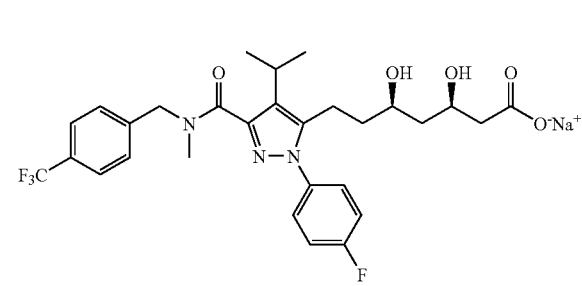

The title compound was prepared in a manner analogous to the method of Example 1: MS(APCI⁺) 580.3 m/z (M+H); H-NMR (DMSO-d$_6$) [Mixtuer of rotamers at 25° C.] δ 7.70-7.64, 7.5-7.44, 7.36-7.12, 4.71, 4.61, 3.59-3.56, 3.45-3.41, 2.86, 2.85, 2.73-2.43, 1.91-1.87, 1.71-1.66, 1.36-1.09.

Example 65

(3R,5R)-7-[2-(4-fluoro-phenyl)-4-isopropyl-5-propylcarbamoyl-2H-pyrazol-3-yl]-3,5-dihydroxy-heptanoic acid sodium salt

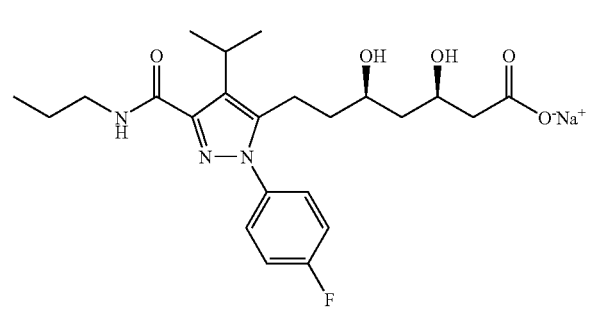

The title compound was prepared in a manner analogous to the method of Example 1: MS(APCI⁺) 450.3 m/z (M+H); H-NMR (DMSO-d$_6$) δ 7.51-7.48 (m, 2 H), 7.33-7.28 (m, 2 H), 3.60-3.57 (m, 1 H), 3.46-3.41 (m, 1 H), 3.09 (t, 2 H), 2.68-2.64 (m, 1 H), 2.57-2.50 (m, 1 H), 1.93-1.88 (m, 1 H), 1.73-1.67 (m, 1 H), 1.43-1.10 (m, 12 H), 0.79 (t, 3 H).

Example 66

(3R,5R)-7-[5-(4-dimethylcarbamoyl-benzylcarbamoyl)-2-(4-fluoro-phenyl)-4-isopropyl-2H-pyrazol-3-yl]-3,5-dihydroxy-heptanoic acid sodium salt

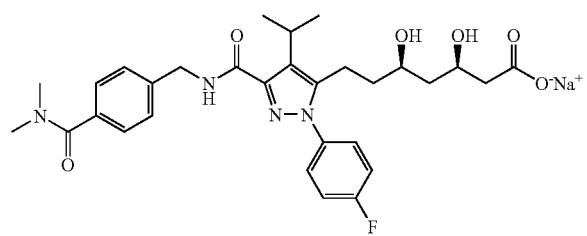

The title compound was prepared in a manner analogous to the method of Example 1: MS(APCI$^+$) 567.2 m/z (M−H); H-NMR (DMSO-d$_6$) δ 8.64-8.59 (m, 1 H), 7.67-7.35 (m, 4 H), 7.30-7.05 (m, 4 H), 4.72 (s, 1 H), 4.36 (d, 2 H), 3.65-3.35 (m, 2 H), 2.90 (s, 3 H), 2.82 (s, 3 H), 1.91-1.83 (m, 1 H), 1.75-1.62 (m, 1 H), 1.40-1.05 (m, 13 H).

Example 67

(3R,5R)-7-{2-(4-fluoro-phenyl)-4-isopropyl-5-[(Pyridin-2-ylmethyl)-carbamoyl]-2H-pyrazol-3-yl}-3,5-dihydroxy-heptanoic acid sodium salt

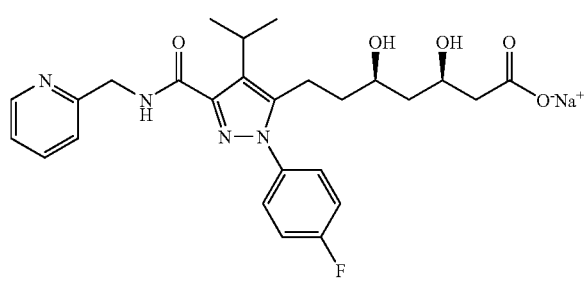

The title compound was prepared in a manner analogous to the method of Example 1: MS(APCI$^+$) 499.3 m/z (M+H); H-NMR (DMSO-d$_6$) δ 8.62-8.51 (m, 1 H), 8.45-8.37 (m, 1 H), 7.70 (t, 1 H), 7.62-7.40 (m, 2 H), 7.39-7.12 (m, 4 H), 4.73 (s, 1 H), 4.45 (d, 2 H), 3.63-3.55 (m, 1 H), 3.48-3.39 (m, 1 H), 2.80-2.62 (m, 1 H), 2.60-2.43 (m, 1 H), 1.92-1.88 (m, 1 H), 1.72-1.63 (m, 1 H), 1.50-1.02 (m, 12 H).

Example 68

(3R,5R)-7-[2-(4-fluoro-phenyl)-5-(2-hydroxy-1R-phenyl-ethylcarbamoyl)-4-isopropyl-2H-pyrazol-3-yl]-3,5-dihydroxy-heptanoic acid sodium salt

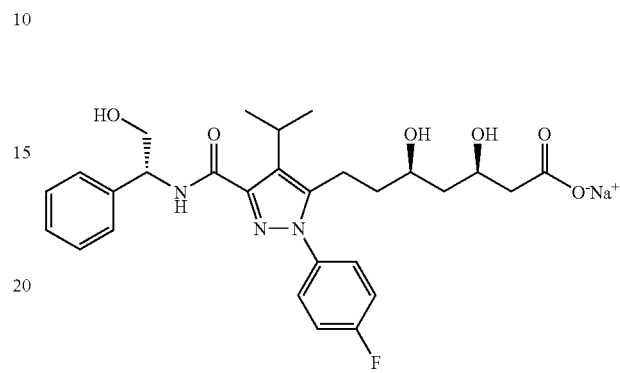

The title compound was prepared in a manner analogous to the method of Example 1: MS(APCI$^+$) 528.3 m/z (M+H); H-NMR (DMSO-d$_6$) δ 8.26 (d, 1 H), 7.54 (t, 1 H), 7.50-7.16 (m, 9 H), 5.12-5.00 (m, 1 H), 4.97-4.92 (m, 1 H), 4.71 (m, 1 H), 3.70-3.50 (m, 2 H), 3.48-3.38 (m, 1 H), 3.22-3.05 (m, 1 H), 2.78-2.60 (m, 1 H), 2.58-2.48 (m, 1 H), 1.91-1.86 (m, 1 H), 1.73-1.67 (m, 1 H), 1.40-1.00 (m, 13 H).

Example 69

(3R,5R)-7-[2-(4-fluoro-phenyl)-4-isopropyl-5-(morpholine-4-carbonyl)-2H-pyrazol-3-yl]-3,5-dihydroxy-heptanoic acid sodium salt

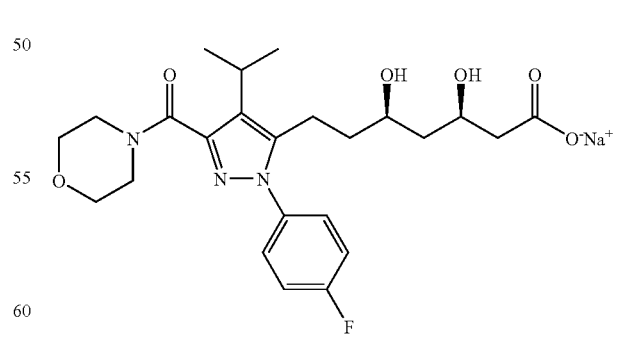

The title compound was prepared in a manner analogous to the method of Example 1: MS(APCI$^+$) 478.3 m/z (M+H); H-NMR (DMSO-d$_6$) [Mixture of rotamers at 25° C.] δ 7.59-7.38, 7.36-7.11, 4.78-4.64, 3.64-3.44, 3.42-3.30, 2.98-2.80, 2.78-2.63, 2.60-2.38, 1.93-1.87, 1.72-1.66, 1.40-1.10.

Example 70

(3R,5R)-7-[2-(4-fluoro-phenyl)-4-isopropyl-5-isopropylcarbamoyl-2H-pyrazol-3-yl]-3,5-dihydroxy-heptanoic acid sodium salt

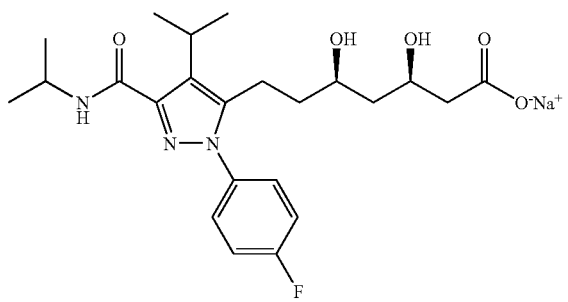

The title compound was prepared in a manner analogous to the method of Example 1: MS(APCI$^+$) 450.3 m/z (M+H); H-NMR (DMSO-d$_6$) δ 7.65 (d, 1 H), 7.52-7.45 (m, 2 H), 7.35-7.23 (m, 1 H), 4.70 ), s 1 H), 4.03-4.93 (m, 1 H), 3.64-3.56 (m, 1 H), 3.42-3.38 (m, 1 H), 3.22-3.15 (m, 1 H), 2.73-2.60 (m, 1 H), 2.57-2.43 (m, 1 H), 1.94-1.89 (m, 1 H), 1.74-1.65 (m, 1 H), 1.40-1.17 (m, 9 H), 1.15-1.03 (m, 9 H).

Example 71

(3R,5R)-7-[5-(cyclohexylmethyl-methyl-carbamoyl)-2-(4-fluoro-phenyl)-4-isopropyl-2H-pyrazol-3-yl]-3,5-dihydroxy-heptanoic acid sodium salt

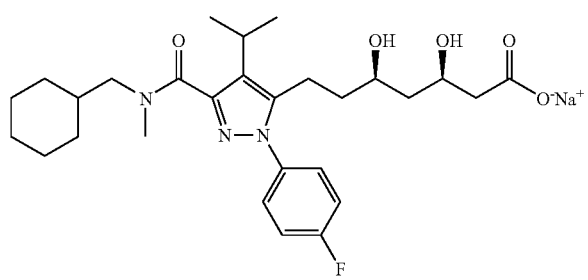

The title compound was prepared in a manner analogous to the method of Example 1: MS(APCI$^+$) 518.3 m/z (M+H); H-NMR (DMSO-d$_6$) [Mixture of rotamers at 25° C.] δ 7.46-7.39, 7.32-7.26, 3.61-3.57, 3.44-3.41, 3.16-3.12, 2.85, 2.83, 2.68-2.60, 2.58-2.51, 1.92-1.87, 1.72-1.45, 1.39-1.23, 1.15-1.03, 0.94-0.91, 0.76-0.71.

Example 72

(3R,5R)-7-[5-(cyclopentylmethyl-carbamoyl)-2-(4-fluoro-phenyl)-4-isopropyl-2H-pyrazol-3-yl]-3,5-dihydroxy-heptanoic acid sodium salt

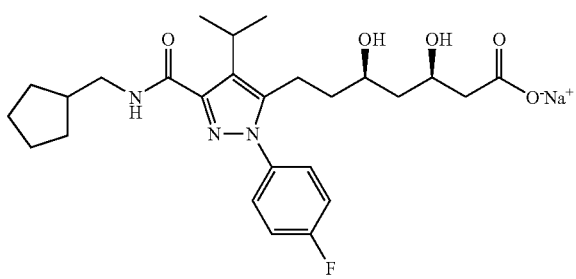

The title compound was prepared in a manner analogous to the method of Example 1: MS(APCI$^+$) 490.3 m/z (M+H); H-NMR (DMSO-d$_6$) δ 7.51-7.48 (m, 2 H), 7.32-7.28 (m, 2 H), 3.58-3.56 (m, 1 H), 3.48-3.43 (m, 1 H), 3.10 (d, 2 H), 2.68-2.61 (m, 1 H), 2.56-2.50 (m, 1 H), 2.08-2.03 (m, 1 H), 1.90-1.85 (m, 1 H), 1.69-1.64 (m, 1 H), 1.66-1.09 (m, 18 H).

Example 73

(3R,5R)-7-[2-(4-fluoro-phenyl)-5-isobutylcarbamoyl-4-isopropyl-2H-pyrazol-3-yl]-3,5-dihydroxy-heptanoic acid sodium salt

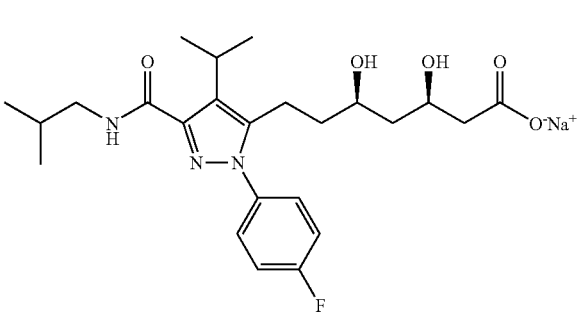

The title compound was prepared in a manner analogous to the method of Example 1: MS(APCI$^+$) 464.3 m/z (M+H); H-NMR (DMSO-d$_6$) δ 7.95 (bs, 1 H), 7.51-7.48 (m, 2 H), 7.32-7.28 (m, 2 H), 3.60-3.56 (m, 1 H), 3.45-3.43 (m, 1 H), 3.18-3.13 (m, 1 H), 2.96 (d, 2 H), 2.71-2.65 (m, 1 H), 2.56-2.52 (m, 1 H), 1.92-1.87 (m, 1 H), 1.88-1.74 (m, 2 H), 1.39-1.05 (m, 10 H), 0.79 (d, 6 H).

Example 74

(3RR,5R)-7-[2-(4-fluoro-phenyl)-4-isopropyl-5-(3-methyl-butylcarbamoyl)-2H-pyrazol-3-yl]-3,5-dihydroxy-heptanoic acid sodium salt

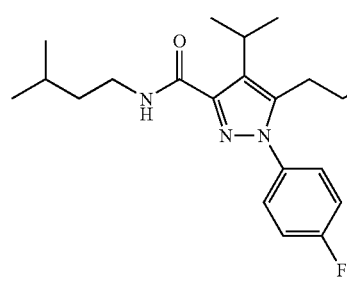

The title compound was prepared in a manner analogous to the method of Example 1: MS(APCI$^+$) 487.3 m/z (M+H); H-NMR (DMSO-d$_6$) δ 7.51-7.47 (m, 2 H), 7.32-7.28 (m, 2 H), 3.59-3.56 (m, 1 H), 3.44-3.24 (m, 1 H), 3.18-3.12 (m, 2 H), 2.67-2.61 (m, 1 H), 2.46-2.43 (m, 1 H), 1.90-1.86 (m, 1 H), 1.68-1.46 (m, 1 H), 1.55-1.51 (m, 1 H), 1.39-1.05 (m, 12 H), 0.82 (d, 6 H).

Example 75

(3R,5R)-7-[5-cyclopentylcarbamoyl-2-(4-fluoro-phenyl)-4-isopropyl-2H-pyrazol-3-yl]-3,5-dihydroxy-heptanoic acid sodium salt

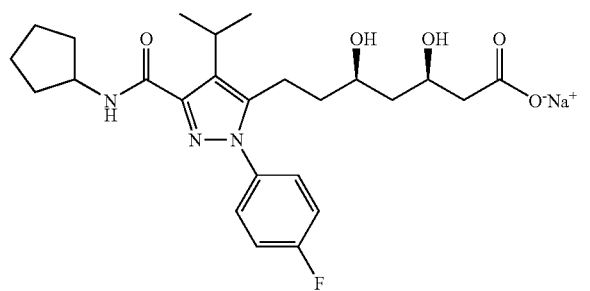

The title compound was prepared in a manner analogous to the method of Example 1: MS(APCI$^+$) 476.3 m/z (M+H); H-NMR (DMSO-d$_6$) δ 7.75 (d, 1 H), 7.51-7.47 (m, 2 H), 7.33-7.28 (m, 2 H), 4.70 (d, 1 H), 4.14-4.09 (m, 1 H), 3.59-3.51 (m, 1 H), 3.46-3.41 (m, 1 H), 3.18-3.13 (m, 1 H), 2.71-2.66 (m, 1 H), 2.56-2.50 (m, 1 H), 1.92-1.88 (m, 1 H), 1.81-1.70 (m, 3 H), 1.61-1.52 (m, 2 H), 1.43-1.39 (m, 2 H), 1.38-1.15 (m, 10 H).

Example 76

(3R,5R)-7-[2-(4-fluoro-phenyl)-4-isopropyl-5-(2-phenyl-pyrrolidine-1-carbonyl)-2H-pyrazol-3-yl]-3,5-dihydroxy-heptanoic acid sodium salt

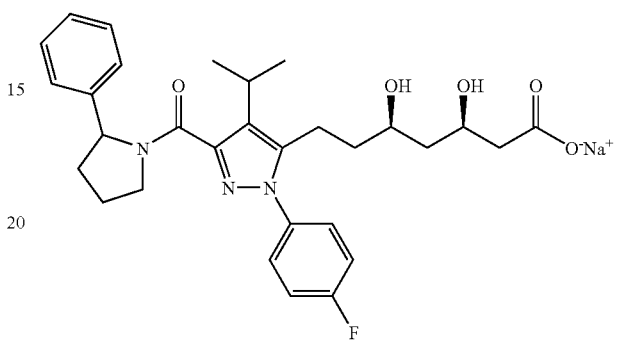

The title compound was prepared in a manner analogous to the method of Example 1: MS(APCI$^+$) 538.3 m/z (M+H); H-NMR (DMSO-d$_6$) [Mixture of diastereomers] δ 7.51-7.47, 7.33-7.06, 6.93-6.92, 5.37-5.32, 5.14-5.11, 3.79-3.28, 2.96-2.89, 2.78-2.19, 1.92-1.56, 1.24-0.87.

Example 77

(3R,5R)-7-[5-(cyclobutylmethyl-carbamoyl)-2-(4-fluoro-phenyl)-4-isopropyl-2H-pyrazol-3-yl]-3,5-dihydroxy-heptanoic acid sodium salt

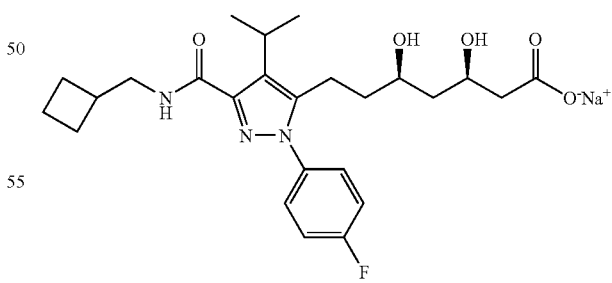

The title compound was prepared in a manner analogous to the method of Example 1: MS(APCI$^+$) 476.3 m/z (M+H); H-NMR (DMSO-d$_6$) δ 7.51-7.47 (m, 2 H), 7.32-7.27 (m, 2 H), 3.61-3.57 (m, 2 H), 3.61-3.57 (m, 1 H), 3.44-3.41 (m, 1 H), 3.20-3.16 (m, 1 H), 2.67-2.63 (m, 1 H), 2.54-2.51 (m, 1 H), 1.92-1.84 (m, 3 H), 1.78-1.57 (m, 5 H), 1.41-1.06 (m, 1.06).

Example 78

(3R,5R)-7-[5-[(2,3-difluoro-benzyl)-methyl-carbamoyl]-2-(4-fluoro-phenyl)-4-isopropyl-2H-pyrazol-3-yl]-3,5-dihydroxy-heptanoic acid sodium salt

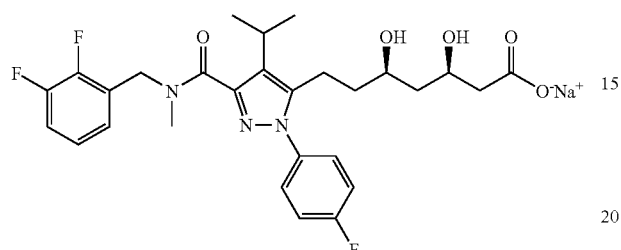

The title compound was prepared in a manner analogous to the method of Example 1: MS(APCI$^+$) 548.3 m/z (M+H); H-NMR (DMSO-d$_6$) [Mixture of rotamers at 25° C.] δ 7.48-7.01, 4.71-4.69, 3.59-3.57, 3.44, 2.88, 2.84-2.81, 2.72-2.68, 2.56-2.61, 1.92-1.88, 1.72-1.69, 1.40-1.24, 1.14-1.08.

Example 79

(3R,5R)-7-[5-(cyclopropylmethyl-carbamoyl)-2-(4-fluoro-phenyl)-4-isopropyl-2H-pyrazol-3-yl]-3,5-dihydroxy-heptanoic acid sodium salt

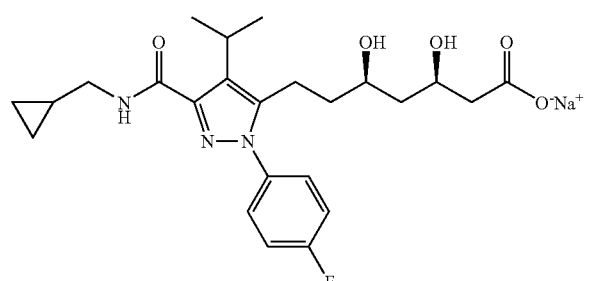

The title compound was prepared in a manner analogous to the method of Example 1: MS(APCI$^+$) 462.3 m/z (M+H); H-NMR (DMSO-d$_6$) δ 7.51-7.48 (m, 2 H), 7.32-7.28 (m, 2 H), 3.61-3.59 (m, 1 H), 3.43-3.41 (m, 1 H), 3.18-3.17 (m, 1 H), 3.01 (d, 2 H), 2.68-2.64 (m, 1 H), 2.56-2.49 (m, 1 H), 1.93-1.88 (m, 1 H), 1.73-1.67 (m, 1 H), 1.39-1.01 (m, 10 H), 0.33-0.29 (m, 2 H), 0.16-0.12 (m, 2 H).

Example 80

(3R,5R)-7-[5-[(2,4-difluoro-benzyl)-methyl-carbamoyl]-2-(4-fluoro-phenyl)-4-isopropyl-2H-pyrazol-3-yl]-3,5-dihydroxy-heptanoic acid sodium salt

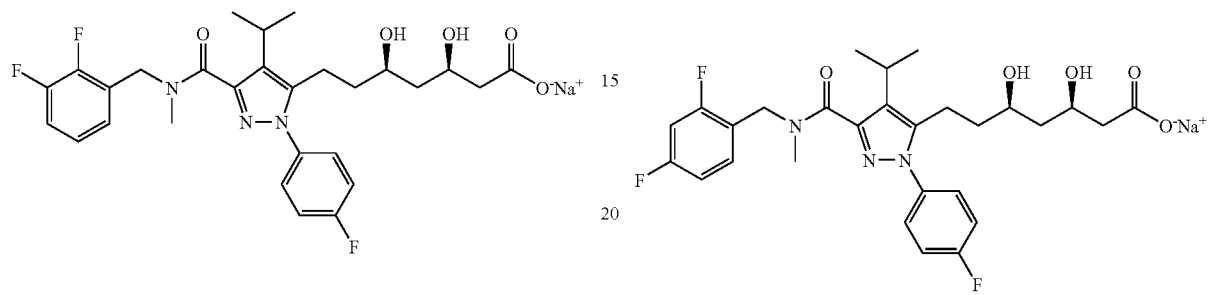

The title compound was prepared in a manner analogous to the method of Example 1: MS(APCI$^+$) 548.3 m/z (M+H); H-NMR (DMSO-d$_6$) [Mixture of rotamers at 25° C.] δ 7.53-7.00, 4.71, 4.64, 4.60, 3.61-3.57, 3.44-3.42, 2.84, 2.81, 2.72-2.66, 2.56-2.53, 1.92-1.87, 1.72-1.66, 1.36-1.09.

Example 81

(3R,5R)-7-[2-(4-fluoro-phenyl)-4-isopropyl-5-[methyl-(4-trifluoromethoxy-benzyl)-carbamoyl]-2H-pyrazol-3-yl]-3,5-dihydroxy-heptanoic acid sodium salt

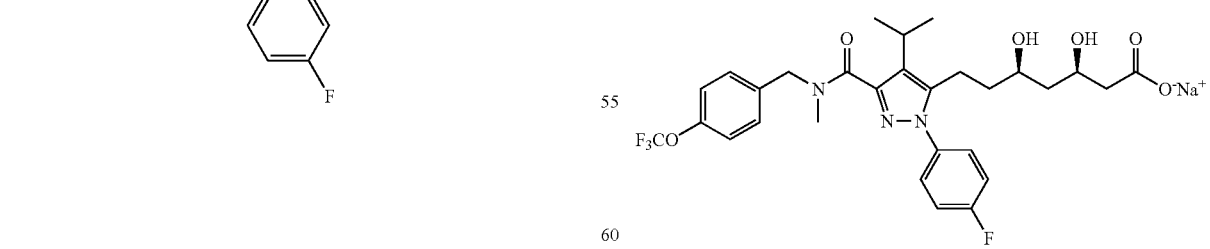

The title compound was prepared in a manner analogous to the method of Example 1:H-NMR [Mixture of rotamers at 25° C.] (DMSO-d$_6$) δ 7.51-7.25, 4.72, 4.67, 4.57, 3.66-3.61, 3.51-3.42, 2.90, 2.87, 2.76-2.71, 2.52-2.44, 1.96-1.91, 1.76-1.72, 1.39-1.08.

Example 82

(3R,5R)-7-[5-butylcarbamoyl-2-(4-fluoro-phenyl)-4-isopropyl-2H-pyrazol-3-yl]-3,5-dihydroxy-heptanoic acid sodium salt

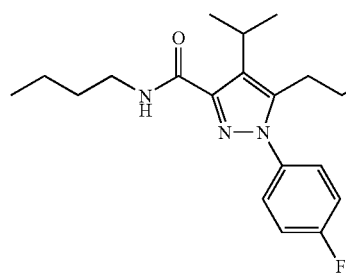

The title compound was prepared in a manner analogous to the method of Example 1: MS(APCI$^+$) 464.2 m/z (M+H); H-NMR (DMSO-d$_6$) δ 7.97 (t, 3 H), 7.56-7.51 (m, 3 H), 7.35-7.31 (m, 2 H), 4.74-4.73 (m, 1 H), 3.69-3.59 (m, 1 H), 3.56-3.40 (m, 1 H), 3.21-3.12 (m, 3 H), 2.78-2.63 (m, 1 H), 2.60-2.43 (m, 1 H), 1.95-1.90 (m, 1 H), 1.75-1.69 (m, 1 H), 1.47-1.33 (m, 2 H), 1.31-1.21 (m, 12 H), 1.20-1.10 (m, 1 H), 0.85 (t, 3 H).

Example 83

(3R,5R)-7-[2-(4-fluoro-phenyl)-4-isopropyl-5-(piperidine-1-carbonyl)-2H-pyrazol-3-yl]-3,5-dihydroxy-heptanoic acid sodium salt

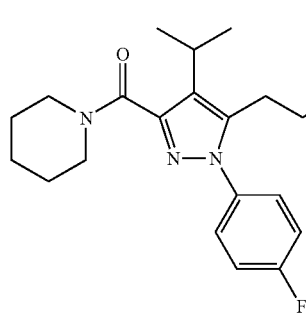

The title compound was prepared in a manner analogous to the method of Example 1: MS(APCI$^+$) 476.2 m/z (M+H); H-NMR (DMSO-d$_6$) [Mixture of rotamers at 25° C.] δ 7.66-7.60, 7.50-7.41, 7.34-7.27, 4.75-4.68, 3.63-3.60, 3.59-3.55, 3.52-3.43, 2.95-2.82, 2.80-2.63, 2.61-2.45, 1.95-1.90, 1.74-1.68, 1.60-1.51, 1.46-1.43, 1.42-1.38, 1.36-1.25, 1.24-1.13.

Example 84

(3R,5R)-7-{2-(4-fluoro-phenyl)-4-isopropyl-5-[methyl-(3-trifluoromethoxy-benzyl)-carbamoyl]-2H-pyrazol-3-yl}-3,5-dihydroxy-heptanoic acid sodium salt

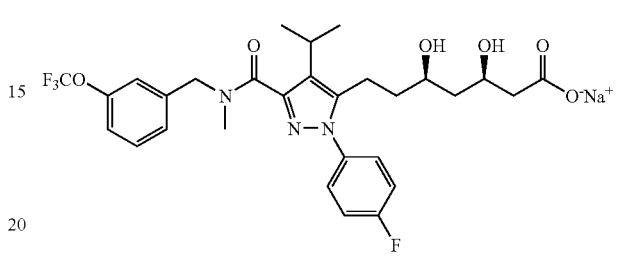

The title compound was prepared in a manner analogous to the method of Example 1: MS(APCI$^+$) H-NMR (DMSO-d$_6$) [Mixture of rotamers at 25° C.] δ 7.66-7.25, 4.73, 4.69, 4.59, 3.66-3.59, 3.52-3.43, 2.87, 2.86, 2.76-2.71, 2.58-2.52, 1.94-1.89, 1.74-1.68, 1.34-1.08.

Example 85

(3R,5R)-7-[5-cyclohexylcarbamoyl-2-(4-fluoro-phenyl)-4-isopropyl-2H-pyrazol-3-yl]-3,5-dihydroxy-heptanoic acid sodium salt The title compound was prepared in a manner analogous to the method of Example 1: MS(APCI$^+$) 490.1 m/z (M+H); H-NMR (DMSO-d$_8$) δ 7.82-7.76 (m, 1 H), 7.59-7.43 (m, 2 H), 7.39-7.25 (m, 2 H), 4.78-4.64 (m, 1 H), 3.80-3.58 (m, 2 H), 3.56-3.40 (m, 1 H), 3.23-3.08 (m, 1 H), 2.78-2.60 (m, 1 H), 2.59-2.43 (m, 1 H), 1.96-1.86 (m, 1 H), 1.80-1.62 (m, 4 H), 1.60-1.43 (m, 1 H), 1.41-1.04 (m, 18 H).

Example 86

(3R,5R)-7-[5-(4-cyano-benzylcarbamoyl)-2-(4-fluoro-phenyl)-4-isopropyl-2H-pyrazol-3-yl]-3,5-dihydroxy-heptanoic acid sodium salt

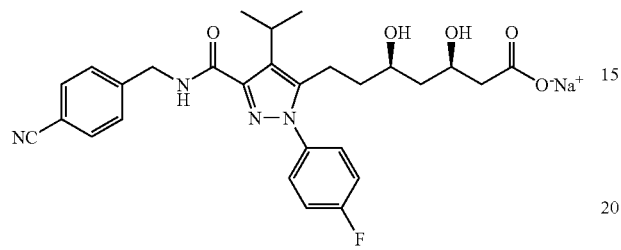

The title compound was prepared in a manner analogous to the method of Example 1: MS(APCI+) 523.1 m/z (M+H); H-NMR (DMSO-$d_6$) δ 8.78-8.75 (m, 1 H), 7.78-7.74 (m, 2 H), 7.61-7.51 (m, 2 H), 7.49-7.40 (m, 2 H), 7.39-7.29 (m, 2 H), 4.76-4.71 (m, 1 H), 4.43-4.38 (m, 2 H), 3.68-3.58 (m, 1 H), 3.57-3.42 (m, 1 H), 3.23-3.16 (m, 2 H), 2.80-2.62 (m, 1 H), 2.61-2.50 (m, 1 H), 1.95-1.91 (m, H), 1.75-1.68 (m, 1 H), 1.43-1.08 (m, 12 H).

Example 87

(3R,5R)-7-[5-(3-cyano-benzylcarbamoyl)-2-(4-fluoro-phenyl)-4-isopropyl-2H-pyrazol-3-yl]-3,5-dihydroxy-heptanoic acid sodium salt

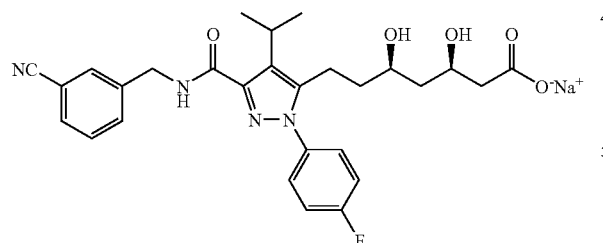

The title compound was prepared in a manner analogous to the method of Example 1: MS(APCI+) 523.1 m/z (M+H); H-NMR (DMSO-$d_6$) δ 8.78-8.75 (m, 1 H), 7.77-7.60 (m, 2 H), 7.59-7.40 (m, 4 H), 7.38-7.23 (m, 2 H), 4.76-4.72 (m, 1 H), 4.43-4.38 (m, 2 H), 3.68-3.58 (m, 1 H), 3.57-3.42 (m, 1 H), 3.23-3.16 (m, 2 H), 2.80-2.62 (m, 1 H), 2.61-2.50 (m, 1 H), 1.95-1.91 (m, 1 H), 1.75-1.68 (m, 1 H), 1.43-1.08 (m, 12 H).

Example 88

(3R,5R)-7-[5-(cyclopentylmethyl-methyl-carbamoyl)-2-(4-fluoro-phenyl)-4-isopropyl-2H-pyrazol-3-yl]-3,5-dihydroxy-heptanoic acid sodium salt

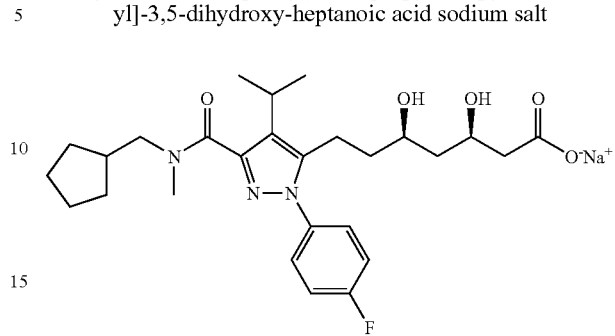

The title compound was prepared in a manner analogous to the method of Example 1: MS(APCI+) 504 m/z (M+H); H-NMR (DMSO-$d_6$) [Mixture of rotamers at 25° C.] δ 7.49-7.31, 3.65-3.61, 3.49-3.46, 3.36, 3.23, 2.89, 2.87, 2.74-2.72, 2.68-2.46, 2.28-2.21, 1.95-1.91, 1.76-1.16.

Example 89

(3R,5R)-7-{2-(4-fluoro-phenyl)-4-isopropyl-5-[methyl-(2-methyl-benzyl)-carbamoyl]-2H-pyrazol-3-yl}-3,5-dihydroxy-heptanoic acid sodium salt

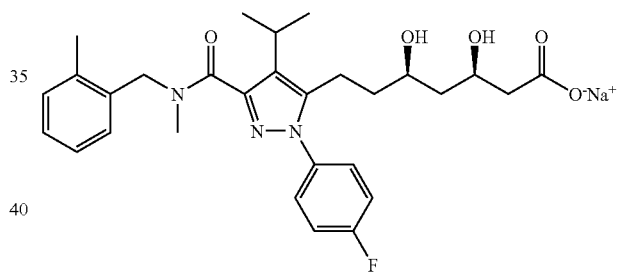

Step A. Preparation of Methyl-(2-methyl-benzyl)-amine

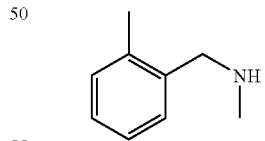

To a solution of 2-methylbenzaldehyde (10.0 g, 83.23 mmol) in MeOH at 25° C. was added methylamine (40 % in $H_2O$, 25.85 g, 332.9 mmol). The reaction mixture was stirred at 25° C. for 30 min after which time it was cooled to 0° C. and $NaBH_4$ (6.30 g, 166.5 mmol) was added portion-wise. The reaction mixture was then warmed to 25° C. and stirred for an additional 1 hr. The solvent was removed under reduced pressure and water and $CH_2Cl_2$ were added. The organic layer was separated and washed with saturated $NaHCO_3$ and brine. After drying over $Na_2SO_4$, organic phase was concentrated to afford desired methyl-(2-methyl-benzyl)-amine (10.49 g, 93.2%) as an oil of sufficient purity for use in the next reaction: MS(APCI⁺) 136.3 m/z (M+H); H-NMR (CDCl₃) δ 7.35-7.08 (m, 3 H), 3.73 (s, 2 H), 2.49 (s, 3 H), 2.34 (s, 3 H).

Step B. Preparation of 1-(4-Fluoro-phenyl)-5-formyl-4-isopropyl-1H-pyrazole-3-carboxylic acid methyl-(2-methyl-benzyl)-amide

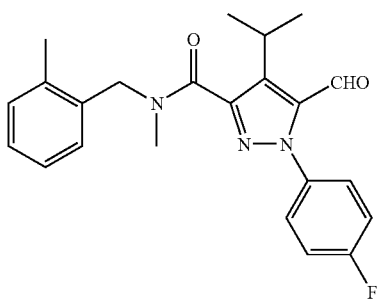

To a solution of 1-(4-fluoro-phenyl)-5-formyl-4-isopropyl-1H-pyrazole-3-carboxylic acid (1.50 g, 5.43 mmol) in CH₂Cl₂ (100 mL) at 25° C. was added EDCI (1.56 g, 8.14 mmol) followed by HOBt.H₂O (1.25 g, 8.14 mmol) and the reaction was stirred for 10 min at 25° C. Subsequently, methyl-(2-methyl-benzyl)-amine (1.10 g, 8.14 mmol) was added and the reaction was stirred for an additional 6 hrs at 25° C. The organic layer was then washed with HCl, saturated NaHCO₃ and brine. After drying over Na₂SO₄ and concentration, the product was purified by column chromatography (10-25 % EtOAc/Hex) to afford desired 1-(4-fluoro-phenyl)-5-formyl-4-isopropyl-1H-pyrazole-3-carboxylic acid methyl-(2-methyl-benzyl)-amide as an oil (1.53 g, 71.6%). MS(APCI⁺) 394.2 m/z (M+H).

Step C. Preparation of 5-(tert-Butyl-dimethyl-silanyloxy)-7-{2-(4-fluoro-phenyl)-4-isopropyl-5-[methyl-(2-ethyl-benzyl)-carbamoyl]-2H-pyrazol-3-yl}-3-oxo-hept-6-enoic acid methyl ester

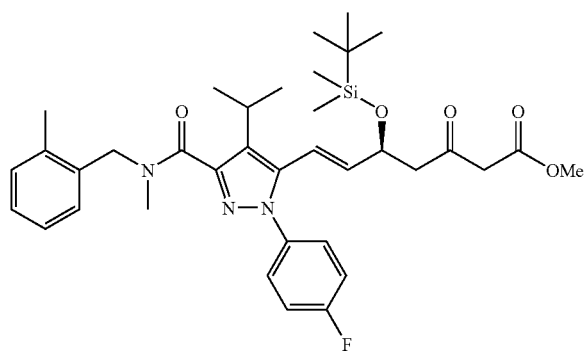

To a solution of 1-(4-fluoro-phenyl)-5-formyl-4-isopropyl-1H-pyrazole-3-carboxylic acid methyl-(2-methyl-benzyl)-amide (1.53 g, 3.89 mmol) in toluene (80 mL) was added 3-(tert-butyl-dimethyl-silanyloxy)-5-oxo-6-(triphenyl-l5-phosphanylidene)-hexanoic acid methyl ester [prepared according to the published method: Konoike, T.; Araki, Y. J. Org. Chem. 1994, 59, 7849-7854] (2.70 g, 5.06 mmol) and the reaction was heated to 95° C. for 16 hrs. After cooling to 25° C., the solvent was removed under reduced pressure and product was run through pad of silica gel (20-30% EtOAc/Hex) to afford 5-(tert-butyl-dimethyl-silanyloxy)-7-{2-(4-fluoro-phenyl)-4-isopropyl-5-[methyl-(2-methyl-benzyl)-carbamoyl]-2H-pyrazol-3-yl}-3-oxo-hept-6-enoic acid methyl ester (2.48 g, 98.1%): MS(APCI⁺) 650.4 m/z (M+H).

Step D. Preparation of 7-(2-(4-Fluoro-phenyl)-4-isopropyl-5-[methyl-(2-methyl-benzyl)-carbamoyl]-2H-pyrazol-3-yl}-5-hydroxy-3-oxo-hept-6-enoic acid methyl ester

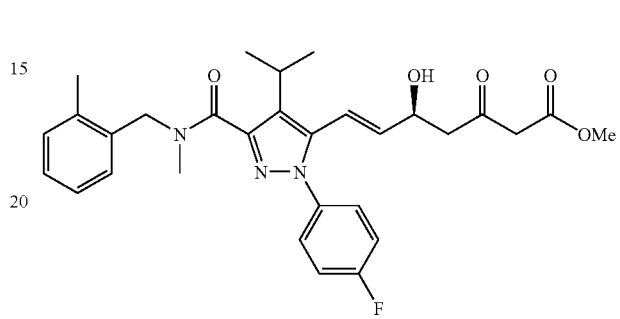

To a solution of 5-(tert-butyl-dimethyl-silanyloxy)-7-{2-(4-fluoro-phenyl)-4-isopropyl-5-[methyl-(2-methyl-benzyl)-carbamoyl]-2H-pyrazol-3-yl}-3-oxo-hept-6-enoic acid methyl ester (2.48 g, 3.82 mmol) in MeCN (40 mL) at 25° C. was added HF (2.5 mL of 48% in water). Reaction was stirred at 25° C. for 16 hrs. Subsequently, EtOAc (100 mL) and water (100 mL) were added and the organic layer was separated, dried and concentrated. Product was purified by column chromatography (30%-50% EtOAc-Hex) to afford 7-{2-(4-fluoro-phenyl)-4-isopropyl-5-[methyl-(2-methyl-benzyl)-carbamoyl]-2H-pyrazol-3-yl}-5-hydroxy-3-oxo-hept-6-enoic acid methyl ester (2.03 g, 98.0%): MS(APCI⁺) 536.4 m/z (M+H).

Step E. 7-{2-(4-Fluoro-Phenyl)-4-isopropyl-5-[methyl-(2-methyl-benzyl)-carbamoyl]-2H-pyrazol-3-yl}-3,5-dihydroxy-hept-6-enoic acid methyl ester

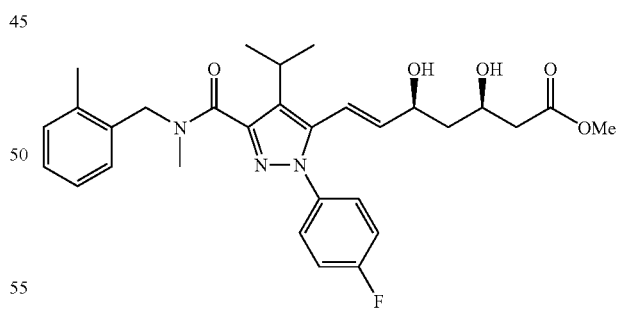

To a solution of 7-{2-(4-Fluoro-phenyl)-4-isopropyl-5-[methyl-(2-methyl-benzyl)-carbamoyl]-2H-pyrazol-3-yl}-3,5-pyrazol-3-yl}-5-hydroxy-3-oxo-hept-6-enoic acid methyl ester (2.04 g, 3.81 mmol) in THF (100 mL) and MeOH (30 mL) at −78° C. was added diethylmethoxyborane (4.95 mL of 1.0 M solution, 4.95 mmol). Reaction was stirred at −78° C. for 1 hrs after which time NaBH₄ (166 mg, 4.38 mmol) was added. Reaction mixture was stirred at −78° C. for 2 hr and then warmed to 0° C. after which time glacial acetic acid (0.5 mL) was added. Reaction was diluted with EtOAc and water and organic layer was separated and washed with sat. NaHCO₃ and brine prior to concentration. The resulting crude oil was then dissolved in MeOH (50 mL) and evaporated again. Subsequently a second amount of MeOH (50 mL) was added and the solution was stirred at 25° C. for 12 hrs after which time it was concentrated and purified by column chromatography (40-60% EtOAc/Hex) to afford 7-{2-(4-fluoro-phenyl)-4-isopropyl-5-[methyl-(2-methyl-benzyl)-carbamoyl]-2H-pyrazol-3-yl}-3,5-dihydroxy-hept-6-enoic acid methyl ester (1.66 g, 81.1%):

MS(APCI⁺) 538.4 m/z (M+H).

Step F. 7-{2-(4-Fluoro-phenyl)-4-isopropyl-5-[methyl-(2-methyl-benzyl)-carbamoyl-2H-pyrazol-3-yl}-3,5-dihydroxy-heptanoic acid methyl ester

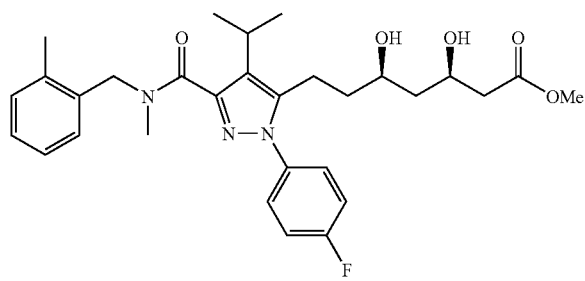

To a solution of 7-{2-(4-fluoro-phenyl)-4-isopropyl-5-[methyl-(2-methyl-benzyl)-carbamoyl]-2H-pyrazol-3-yl}-3,5-dihydroxy-hept-6-enoic acid methyl ester (1.190 g, 2.21 mmol) in MeOH (50 ml) was added Pd—C (0.1 g). The reaction vessel was evacuated, flushed with nitrogen and then filled with hydrogen (via balloon). Reaction was stirred at 25° C. for 4 hrs. Reaction was then flushed with nitrogen and filtered through a pad of celite. The filtrate was concentrated and purified by column chromatography (30-40% EtOAc/Hex) to afford 7-{2-(4-fluoro-phenyl)-4-isopropyl-5-[methyl-(2-methyl-benzyl)-carbamoyl]-2H-pyrazol-3-yl}-3,5-dihydroxy-heptanoic acid methyl ester (0.792 g, 66%): MS(APCI⁺) 540.2 m/z (M+H).

Step G. (3R,5R)-7-{2-(4-fluoro-phenyl)-4-isopropyl-5-[methyl-(2-methyl-benzyl)-carbamoyl-2H-pyrazol-3-yl]-3,5-dihydroxy-heptanoic acid sodium salt

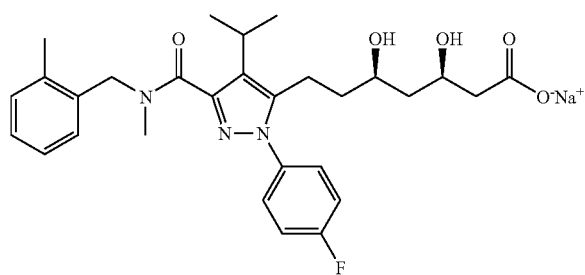

To a solution of 7-{2-(4-fluoro-phenyl)-4-isopropyl-5-[methyl-(2-methyl-benzyl)-carbamoyl]-2H-pyrazol-3-yl}-3,5-dihydroxy-heptanoic acid methyl ester (0.7920 g, 1.47 mmol) in MeOH (5 ml), NaOH solution (1.028N, 1.50 ml, 1.54 mmol) was added. The reaction mixture was stirred at 25° C. for 12 hrs. After solvent was evaporated, the crude product was dried azeotopically with toluene (×3). It was dissolved in MeOH/CH₂Cl₂ mixture (1:9, 10 ml) and diluted with CH₂Cl₂ (15 ml). It was filtered through cotton and the filtrate was concentrated, triturated with Et₂O for 12 hrs. The product was isolated by filtration and dried under vacuum at 60° C. for 12 hrs to afford (3R,5R)-7-{2-(4-fluoro-phenyl)-4-isopropyl-5-[methyl-(2-methyl-benzyl)-carbamoyl]-2H-pyrazol-3-yl}-3,5-dihydroxy-heptanoic acid sodium salt (798 mg, 99%): MS(APCI⁺) 526.3 m/z (M+H); H-NMR (DMSO-d₆) [Mixture of rotamers at 25° C.] δ 7.79-7.65, 7.58-7.46, 7.41-7.24, 7.22-7.07, 4.85-4.60, 3.62-3.58, 3.46-3.44, 2.89-2.85, 2.84, 2.74-2.66, 2.54-2.45, 2.29, 1.93-1.88, 1.73-1.67, 1.53-1.10.

Example 90

(3R,5R)-7-[5-(2-fluoro-benzyl)-methyl-carbamoyl]-2-(4-fluoro-phenyl)-4-isopropyl-2H-pyrazol-3-yl}-3,5-dihydroxy-heptanoic acid sodium salt

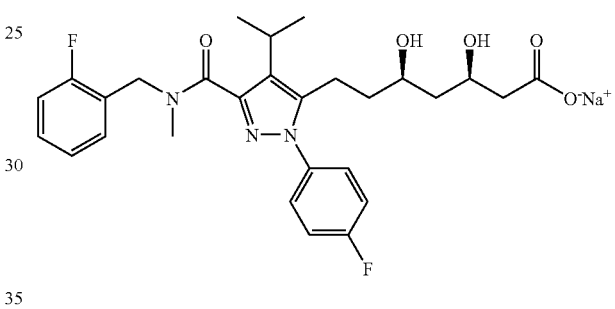

The title compound was prepared in a manner analogous to the method of Example 1: MS(APCI⁺) 530.3 m/z (M+H); H-NMR (DMSO-d₆) [Mixture of rotamers at 25° C.] δ 7.55-7.10, 4.74, 4.70, 4.67, 3.67-3.62, 3.51-3.44, 2.92, 2.88, 2.75-2.69, 2.59-2.53, 1.95-1.90, 1.75-1.69, 1.39-1.11.

Example 91

(3R,5R)-7-[5-[(3,4-difluoro-benzyl)-methyl-carbamoyl]-2-(4-fluoro-phenyl)-4-isopropyl-2H-pyrazol-3-yl]-3,5-dihydroxy-heptanoic acid sodium salt

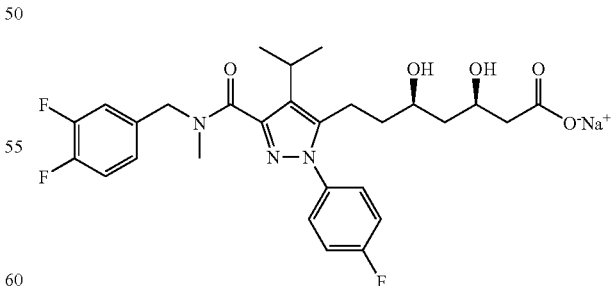

The title compound was prepared in a manner analogous to the method of Example 89: MS(APCI⁺) 548.2 m/z (M+H); H-NMR (DMSO-d₆) [Mixture of rotamers at 25° C. ] δ 7.50-7.21, 4.62, 4.50, 3.56-3.61, 3.51-3.45, 2.86, 2.84, 2.76-2.69, 2.54-2.50, 1.94-1.90, 1.75-1.71, 1.41-1.07.

Example 92

(3R,5R)-7-[5-(3-ethoxymethyl-benzylcarbamoyl)-2-(4-fluoro-phenyl)-4-isopropyl-2H-pyrazol-3yl]-3,5-dihydroxy-heptanoic acid sodium salt

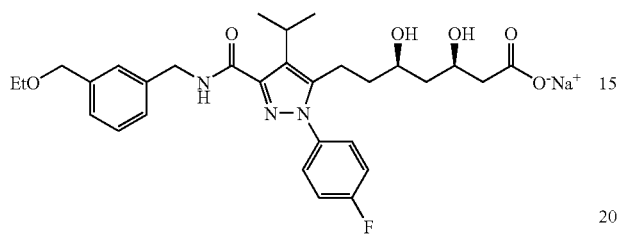

The title compound was prepared in a manner analogous to the method of Example 89: MS(APCI⁺) 556.2 m/z (M+H); H-NMR (DMSO-d₆) δ 7.55-7.51 (m, 2 H), 7.34-7.30 (m, 2 H), 7.25-7.10 (m, 4 H), 4.37 (s, 2 H), 4.36 (s, 2 H), 3.66-3.61 (m, 1 H), 3.49-3.43 (m, 1 H), 3.41 (q, 2 H), 2.76-2.71 (m, 1 H), 2.57-2.51 (m, 1 H), 1.97-1.92 (m, 1 H), 1.77-1.71 (m, 1 H), 1.39-1.12 (m, 10 H), 1.09 (t, 3 H).

Example 93

(3R,5R)-7-[5-(4-ethyl-benzylcarbamoyl)-2-(4-fluoro-phenyl)-4-isopropyl-2H-pyrazol-3-yl]-3,5-dihydroxy-heptanoic acid sodium salt

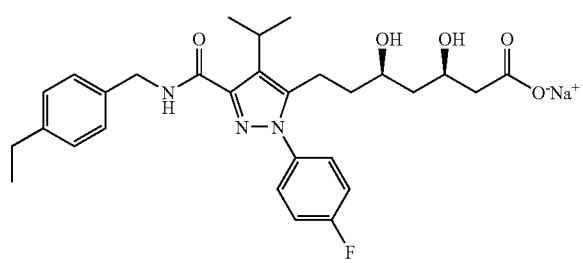

The title compound was prepared in a manner analogous to the method of Example 89:H-NMR (DMSO-dr) δ 7.55-7.51 (m, 2 H), 7.35-7.30 (m, 2 H), 7.23-7.10 (m, 4 H), 4.32 (s, 2 H), 3.65-3.60 (m, 1 H), 3.49-3.44 (m, 1 H), 3.23-3.21 (m, 1 H), 2.75-2.71 (m, 1 H), 2.69-2.61 (m, 1 H), 2.51 (q, 2 H), 1.97-1.92 (m, 1 H), 1.77-1.71 (m, 1 H), 1.39-1.14 (m, 10 H), 1.11 (t, 3 H).

Example 94

(3R,5R)-7-{2-(4-fluoro-phenyl)-4-isopropyl-5-[(5-trifluoromethyl-pyridin-2-ylmethyl)-carbamoyl]-2H-pyrazol-3-yl}-3,5-dihydroxy-heptanoic acid sodium salt The title compound was prepared in a manner analogous to the method of Example 89: MS(APCI⁺) 567.1 m/z (M+H); H-NMR (DMSO-d₆) δ 8.86 (s, 1 H), 8.78 (t, 1 H), 8.15 (d, 1 H), 7.58-7.54 (m, 2 H), 7.48 (d, 1 H), 7.37-7.33 (m, 2 H), 4.80-4.73 (m, 1 H), 4.55 (d, 2 H), 3.70-3.58 (m, 1 H), 3.55-3.42 (m, 1 H), 3.24-3.20 (m, 1 H), 2.80-2.63 (m, 1 H), 2.61-2.42 (m, 1 H), 1.95-1.90 (m, 1 H), 1.75-1.69 (m, 1 H), 1.42-1.30 (m, 1 H), 1.29-1.20 (m, 10 H), 1.17-1.12 (m, 1 H).

Example 95

(3R,5R)-7-{2-(4-fluoro-phenyl)-4-isopropyl-5-[(6-trifluoromethyl-pyridin-3-ylmethyl)-carbamoyl]-2H-pyrazol-3-yl}-3,5-dihydroxy-heptanoic acid sodium salt

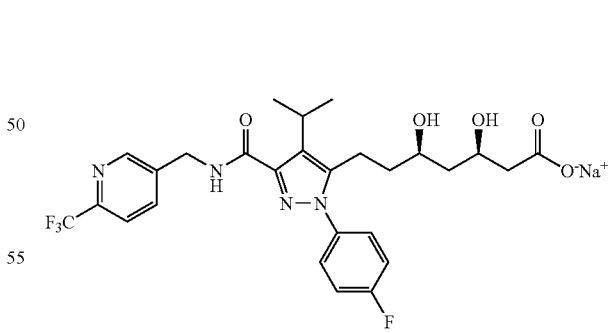

The title compound was prepared in a manner analogous to the method of Example 89: MS(APCI⁺) 567.1 m/z (M+H); H-NMR (DMSO-d₆) δ 8.85 (t, 1 H), 8.70 (s, 1 H), 7.96 (d, 1 H), 7.86 (d, 1 H), 7.58-7.56 (m, 2 H), 7.39-7.34 (m, 2 H), 4.73-4.78 (m, 1 H), 4.51 (d, 2 H), 3.67-3.55 (m, 1 H), 3.45-3.45 (m, 1 H), 3.26-3.18 (m, 1 H), 2.80-2.68 (m, 1 H), 2.64-2.55 (m, 1 H), 1.97-1.92 (m, 1 H), 1.77-1.65 (m, 1 H), 1.42-1.21 (m, 10 H), 1.20-1.10 (m, 2 H).

Example 96

(3R,5R)-7-{2-(4-fluoro-phenyl)-4-isopropyl-5-[(6-trifluoromethyl-piperidin-3-ylmethyl)-carbamoyl]-2H-pyrazol-3-yl}-3,5-dihydroxy-heptanoic acid sodium salt

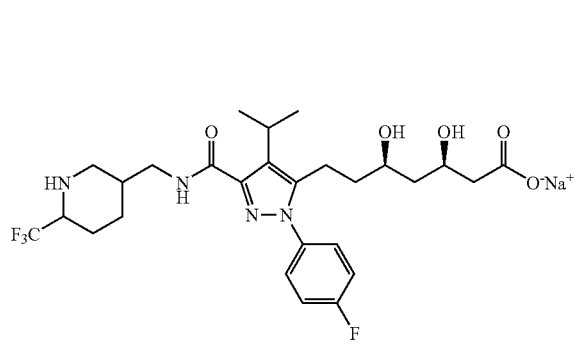

The title compound was prepared in a manner analogous to the method of Example 89: MS(APCI+) 573.3 m/z (M+H); H-NMR (DMSO-d6) [A mixture of diastereomers] δ 8.11-8.08, 7.54-7.40, 7.36-7.28, 4.76-4.63, 3.64-3.58, 3.51-3.40, 3.22-3.11, 3.03-2.96, 2.80-2.60, 2.59-2.47, 2.40-2.35, 1.95-1.90, 1.82-1.62, 1.60-1.40, 1.39-1.02.

Example 97

(3R,5R)-7-[2-(4-fluoro-phenyl)-4-isopropyl-5-(4-isopropyl-benzylcarbamoyl)-2H-pyrazol-3-yl]-3,5-dihydroxy-heptanoic acid sodium salt

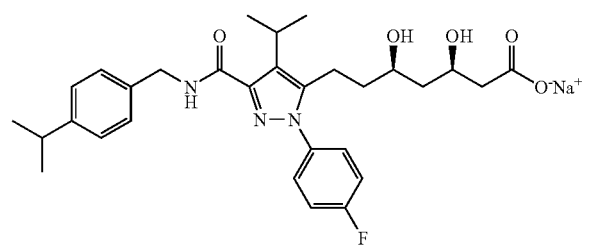

The title compound was prepared in a manner analogous to the method of Example 89: MS(APCI+) 540.1 m/z (M+H); H-NMR (DMSO-d6) δ 8.50 (t, 1 H), 7.54-7.50 (m, 3 H), 7.49-7.34 (m, 2 H), 7.32-7.11 (m, 3 H), 4.76-4.70 (m, 1 H), 4.31 (d, 1 H), 3.68-3.59 (m, 1 H), 3.50-3.41 (m, 1 H), 3.36-3.29 (m, 1 H), 3.24-3.16 (m, 1 H), 2.84-2.76 (m, 1 H), 2.75-2.63 (m, 1 H), 2.60-2.43 (m, 1 H), 1.95-1.90 (m, 1 H), 1.75-1.69 (m, 1 H), 1.42-1.30 (m, 1 H), 1.29-1.16 (m, 10 H), 1.13 (d, 6 H).

Example 98

(3R,5R)-7-[2-(4-fluoro-phenyl)-4-isopropyl-5-(3R-phenyl-piperidine-1-carbonyl)-2H-pyrazol-3-yl]-3,5-dihydroxy-heptanoic acid sodium salt

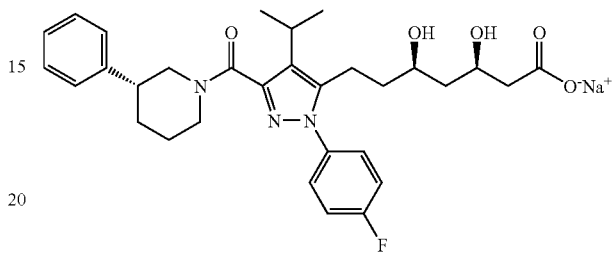

The title compound was prepared in a manner analogous to the method of Example 89: MS(APCI+) 552.1 m/z (M+H); H-NMR (DMSO-d6) [Mixture of rotamers at 25° C.] δ 7.52-7.43. 7.42-7.38, 7.36-7.03, 4.80-4.63, 4.60-4.50, 3.80-3.53, 3.50-3.33, 3.26-3.24, 3.20-3.02, 2.98-2.78, 2.76-2.44, 1.98-1.87, 1.84-1.61, 1.59-1.15.

Example 99

(3R,5R)-7-[2-(4-fluoro-phenyl)-4-isopropyl-5-(3S-phenyl-piperidine-1-carbonyl)-2H-pyrazol-3-yl]-3,5-dihydroxy-heptanoic acid sodium salt

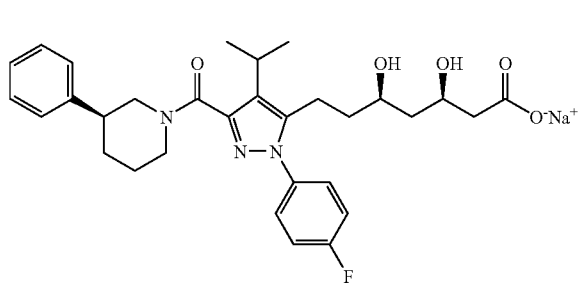

The title compound was prepared in a manner analogous to the method of Example 89:H-NMR (DMSO-d6) [Mixture of rotamers at 25° C.] δ 7.54-7.09, 4.74-4.72, 4.62-4.51, 3.78-3.57, 3.51-3.45, 3.08-3.02, 2.89-2.80, 2.79-2.49, 1.97-1.85, 1.83-1.61, 1.58-1.11.

Example 100

(3R,5R)-7-{2-(4-fluoro-phenyl)-4-isopropyl-5-[(6-methyl-pyridin-3-ylmethyl)-carbamoyl]-2H-pyrazol-3-yl}-3,5-dihydroxy-heptanoic acid sodium salt

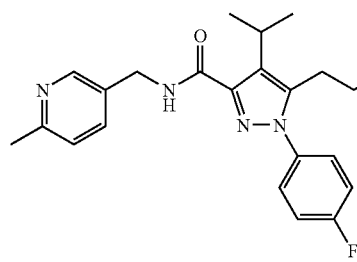

The title compound was prepared in a manner analogous to the method of Example 89: MS(APCI$^+$). 513.1 m/z (M+H); H-NMR (DMSO-d$_6$) δ 8.64 (t, 1 H), 8.34 (d, 1 H), 7.59-7.51 (m, 3 H), 7.49-7.38 (m, 1 H), 7.35-7.31 (m, 2 H), 7.15 (d, 1 H), 4.77-4.68 (m, 1 H), 4.32 (d, 2 H), 3.63-3.59 (m, 1 H), 3.49-3.40 (m, 1 H), 3.24-3.19 (m, 1 H), 2.76-2.62 (m, 1 H), 2.60-2.44 (m, 1 H), 2.38 (s, 3 H), 1.95-1.91 (m, 1 H), 1.75-1.70 (m, 1 H), 1.40-1.19 (m, 10 H), 1.19-1.11 (m, 1 H).

Example 101

(3R,5R)-7-[5-ethylcarbamoyl-2-(4-fluoro-phenyl)-4-isopropyl-2H-pyrazol-3-yl]-3,5-dihydroxy-heptanoic acid sodium salt

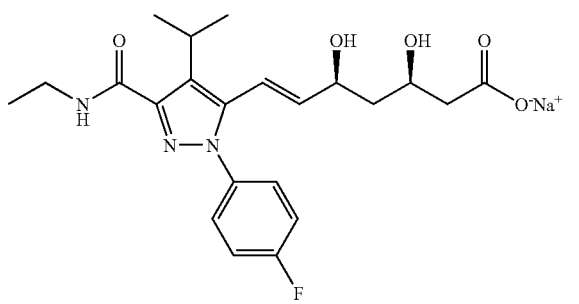

The title compound was prepared in a manner analogous to the method of Example 89: MS(APCI$^+$) 434.3 m/z (M+H); H-NMR (DMSO-d$_6$) δ 8.09-8.04 (m, 1 H), 7.50-7.46 (m, 2 H), 7.32-7.27 (m, 2 H), 7.22-7.12 (m, 1 H), 6.26 (d, 1 H), 5.66 (dd, 1 H), 5.13 (s, 1 H), 4.21-4.14 (m, 1 H), 3.65-3.55 (m, 1 H), 3.41-3.27 (m, 1 H), 3.23-3.15 (m, 2 H), 2.00-1.94 (m, 1 H), 1.80-1.75 (m, 1 H), 1.49-1.40 (m, 1 H), 1.38-1.07 (m, 8 H), 1.02 (t, 3 H).

Example 102

(3R,5R)-7-[2-(4-fluoro-phenyl)-4-isopropyl-5-phenylcarbamoyl-2H-pyrazol-3-yl]-3,5-dihydroxy-hept-6-enoic acid sodium salt

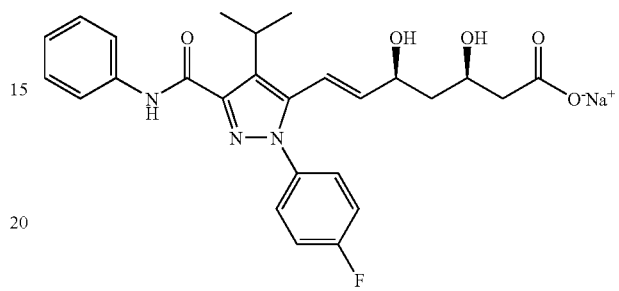

The title compound was prepared in a manner analogous to the method of Example 1: MS(APCI$^+$) 482.2 m/z(M+H); H-NMR (DMSO-d$_6$) δ 7.82-7.58 (m, 5 H), 7.43-7.23 (m, 4 H), 7.02 (t, 1 H), 6.17 (d, 1 H), 5.76 (t, 1 H), 4.95-4.71 (m, 1 H), 3.97-3.81 (m, 1 H), 3.58-3.41 (m, 1 H), 3.21-3.05 (m, 1 H), 2.55-2.39 (m, 1 H), 1.84-1.71 (m, 1 H), 1.62 (m, 1 H), 1.40-1.08 (m, 8 H), 0.83-0.65 (m, 1 H).

Example 103

(3R,5R)-7-[5-(cyclohexylmethyl-carbamoyl)-2-(4-fluoro-phenyl)-4-isopropyl-2H-pyrazol-3-yl]-3,5-dihydroxy-hept-6-enoic acid sodium salt

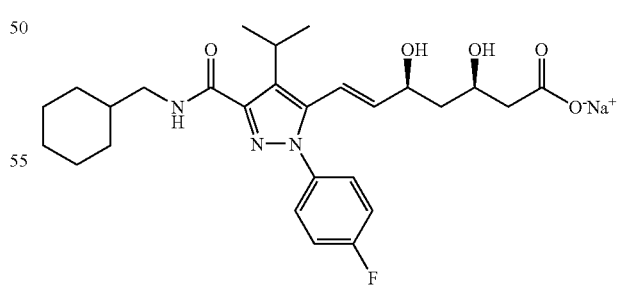

The title compound was prepared in a manner analogous to the method of Example 1: MS(APCI$^+$) 502.3 m/z (M+H); H-NMR (DMSO-d$_6$) δ 7.51-7.47 (m, 2 H), 7.33-7.28 (m, 2 H), 6.26 (d, 1 H), 5.68 (dd, 1 H), 4.19-4.16 (m, 1 H), 3.61-3.59 (m, 1 H), 3.42-3.39 (m, 1 H), 3.00 (d, 2 H), 1.97-1.92 (m, 2 H), 1.78-1.72 (m, 1 H), 1.63-0.88 (m, 19 H).

Example 104

(3R,5R)-7-[2-(4-fluoro-phenyl)-4-isopropyl-5-propylcarbamoyl-2H-pyrazol-3-yl]-3,5-dihydroxy-hept-6-enoic acid sodium salt

Example 106

(3R,5R)-7-[2-(4-fluoro-phenyl)-5-isobutylcarbamoyl-4-isopropyl-2H-pyrazol-3-yl]-3,5-dihydroxy-hept-6-enoic acid sodium salt

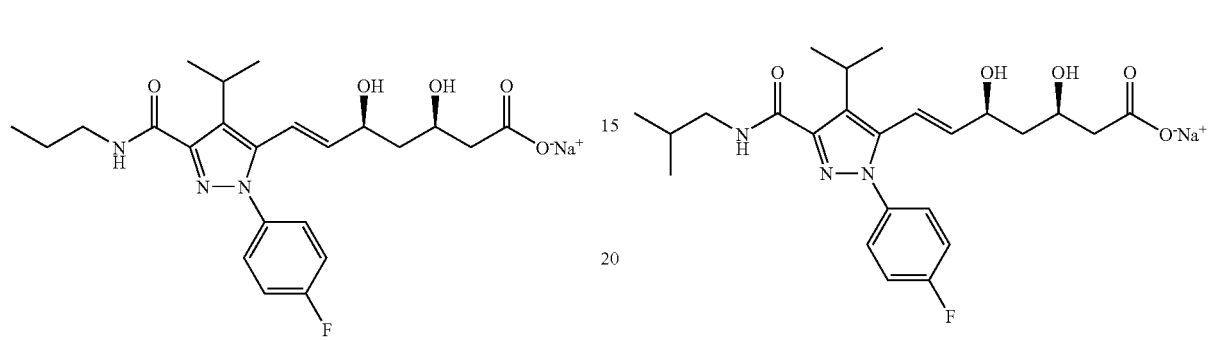

The title compound was prepared in a manner analogous to the method of Example 1: MS(APCI⁺) 448.3 m/z (M+H).

The title compound was prepared in a manner analogous to the method of Example 1: MS(APCI⁺) 462.3 m/z (M+H); H-NMR (DMSO-$d_6$) δ 8.05 (bs, 1 H), 7.51-7.48 (m, 2 H), 7.32-7.28 (m, 2 H), 6.26 (d, 1 H), 5.69 (dd, 1 H), 4.19-4.16 (m, 1 H), 3.62-3.58 (m, 1 H), 3.18 (d, 2 H), 1.96-1.92 (m, 1 H), 1.79-1.72 (m, 2 H), 1.48-1.41 (m, 1 H), 1.29-1.23 (m 7 H), 0.80 (d, 6 H).

Example 105

(3R,5R)-7-[2-(4-fluoro-phenyl)-4-isopropyl-5-isopropylcarbamoyl-2H-pyrazol-3-yl]-3,5-dihydroxy-hept-6-enoic acid sodium salt

Example 107

(3R,5R)-7-[5-cyclopentylcarbamoyl-2-(4-fluoro-phenyl)-4-isopropyl-2H-pyrazol-3-yl]-3,5-dihydroxy-hept-6-enoic acid sodium salt

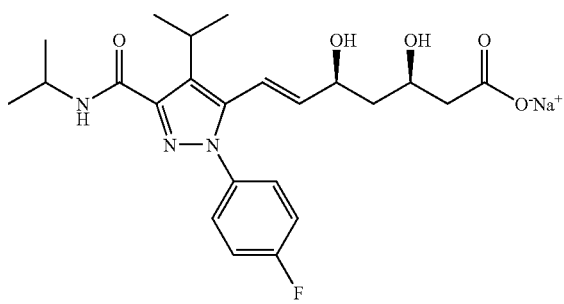

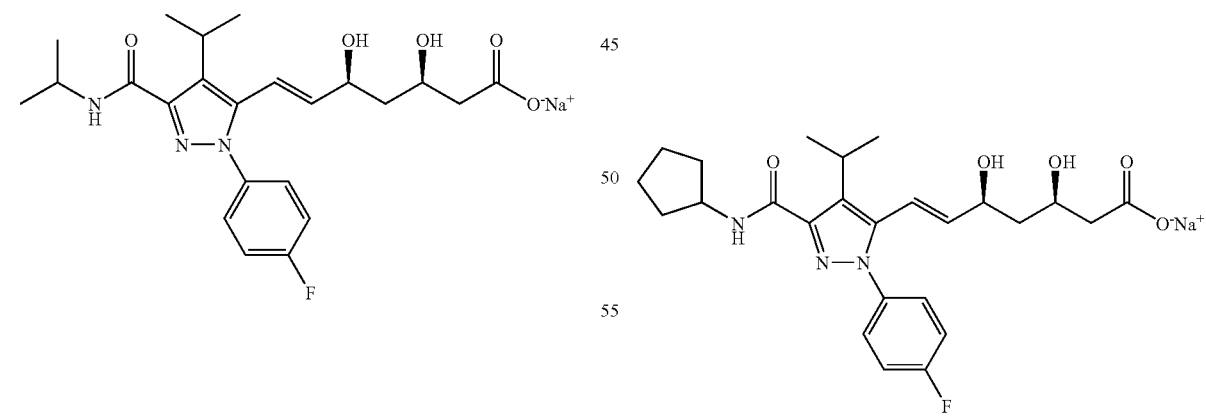

The title compound was prepared in a manner analogous to the method of Example 1: MS(APCI⁺) 448.3 m/z (M+H); H-NMR (DMSO-$d_6$) δ 7.83-7.77 (m, 1 H), 7.60-7.41 (m, 2 H), 7.40-7.22, (m, 2 H), 6.27 (d, 1 H), 5.71-5.14 (m, 1 H), 5.22-5.04 (m, 1 H), 4.26-4.10 (m, 1 H), 4.08-4.00 (m, 1 H), 3.67-3.51 (m, 1 H), 2.01-1.89 (m, 1 H), 1.82-1.70 (m, 1 H), 1.50-1.40 (m, 1 H), 1.37-1.05 (m, 15 H).

The title compound was prepared in a manner analogous to the method of Example 1: MS(APCI⁺) 474.3 m/z (M+H); H-NMR (DMSO-$d_6$) δ 7.52-7.47 (m, 2 H), 7.31-7.27 (m, 2 H), 6.26 (d, 1 H), 5.68 (dd, 1 H), 4.16-4.10 (m, 2 H), 3.63-3.60 (m, 1 H), 3.21-3.15 (m, 1 H), 1.97-1.93 (m, 1 H), 1.79-1.73 (m, 4 H), 1.60-1.53 (m, 2 H), 1.47-1.40 (m, 4 H), 1.36-1.17 (m, 7 H).

Example 108

(3R,5R)-7-[2-(4-fluoro-phenyl)-4-isopropyl-5-(3-methyl-butylcarbamoyl)-2H-pyrazol-3-yl]-3,5-dihydroxy-hept-6-enoic acid sodium salt

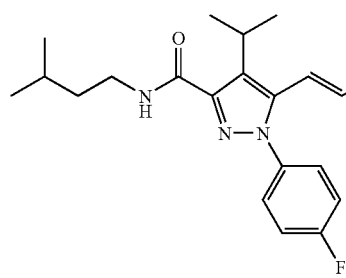

The title compound was prepared in a manner analogous to the method of Example 1: (M+H); H-NMR (DMSO-d₆) δ 8.01 (bs, 1 H), 7.50-7.47 (m, 2 H), 7.32-7.28 (m, 2 H), 6.26 (d, 1 H), 5.67 (dd, 1 H), 4.17-4.16 (m, 1 H), 3.16-3.59 (m, 1 H), 3.19-3.17 (m, 2 H), 1.97-1.92 (m, 1 H), 1.78-1.72 (m, 1 H), 1.56-1.49 (m, 3 H), 1.39-1.19 (m, 8 H), 0.82 (d, 6 H).

Example 109

(3R,5R)-7-[5-(cyclopropylmethyl-carbamoyl)-2-(4-fluoro-phenyl)-4-isopropyl-2H-pyrazol-3-yl]-3,5-dihydroxy-hept-6-enoic acid sodium salt

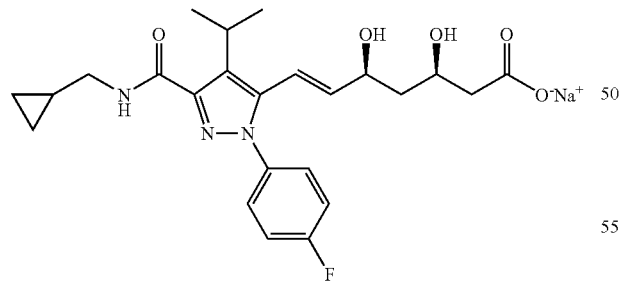

The title compound was prepared in a manner analogous to the method of Example 1: MS(APCI⁺) 460.3 m/z (M+H); H-NMR (DMSO-d₆) δ 7.50-7.46 (m, 2 H), 7.31-7.27 (m, 2 H), 6.26 (d, 1 H), 5.56 (dd, 1 H), 4.19-4.16 (m, 1 H), 3.63-3.59 (m, 1 H), 3.30-3.26 (m, 1 H), 3.04 (d, 2 H), 1.95-1.90 (m, 1 H), 1.77-1.71 (m, 1 H), 1.39-1.10 (m, 8 H), 0.98-0.94 (m, 1 H), 0.34-0.31 (m, 2 H), 0.17-0.14 (m, 2 H).

Example 110

(3R,5R)-7-[5-butylcarbamoyl-2-(4-fluoro-phenyl)-4-isopropyl-2H-pyrazol-3-yl]-3,5-dihydroxy-hept-6-enoic acid sodium salt

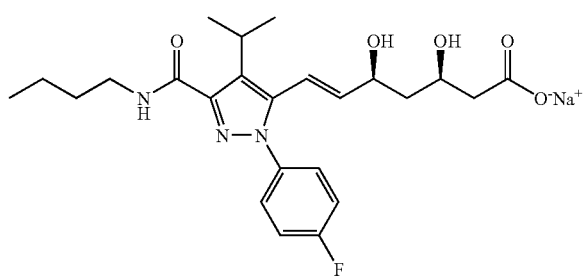

The title compound was prepared in a manner analogous to the method of Example 1: MS(APCI⁺) 462.3 m/z (M+H); H-NMR (DMSO-d₆) δ 8.10-8.05 (m, 1 H), 7.52-7.47 (m, 2 H), 7.35-7.28 (m, 2 H), 7.01 (s,1 H), 6.31-6.27 (m, 1 H), 6.73-5.67 (m, 1 H), 5.16 (s, 1 H), 4.23-4.16 (m, 1 H), 3.65-3.58 (m, 1 H), 3.36-3.18 (m, 3 H), 2.03-1.95 (m, 1 H), 1.85-1.79 (m, 1 H), 1.53-1.33 (m, 3 H), 1.31-1.21 (m, 10 H), 0.85 (t, 3 H).

Example 111

(3R,5R)-7-{2-(4-fluoro-phenyl)-4-isopropyl-5-[methyl-(3-trifluoromethoxy-benzyl)-carbamoyl]-2H-pyrazol-3-yl}-3,5-dihydroxy-hept-6-enoic acid sodium salt

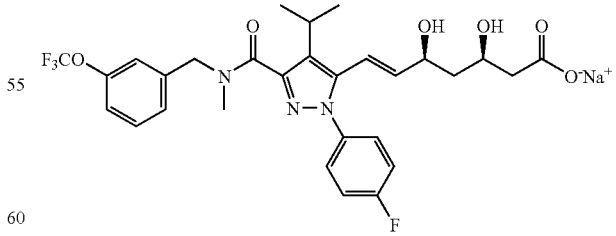

The title compound was prepared in a manner analogous to the method of Example 1: MS(APCI⁺) 594.3 m/z (M+H); H-NMR (DMSO-d₆) [Mixture of rotamers at 25° C.] δ 7.52-7.46, 7.36-7.25, 6.29-6.24, 5.86-5.73, 5.17, 4.71, 4.61, 4.24-4.21, 3.68-3.65, 2.91, 2.88, 1.99-1.95, 1.83-1.79, 1.49-1.12.

Example 112

(3R,5R)-7-[5-cyclohexylcarbamoyl-2-(4-fluoro-phenyl)-4-isopropyl-2H-pyrazol-3-yl]-3,5-dihydroxy-hept-6-enoic acid sodium salt

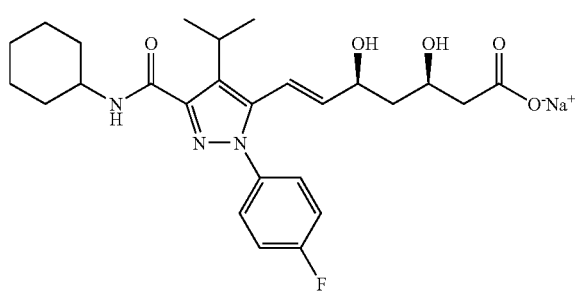

The title compound was prepared in a manner analogous to the method of Example 1: MS(APCI$^+$) 488.2 m/z (M+H); H-NMR (DMSO-d$_6$) δ 7.82-7.76 (m, 1 H), 7.58-7.43 (m, 1 H), 7.41 (s, 1 H), 7.35-7.27 (m, 2 H), 6.29 (d, 1 H), 5.71 (dd, 1 H), 5.21-5.18 (m, 1 H), 4.21-4.18 (m, 1 H), 3.78-3.66 (m, 1 H), 3.65-3.60 (m, 1 H), 3.22-3.17 (m, 1H), 2.00-1.96 (m, 1 H), 1.82-1.60 (m, 4 H), 1.39-1.40 (m, 2 H), 1.38-1.02 (m, 15 H).

Example 113

(3R,5R)-7-[5-(4-cyano-benzylcarbamoyl)-2-(4-fluoro-phenyl)-4-isopropyl-2H-pyrazol-3yl]-3,5-dihydroxy-hept-6-enoic acid sodium salt

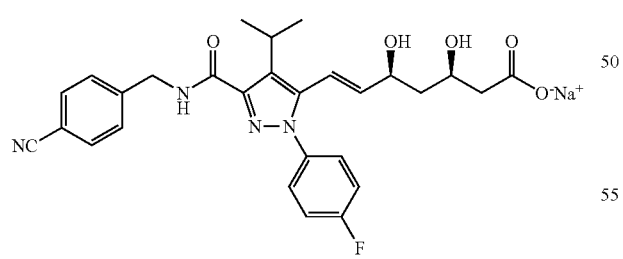

The title compound was prepared in a manner analogous to the method of Example 1: MS(APCI$^+$) 521.0 m/z (M+H); H-NMR (DMSO-d$_6$) δ 8.91-8.78 (m, 1 H), 7.95-7.70 (m, 2 H), 7.63-7.41 (m, 4 H), 7.40-7.23 (m, 2 H), 6.33-6.23 (m, 1 H), 5.80-5.64 (m, 1 H), 5.23-5.18 (m, 1 H), 4.45-4.35 (m, 2 H), 4.23-4.18 (m, 1 H), 3.64-3.58 (m, 1 H), 2.10-1.95 (m, 1 H), 1.82-1.71 (m, 1 H), 1.56-1.42 (m, 1 H), 1.40-1.05 (m, 10 H).

Example 114

(3R,5R)-7-[5-(3-cyano-benzylcarbamoyl)-2-(4-fluoro-phenyl)-4-isopropyl-2H-pyrazol-3-yl]-3,5-dihydroxy-hept-6-enoic acid sodium salt

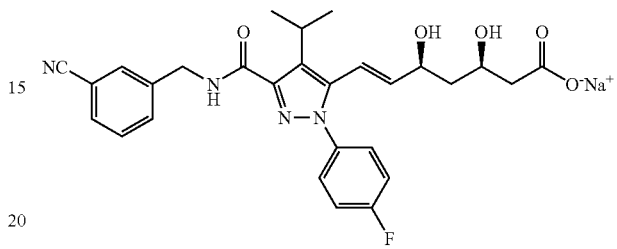

The title compound was prepared in a manner analogous to the method of Example 1: MS(APCI$^+$) 521.0 m/z (M+H); H-NMR (DMSO-d$_6$) δ 8.91-8.80 (m, 1 H), 7.70-7.62 (m, 2 H), 7.60-7.43 (m, 4 H), 7.37-7.32 (m, 2 H), 6.33-6.28 (m, 1 H), 5.78-5.72 (m, 1 H), 5.23-5.18 (m, 1 H), 4.45-4.35 (m, 2 H), 4.23-4.18 (m, 1 H), 3.64-3.59 (m, 1 H), 2.01-1.95 (m, 1 H), 1.81-1.71 (m, 1 H), 1.56-1.42 (m, 1 H), 1.40-1.05 (m, 10 H).

Example 115

(3R,5R)-7-[2-(4-fluoro-phenyl)-4-isopropyl-5-methylcarbamoyl-2H-pyrazol-3-yl]-3,5-dihydroxy-hept-6-enoic acid sodium salt

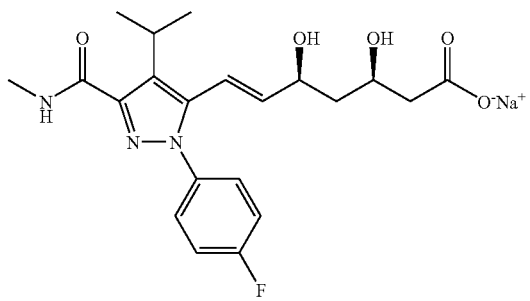

The title compound was prepared in a manner analogous to the method of Example 89: MS(APCI$^+$) 420.1 m/z (M+H); H-NMR (DMSO-d$_6$) δ 8.10-8.05 (m, 1 H), 7.53-7.50 (m, 2 H), 7.36-7.30 (m, 3 H), 6.33-6.28 (m, 1 H), 5.74-5.69 (m, 1 H), 5.22-5.15 (m, 1 H), 4.23-4.17 (m, 1 H), 3.70-3.60 (m, 1 H), 3.26-3.22 (m, 1 H), 2.71 (d, 3 H), 2.01-1.97 (m, 1 H), 1.83-1.77 (m, 1 H), 1.56-1.45 (m, 1 H), 1.33-1.06 (m, 9 H).

Example 116

(3R,5R)-7-{2-(4-fluoro-phenyl)-4-isopropyl-5-[methyl-(2-methyl-benzyl)-carbamoyl]-2H-pyrazol-3-yl}-3,5-dihydroxy-hept-6-enoic acid sodium salt

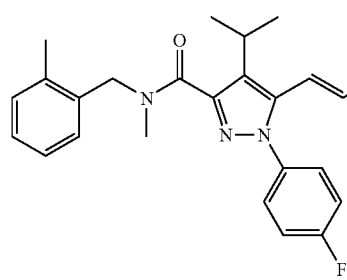

The title compound was prepared in a manner analogous to the method of Example 89: MS(APCI⁺) 524.1 m/z (M+H); H-NMR (DMSO-$d_6$) [Mixture of rotamers at 25° C.] δ 7.50-7.43, 7.42-7.40, 7.37-7.24, 7.21-7.11, 6.30-6.23, 5.86-5.75, 5.21-5.15, 4.68, 4.62, 4.24-4.18, 3.73-3.61, 3.07-2.97, 2.89, 2.86, 2.28, 2.15, 2.02-1.96, 1.83-1.76, 1.53-1.45, 1.41-1.26, 1.24-1.18.

Example 117

(3R,5R)-7-{2-(4-fluoro-phenyl)-4-isopropyl-5-[(6-methyl-pyridin-3-ylmethyl)-carbamoyl]-2H-pyrazol-3-yl}-3,5-dihydroxy-hept-6-enoic acid sodium salt

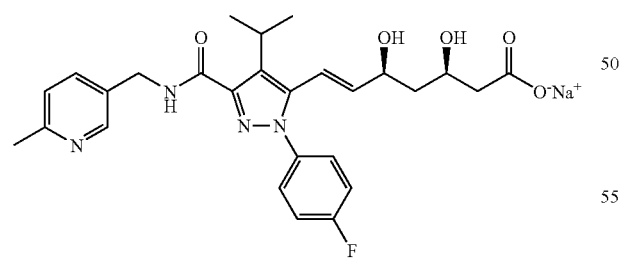

The title compound was prepared in a manner analogous to the method of Example 89: MS(APCI⁺) 511.3 m/z (M+H); H-NMR (DMSO-$d_6$) δ 8.72 (t, 1 H), 8.35 (d, 1 H), 7.57-7.50 (m, 3 H), 7.35-7.33 (m, 3 H), 7.15 (d, 1 H), 6.29 (d, 1 H), 5.74-5.69 (m, 1 H), 5.21-5.15 (m, 1 H), 4.35 (d, 1 H), 4.22-4.18 (d, 1 H), 3.64-3.58 (m, 1 H), 2.39 (s, 3 H), 2.00-1.96 (m, 1 H), 1.82-1.76 (m, 1 H), 1.50-1.44 (m, 1 H), 1.32-1.24 (m, 8 H).

Example 118

7-[5-[(2,6-difluoro-benzyl)-methyl-carbamoyl]-2-(4-fluoro-phenyl)-4-isopropyl-2H-pyrazol-3-yl-3,5-dihydroxy-heptanoic acid sodium salt

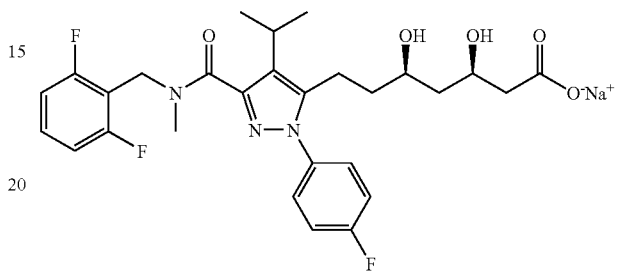

The title compound was prepared in a manner analogous to the method of Example 89: MS(APCI⁺) 548.2 m/z (M+H); H-NMR (DMSO-$d_6$) [Mixture of rotamers at 25° C.] δ 7.51-7.26, 7.12-7.03, 7.02-6.98, 4.82, 4.80-4.70, 3.63-3.58, 3.50-3.39, 2.93, 2.89-2.81, 2.80, 2.78-2.63, 2.60-2.45, 1.96-1.91, 1.76-1.70, 1.42-1.20, 1.19-1.04.

Example 119

7-[5-[(4-fluoro-2-methoxy-benzyl)-methyl-carbamoyl]-2-(4-fluoro-phenyl)-4-isopropyl-2H-pyrazol-3-yl]-3,5-dihydroxy-heptanoic acid sodium salt

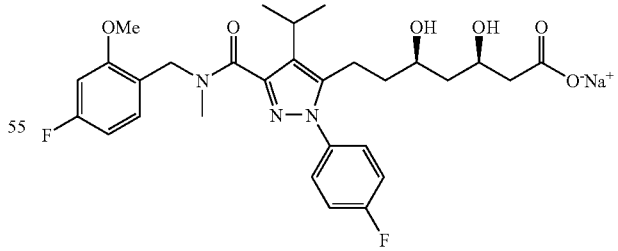

The title compound was prepared in a manner analogous to the method of Example 89: MS(APCI⁺) 560.2 m/z (M+H); H-NMR (DMSO-$d_6$) [Mixture of rotamers at 25° C.] δ 7.50-7.42, 7.35-7.20, 7.18-7.09, 6.88-6.81, 4.73, 4.61, 4.44, 3.78, 3.63-3.60, 3.50-3.42, 3.35-3.20, 2.95-2.85, 2.82, 2.80-2.63, 2.62-2.50, 1.96-1.92, 1.76-1.70, 1.33-1.22, 1.20-1.13.

Example 120

7-{2-(4-fluoro-phenyl)-4-isopropyl-5-[methyl-(2,3,4-trifluoro-benzyl)-carbamoyl]-2H-pyrazol-3-yl}-3,5-dihydroxy-heptanoic acid sodium salt

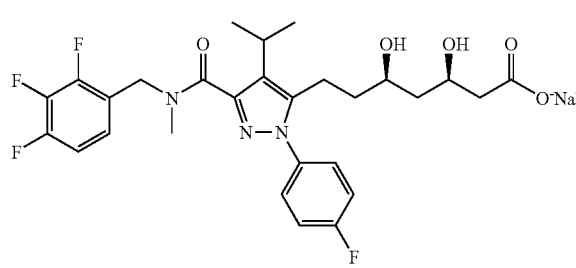

The title compound was prepared in a manner analogous to the method of Example 89: MS(APCI$^+$) 566.2 m/z (M+H); H-NMR (DMSO-d$_6$) [Mixture of rotamers at 25° C.] δ 7.50-7.42, 7.34-7.12, 4.70, 4.68, 3.63-3.61, 3.47-3.42, 2.91, 2.89, 2.76-2.72, 2.69-2.65, 1.97-1.92, 1.77-1.72, 1.42-1.27, 1.18-1.13.

Example 121

7-[5-[(3-fluoro-4-methoxy-benzyl)-methyl-carbamoyl]-2-(4-fluoro-phenyl-4-isopropyl-2H-pyrazol-3-yl]-3,5-dihydroxy-heptanoic acid sodium salt

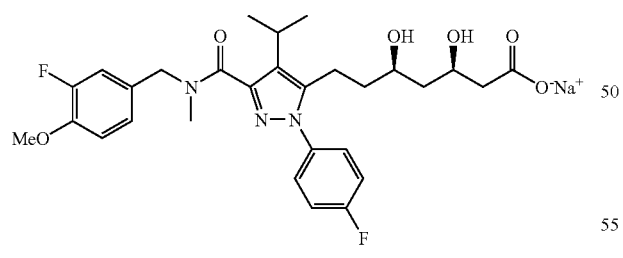

The title compound was prepared in a manner analogous to the method of Example 89: MS(APCI$^+$) 560.1 m/z (M+H); H-NMR (DMSO-d$_6$) [Mixture of rotamers at 25° C.] δ 7.50-7.42, 7.33-7.25, 7.18-7.04, 4.72, 4.56, 4.43, 3.79, 3.77, 3.71-3.60, 3.51-3.40, 3.38-3.33, 2.95-2.83, 2.81, 2.78-2.63, 2.60-2.43, 1.96-1.92, 1.76-1.71, 1.42-1.21, 1.19-1.14.

Example 122

7-{2-(4-fluoro-phenyl)-4-isopropyl-5-[methyl-(2,3,6-trifluoro-benzyl)-carbamoyl]-2H-pyrazol-3-yl}-3,5-dihydroxy-heptanoic acid sodium salt

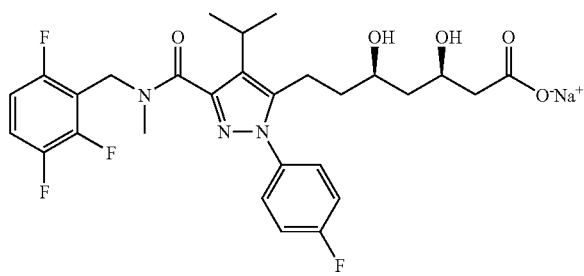

The title compound was prepared in a manner analogous to the method of Example 89: MS(APCI$^+$) 566.2 m/z (M+H); H-NMR (DMSO-d$_6$) [Mixture of rotamers at 25° C.] δ 7.50-7.40, 7.37-7.25, 7.18-7.08, 7.06-7.00, 4.86, 4.76, 4.72, 3.64-3.57, 3.52-3.40, 3.24-3.21, 2.97, 2.93-2.76, 2.75-2.60, 2.58-2.48, 1.96-1.91, 1.76-1.70, 1.42-1.20, 1.18-1.00.

Example 123

7-[5-[(2,3-difluoro-4-methyl-benzyl)-methyl-carbamoyl]-2-(4-fluoro-phenyl)-4-isopropyl-2H-pyrazol-3-yl]-3,5-dihydroxy-heptanoic acid sodium salt

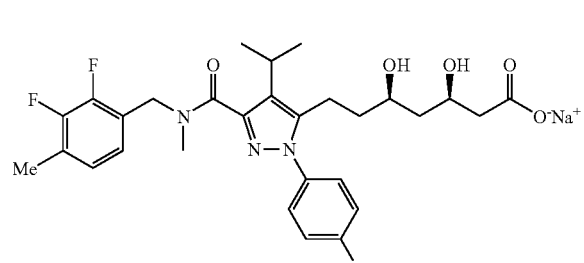

The title compound was prepared in a manner analogous to the method of Example 89: MS(APCI$^+$) 562.2 m/z (M+H); H-NMR (DMSO-d$_6$) [Mixture of rotamers at 25° C.] δ 7.55-6.93, 4.73, 4.69, 4.66, 3.65-3.61, 3.49-3.45, 2.90, 2.87, 2.74-2.71, 2.69-2.67, 2.26, 2.23, 2.20, 1.95-1.90, 1.74-1.69, 1.45-1.12.

Example 124

7-[5-[(2,3-difluoro-6-methoxy-benzyl)-methyl-carbamoyl]-2-(4-fluoro-phenyl)-4-isopropyl-2H-pyrazol-3-yl]-3,5-dihydroxy-heptanoic acid sodium salt

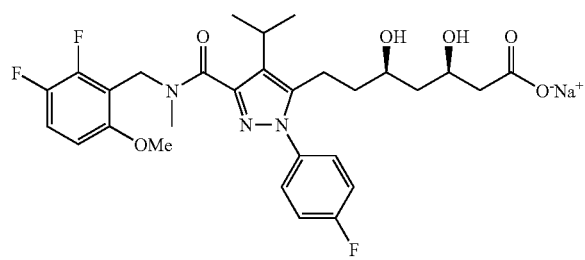

The title compound was prepared in a manner analogous to the method of Example 89: MS(APCI+) 578.2 m/z (M+H); H-NMR (DMSO-d6) [Mixture of rotamers at 25° C.] δ 7.50-7.09, 6.84-6.76, 4.75, 4.70, 3.77, 3.68, 3.65-3.61, 3.51-3.47, 2.88, 2.74, 2.73-2.68, 2.59-2.56, 2.26, 1.97-1.91, 1.77-1.07.

Example 125

7-[5-[(3-fluoro-4-methyl-benzyl)-methyl-carbamoyl]-2-(4-fluoro-phenyl)-4-isopropyl-2H-pyrazol-yl]-3,5-dihydroxy-heptanoic acid sodium salt

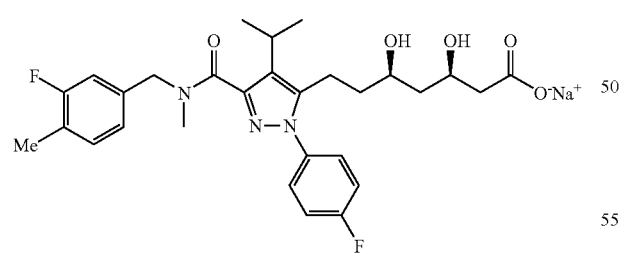

The title compound was prepared in a manner analogous to the method of Example 89: MS(APCI+) 544.2 m/z (M+H); H-NMR (DMSO-d6) δ [Mixture of rotamers at 25° C.] δ 7.75-7.40, 7.33-7.08, 7.06-6.98, 4.60, 4.48, 3.64-3.58, 3.45-3.38, 2.95-2.84, 2.82, 2.77-2.45, 2.18, 2.15, 1.96-1.91, 1.76-1.70, 1.43-1.22, 1.18-1.14.

Example 126

7-[5-[(4-fluoro-3-methyl-benzyl)-methyl-carbamoyl]-2-(4-fluoro-phenyl)-4-isopropyl-2H-pyrazol-3-yl]-3,5-dihydroxy-heptanoic acid sodium salt

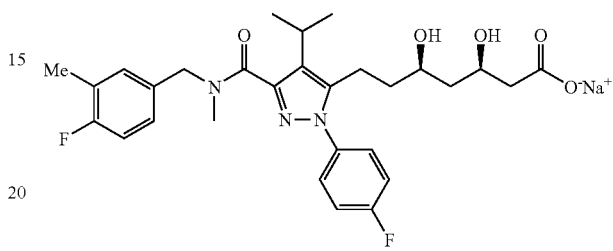

The title compound was prepared in a manner analogous to the method of Example 89: MS(APCI+) 544.2 m/z (M+H); H-NMR (DMSO-d6) [Mixture of rotamers at 25° C.] δ 7.65-7.40, 7.33-7.22, 7.18-7.02, 4.74, 4.58, 4.45, 3.64-3.58, 3.45-3.38, 2.95-2.84, 2.82, 2.77-2.45, 2.18, 2.15, 1.96-1.91, 1.76-1.70, 1.43-1.22, 1.18-1.14.

Example 127

7-[5-[(2,3-difluoro-4-methoxy-benzyl)-methyl-carbamoyl]-2-(4-fluoro-phenyl)-4-isopropyl-2H-pyrazol-3-yl]-3,5-dihydroxy-heptanoic acid sodium salt

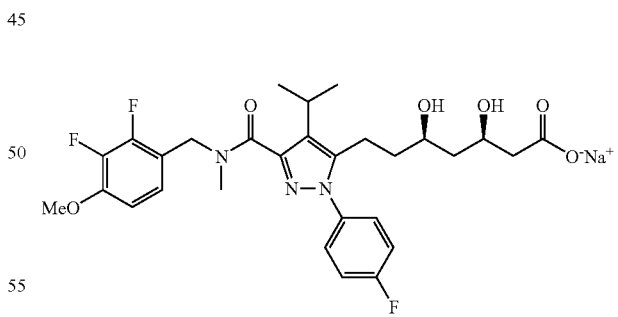

The title compound was prepared in a manner analogous to the method of Example 89: MS(APCI+) 578.2 m/z (M+H); H-NMR (DMSO-d6) [Mixture of rotamers at 25° C.] δ 7.58-7.57, 7.49-7.44, 7.33-7.29, 7.14-7.10, 7.03-6.95, 4.75, 4.66, 4.62, 3.83, 3.80, 3.64-3.60, 3.49-3.46, 2.89, 2.85, 2.74-2.67, 2.59-2.52, 1.94-1.90, 1.74-1.68, 1.42-1.11.

Example 128

7-[5-[(2-fluoro-3-methyl-benzyl)-methyl-carbamoyl]-2-(4-fluoro-phenyl)-4-isopropyl-2H-pyrazol-3-yl]-3,5-dihydroxy-heptanoic acid sodium salt

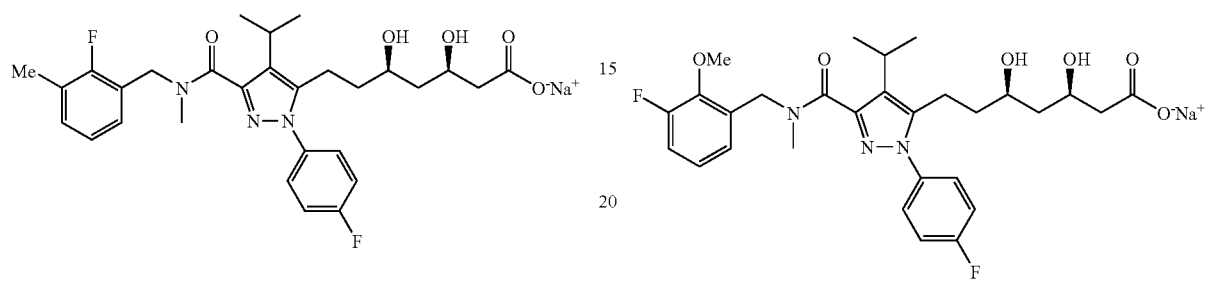

The title compound was prepared in a manner analogous to the method of Example 89: MS(APCI$^+$) 544.3 m/z (M+H); H-NMR (DMSO-d$_6$) [Mixture of rotamers at 25° C.] δ 7.50-7.48, 7.47-7.40, 7.33-7.27, 7.19-7.13, 7.07-6.97, 4.72, 4.68, 4.64, 3.64-3.62, 3.49-3.45, 2.91, 2.87, 2.76-2.72, 2.68-2.60, 2.21, 2.15, 1.96-1.92, 1.77-1.71, 1.57-1.29, 1.17-1.11.

Example 129

7-{2-(4-fluoro-phenyl)-4-isopropyl-5-[methyl-(2,3,5-trifluoro-benzyl)-carbamoyl]-2H-pyrazol-3-yl}-3,5-dihydroxy-heptanoic acid sodium salt

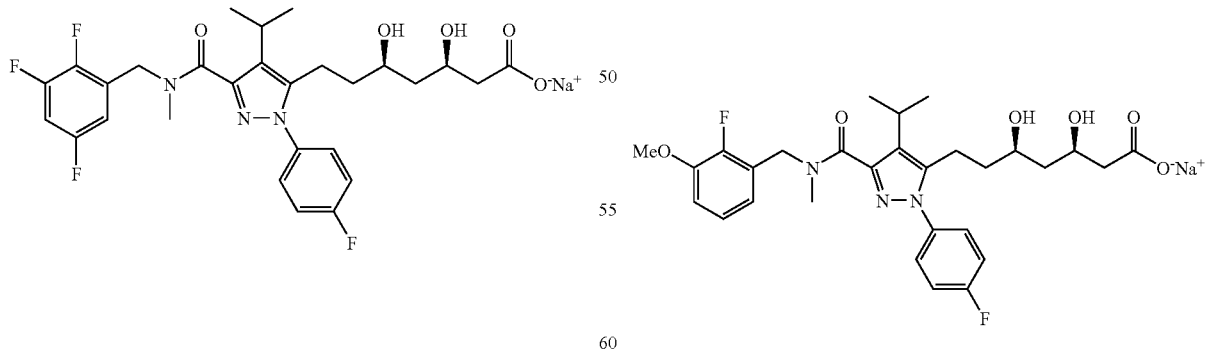

The title compound was prepared in a manner analogous to the method of Example 89:H-NMR (DMSO-d$_6$) [Mixture of rotamers at 25° C.] δ 7.59, 7.51-7.40, 7.34-7.28, 6.97, 4.73-4.71, 3.62-3.60, 3.49-3.45, 2.93, 2.87, 2.76-2.72, 2.71-2.636, 1.94-1.90, 1.74-1.68, 1.43-1.26, 1.17-1.12.

Example 130

7-[5-[(3-fluoro-2-methoxy-benzyl)-methyl-carbamoyl]-2-(4-fluoro-phenyl)-4-isopropyl-2H-pyrazol-3-yl]-3,5-dihydroxy-heptanoic acid sodium salt The title compound was prepared in a manner analogous to the method of Example 89: MS(APCI$^+$) 560.3 m/z (M+H); H-NMR (DMSO-d$_6$) [Mixture of rotamers at 25° C.] δ 7.50-7.26, 7.18-6.96, 4.73, 4.68, 4.63, 3.85, 3.70, 3.63-3.59, 3.49-3.42, 2.90, 2.87, 2.75-2.70, 2.61-2.57, 1.96-1.91, 1.76-1.70, 1.56-1.13.

Example 131

7-[5-[(2-fluoro-3-methoxy-benzyl)-methyl-carbamoyl]-2-(4-fluoro-phenyl)-4-isopropyl-2H-pyrazol-3-yl]-3,5-dihydroxy-heptanoic acid sodium salt The title compound was prepared in a manner analogous to the method of Example 89: MS(APCI$^+$) 560.3 m/z (M+H); H-NMR (DMSO-d$_6$) [Mixture of rotamers at 25° C.] δ 7.55-7.39, 7.33-7.29, 7.09-7.01, 4.68, 4.65, 3.80, 3.76, 3.63-3.61, 4.47-3.45, 2.90, 2.86, 2.72-2.68, 2.52-2.49, 2.47, 2.46, 1.96-1.91, 1.76-1.70, 1.47-1.12.

Example 132

[5-[(3-fluoro-2-methyl-benzyl)-methyl-carbamoyl]-2-(4-fluoro-phenyl)-4-isopropyl-2H-pyrazol-3-yl]-3,5-hydroxy-heptanoic acid sodium salt

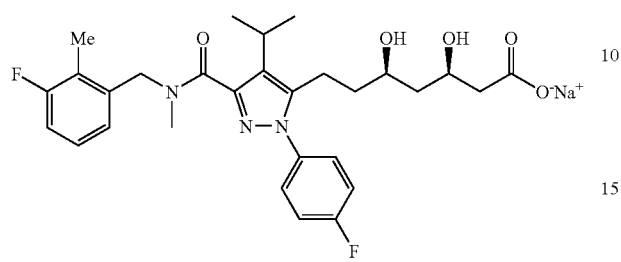

The title compound was prepared in a manner analogous to the method of Example 89: MS(APCI⁺) 544.3 m/z (M+H); H-NMR (DMSO-d₆) [Mixture of rotamers at 25° C.] δ 7.63, 7.51-7.47, 7.38-7.32, 7.29-7.14, 7.07-6.99, 4.74, 4.69, 4.63, 3.62-3.60, 3.48-3.45, 2.93-2.89, 2.87, 2.83, 2.73-2.70, 2.63-2.57, 2.18, 2.03, 1.93-1.89, 1.73-1.68, 1.37-1.12.

Example 133

1-(4-Fluoro-phenyl)-5-[2-(4-hydroxy-6-oxo-tetrahydro-pyran-2-yl)-ethyl]-4-isopropyl-1H-pyrazole-3-carboxylic acid (3-fluoro-benzyl)-methyl-amide

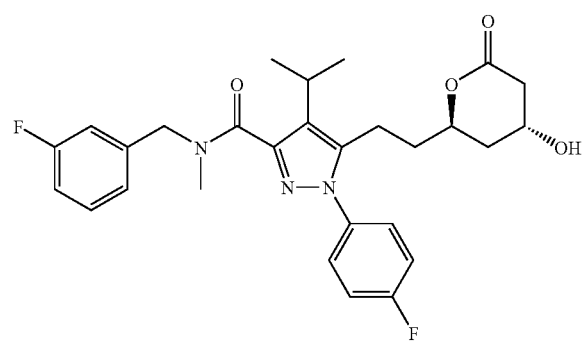

To a 7-[5-[(3-fluoro-benzyl)-methyl-carbamoyl]-2-(4-fluoro-phenyl)-4-isopropyl-2H-pyrazol-3-yl]-3,5-dihydroxy-heptanoic acid sodium salt (270 mg, 0.49 mmol) in MeCN (50 ml) was slowly added TFA (1.0 mL, 1.23 mmol). The reaction mixture was stirred at 25° C. and monitored by HPLC. After 2 hrs, the reaction was completed. The reaction mixture was diluted with EtOAc (150 ml) and washed with H₂O, saturated NaHCO₃, and brine. The organic layer was dried over Na₂SO₄ and concentrated. The crude product was purified by silica gel column chromatography (70% EtOAc/Hex) to afford 1-(4-fluoro-phenyl)-5-[2-(4-hydroxy-6-oxo-tetrahydro-pyran-2-yl)-ethyl]-4-isopropyl-1H-pyrazole-3-carboxylic acid (3-fluoro-benzyl)-methyl-amide (210 mg, 84%): MS(APCI⁺) 512.2 m/z (M+H); H-NMR (CDCl₃) [Mixture of rotamers at 25° C.] δ 7.40-7.21, 7.18-6.88, 4.72, 4.611, 4.58-4.48, 4.33-4.24, 2.98-2.93, 2.80-2.68, 2.63, 2.63 2.62, 2.61, 2.57, 2.56, 2.55, 2.17-2.14, 1.80-1.63, 1.61-1.58, 1.31-1.29.

Example 134

1-(4-Fluoro-phenyl)-5-[2-(4-hydroxy-6-oxo-tetrahydro-pyran-2-yl)-ethyl -4-isopropyl-1H-pyrazole-3-carboxylic acid benzyl-methyl-amide

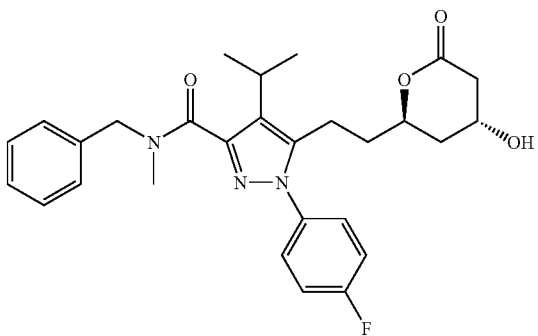

The title compound was prepared in a manner analogous to the method of Example 133: MS(APCI⁺) 494.2 m/z (M+H); H-NMR (CDCl₃) [Mixture of rotamers at 25° C.] δ 7.38-7.24, 7.17-7.10, 4.74, 4.61, 4.58-4.51, 4.33-4.28, 3.00-2.90, 2.80-2.70, 2.64-2.63, 2.62-2.57, 2.08-2.03, 1.75-1.63, 1.61-1.57, 1.32-1.28, 1.25-1.22.

Example 135

1-(4-Fluoro-phenyl)-5-[2-(4-hydroxy-6-oxo-tetrahydro-pyran-2-yl)-ethyl-4-isopropyl-1H-pyrazole-3-carboxylic acid 4-methyl-benzylamide

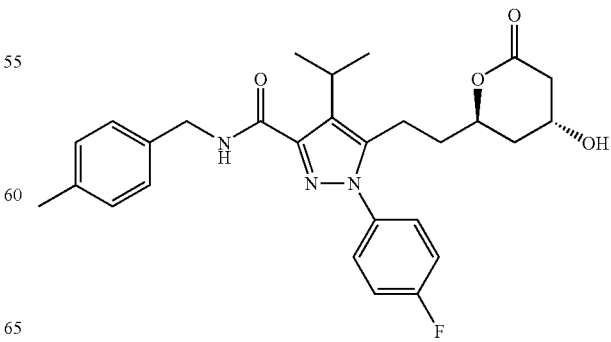

The title compound was prepared in a manner analogous to the method of Example 133: MS(APCI⁺) 494.1 m/z (M+H); H-NMR (CDCl₃) δ 7.35-7.32 (m, 2 H), 7.24-7.10 (m, 6 H), 4.56-4.51 (m, 3 H), 4.32-4.30 (m, 1 H), 2.95-2.89 (m, 1 H), 2.79-2.72 (m, 1 H), 2.68-2.67 (m, 1 H), 2.59-2.54 (m, 1 H), 2.30 (s, 3 H), 1.83-1.56 (m, 3 H), 1.38 (d, 6 H).

Example 136

(3R,5R)-7-[2-(4-Fluoro-phenyl)-4-isopropyl-5-(2-phenyl-piperidine-1-carbonyl)-2H-pyrazol-3-yl]-3,5-dihydroxy-heptanoic acid sodium salt

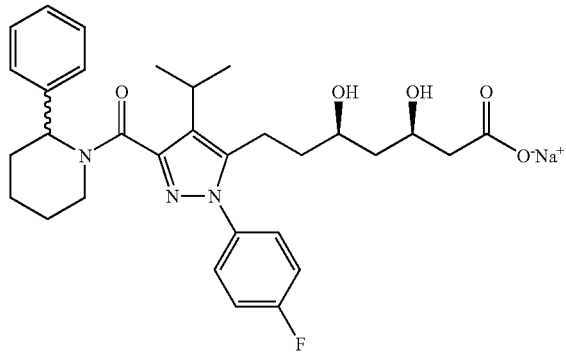

The title compound was prepared in a manner analogous to the method of Example 1: MS(APCI⁺) 552.2 m/z (M+H); H-NMR (DMSO-d₆) [Mixture of diastereomers] δ 7.68-7.43, 7.41-7.19, 5.93-5.83, 5.23-5.15, 4.78-4.69, 4.55-4.42, 3.70-3.58, 3.56-3.42, 2.99-2.83, 2.80-2.63, 2.62-2.51, 1.97-1.88, 1.86-1.63, 1.62-1.53, 1.49-1.12.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. Accordingly, the invention is limited only by the following claims.

The invention claimed is:

1. A compound which is (3R, 5R)-7-[2-(4-fluoro-phenyl)-4-isopropyl-5-(4-methyl-benzylcarbamoyl)-2H-pyrazol-3-yl]-3,5-dihydroxy-heptanoic acid of the formula

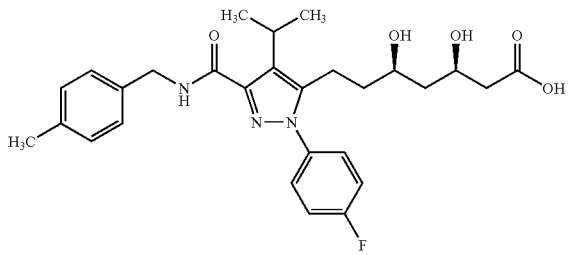

or a pharmaceutically acceptable salt thereof.

2. A sodium salt of the compound of claim 1.

3. A pharmaceutical composition comprising a salt according to claim 2 and a pharmaceutically acceptable carrier, diluent, solvent or vehicle.

4. A pharmaceutical composition comprising a compound according to claim 1, or a pharmaceutically acceptable salt thereof, and a pharmaceutically acceptable carrier, diluent, solvent or vehicle.

5. A method of treating a subject suffering from hyperlipidemia, hypercholesterolemia, hypertriglyceridemia, atherosclerosis, Alzheimer's Disease, benign prostatic hypertrophy (BPH), diabetes, and osteoporosis comprising administering a therapeutically effective amount of a compound of claim 1, or a pharmaceutically acceptable salt thereof, to a subject in need thereof.

6. A method of treating a subject suffering from hyperlipidemia, hypercholesterolemia, hypertriglyceridemia, atherosclerosis, Alzheimer's Disease, benign prostatic hypertrophy (BPH), diabetes, and osteoporosis comprising administering a therapeutically effective amount of the salt of claim 2 to a subject in need thereof.

7. A method according to claim 5 wherein said subject is suffering from hyperlipidemia.

8. A method according to claim 5 wherein said subject is suffering from hypercholesterolemia.

9. A method according to claim 5 wherein said patient is suffering from atherosclerosis.

10. A method according to claim 2 wherein said subject is suffering from hyperlipidemia.

11. A method according to claim 2 wherein said subject is suffering from hypercholesterolemia.

12. A method according to claim 2 wherein said patient is suffering from atherosclerosis.

* * * * *